US008900588B2

(12) United States Patent
Floch et al.

(10) Patent No.: US 8,900,588 B2
(45) Date of Patent: Dec. 2, 2014

(54) METHODS FOR TREATING BREAST CANCER

(75) Inventors: Jean-François Floch, Sète (FR); Leïla Houhou, Montpellier (FR); Françoise Cailler, Montpellier (FR); Dominique Joubert, Sète (FR); Frédéric Hollande, Les Matelles (FR)

(73) Assignees: Les Laboratories Servier, Suresnes (FR); Institut National de la Sante et de la Recherche Medicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 580 days.

(21) Appl. No.: 12/984,509

(22) Filed: Jan. 4, 2011

(65) Prior Publication Data
US 2011/0177062 A1    Jul. 21, 2011

Related U.S. Application Data

(60) Provisional application No. 61/293,612, filed on Jan. 8, 2010.

(51) Int. Cl.
*A61K 39/395*    (2006.01)
*C07K 16/26*    (2006.01)
*C07K 16/30*    (2006.01)
*G01N 33/574*    (2006.01)

(52) U.S. Cl.
CPC ............ *C07K 16/26* (2013.01); *C07K 16/303* (2013.01); *G01N 33/57438* (2013.01); *C07K 2317/73* (2013.01); *G01N 2333/595* (2013.01); *G01N 2800/52* (2013.01); *C07K 2317/34* (2013.01)
USPC ............... 424/158.1; 424/130.1; 424/141.1; 424/145.1; 424/155.1; 424/156.1; 424/172.1; 424/174.1

(58) Field of Classification Search
USPC .......... 424/130.1, 141.1, 145.1, 155.1, 156.1, 424/158.1, 172.1, 174.1
See application file for complete search history.

(56) References Cited

U.S. PATENT DOCUMENTS 8,158,128 B2 * 4/2012 Grimes .................. 424/158.1
2006/0051818 A1    3/2006 Adriaenssens et al.

FOREIGN PATENT DOCUMENTS

| EP | 2062597 A1 | 5/2009 |
| WO | WO 01/62288 A1 | 8/2001 |
| WO | WO 2006/032980 A1 | 3/2006 |
| WO | WO 2008/076454 A1 | 6/2008 |
| WO | WO 2009/042618 A | 4/2009 |

OTHER PUBLICATIONS

Rudikoff, et al., Proc. Natl. Acad. Sci. USA, 79: 1979-1983, 1979.*
Davies, D.R., and Padlan, E.A., Annu. Rev. Biochem., 59: 439-473, 1990.*
Casset, et al, Biochem. Biophys. Res. Commun. 307(1): 198-205, 2003.*
Holm, et al., Mol. Immunol. 44(6): 1075-1084, 2007.*
Reubi, J.C., et al, Cancer Research, 57: 1377-1386, 1997.*
Ferrand, A., et al. Cancer Letters 238: 15-29, 2005.*
Mihara, M. et al. Immunology, 74: 55-59, 1991.*
Chapman, 2002, "PEGylated Antibodies and Antibody Fragments for Improved Therapy: A Review," *Advanced Drug Delivery Reviews* 54(4):531-545.
Petkova et al, 2006, "Enhanced half-life of genetically engineered human IgG1 antibodies in a humanized FcRn mouse model: potential application in humorally mediated autoimmune disease," *International Immunology* 18(12):1759-1769.
Jiang et al., 2007, "Expression of Gastrin Receptor in Tumors and its Application as a Molecular Target for Cancer Diagnosis and Therapy," *World Chinese Journal of Digestology* 15(9):980-985.
Reubi et al., 1997, "Cholecystokinin(CCK)-A and CCK-B/Gastrin Receptors in Human Tumors," *Cancer Research* 57(7):1377-1386.
Partial International Search Report from related International Application No. PCT/EP2011/000048 dated Mar. 15, 2011.
Duffy, M.J., 2001, "Biochemical markers in Breast Cancer: which ones are clinically useful?" *Clin Biochem* 34(5): 347-352.
Gupta et al., 2009, "Identification of Selective Inhibitors of Cancer Stem Cells by High-Throughput Screening," *Cell*, 138(4): 645-659.
International Search Report and Written Opinion from related International Application No. PCT/EP2011/000048 dated Aug. 10, 2011.

* cited by examiner

*Primary Examiner* — Misook Yu
*Assistant Examiner* — Anne Holleran
(74) *Attorney, Agent, or Firm* — Dechert LLP

(57) ABSTRACT

The present disclosure is directed to methods of treating and preventing breast cancer or recurrence of breast cancer with compositions comprising anti-progastrin antibodies.

33 Claims, 51 Drawing Sheets

Figure 1:
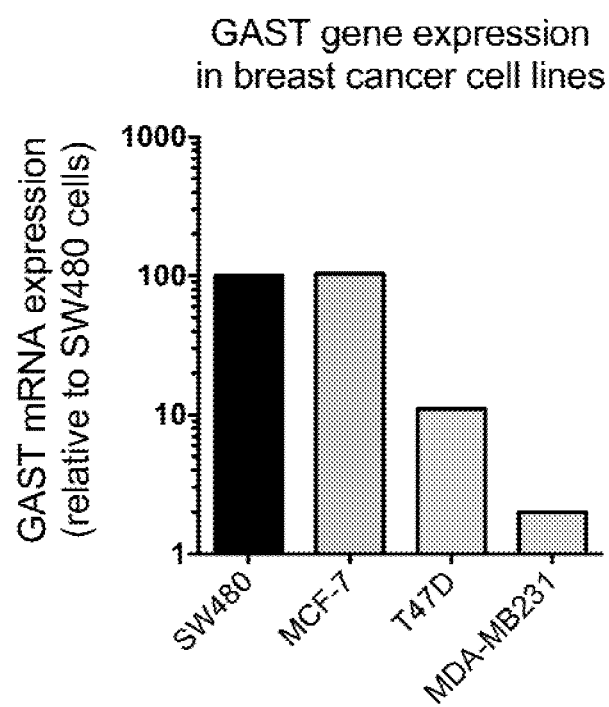

Expression of the progastrin-encoding gene in spheres from 3D cell lines

FIG. 13

```
Preprogastrin:   M QRLCVYVLIF ALALAAFSEA SWKPRSQQPD APLGTGANRD LELPWLEQQG
SEQ ID NO:100   -21          -11         -1 +1        11         21

PASHHRRQLG  PQGPPHLVAD  PSKKQGPWLE EEEEAYGWMD FGRRSAEDEN
                 31          41          51         61         71

Progastrin:
                                         SWKPRSQQPD APLGTGANRD LELPWLEQQG
SEQ ID NO:101                            +1         11         21

PASHHRRQLG  PQGPPHLVAD  PSKKQGPWLE EEEEAYGWMD FGRRSAEDEN
                 31          41          51         61         71

G34:                 QLG     PQGPPHLVAD  PSKKQGPWLE EEEEAYGWMD F-NH₂
SEQ ID NO:102        41                  51         61         71

G34-Gly:             QLG     PQGPPHLVAD  PSKKQGPWLE EEEEAYGWMD FG
SEQ ID NO:103        41                  51         61         71

G17:                                     QGPWLE     EEEEAYGWMD F-NH₂
SEQ ID NO:104                            51         61         71

G17-Gly:                                 QGPWLE     EEEEAYGWMD FG
SEQ ID NO:105                            51         61         71

CTFP:                                                          SAEDEN
SEQ ID NO:106                                                  75
```

FIG. 14A mV$_H$ MAb3

| | | | | | | | | | | | | | | | | |
|---|---|---|---|---|---|---|---|---|---|---|---|---|---|---|---|---|
| gag | gtt | cag | ctc | cag | cag | tct | ggg | act | gtg | ctg | gca | agg | cct | ggg | gct | 48 |
| Glu | Val | Gln | Leu | Gln | Gln | Ser | Gly | Thr | Val | Leu | Ala | Arg | Pro | Gly | Ala | |
| 1 | | | | 5 | | | | | 10 | | | | | 15 | | |

| tcc | gtg | aag | atg | tcc | tgc | aag | gct | tct | ggc | tac | atc | ttt | acc | agc | tac | 96 |
|---|---|---|---|---|---|---|---|---|---|---|---|---|---|---|---|---|
| Ser | Val | Lys | Met | Ser | Cys | Lys | Ala | Ser | Gly | Tyr | Ile | Phe | Thr | Ser | Tyr | |
| | | | 20 | | | | | 25 | | | | | 30 | | | |

| tgg | gta | cac | tgg | gtt | aaa | cag | agg | cct | gga | cag | ggt | cta | gaa | tgg | att | 144 |
|---|---|---|---|---|---|---|---|---|---|---|---|---|---|---|---|---|
| Trp | Val | His | Trp | Val | Lys | Gln | Arg | Pro | Gly | Gln | Gly | Leu | Glu | Trp | Ile | |
| | | 35 | | | | | 40 | | | | | 45 | | | | |

| ggt | ggt | ttt | tat | cct | gga | aat | agt | gat | tct | agg | tac | aac | cag | aaa | ttc | 192 |
|---|---|---|---|---|---|---|---|---|---|---|---|---|---|---|---|---|
| Gly | Gly | Phe | Tyr | Pro | Gly | Asn | Ser | Asp | Ser | Arg | Tyr | Asn | Gln | Lys | Phe | |
| | 50 | | | | | 55 | | | | | 60 | | | | | |

| aag | ggc | aag | gcc | aca | ctg | act | gca | gtc | aca | tcc | gcc | agt | act | gcc | tac | 240 |
|---|---|---|---|---|---|---|---|---|---|---|---|---|---|---|---|---|
| Lys | Gly | Lys | Ala | Thr | Leu | Thr | Ala | Val | Thr | Ser | Ala | Ser | Thr | Ala | Tyr | |
| 65 | | | | | 70 | | | | | 75 | | | | | 80 | |

| atg | gac | ctc | agc | agc | ctg | aca | aat | gag | gac | tct | gcg | gtc | tat | ttc | tgt | 288 |
|---|---|---|---|---|---|---|---|---|---|---|---|---|---|---|---|---|
| Met | Asp | Leu | Ser | Ser | Leu | Thr | Asn | Glu | Asp | Ser | Ala | Val | Tyr | Phe | Cys | |
| | | | | 85 | | | | | 90 | | | | | 95 | | |

| aca | aga | aga | gat | agt | ccc | cag | tac | tgg | ggc | caa | ggc | acc | act | ctc | aca | 336 |
|---|---|---|---|---|---|---|---|---|---|---|---|---|---|---|---|---|
| Thr | Arg | Arg | Asp | Ser | Pro | Gln | Tyr | Trp | Gly | Gln | Gly | Thr | Thr | Leu | Thr | |
| | | | | 100 | | | | 105 | | | | | 110 | | | |

| gtc | tcc | tca | | | | | | | | | | | | | | 345 |
|---|---|---|---|---|---|---|---|---|---|---|---|---|---|---|---|---|
| Val | Ser | Ser | | | | | | | | | | | | | | |
| | | 115 | | | | | | | | | | | | | | |

FIG. 14B mV$_L$ MAb3

| | | | | | | | | | | | | | | | | |
|---|---|---|---|---|---|---|---|---|---|---|---|---|---|---|---|---|
| gat | gtt | ttg | atg | acc | caa | act | cca | ctc | tcc | ctg | cct | gtc | agt | ctt | gga | 48 |
| Asp | Val | Leu | Met | Thr | Gln | Thr | Pro | Leu | Ser | Leu | Pro | Val | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gat | caa | gcc | tcc | atc | tct | tgc | aga | tct | agt | cag | agc | att | gta | cat | agt | 96 |
| Asp | Gln | Ala | Ser | Ile | Ser | Cys | Arg | Ser | Ser | Gln | Ser | Ile | Val | His | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| aat | gga | aac | acc | tat | tta | gaa | tgg | tac | ctg | cag | aaa | cca | ggc | cag | tct | 144 |
| Asn | Gly | Asn | Thr | Tyr | Leu | Glu | Trp | Tyr | Leu | Gln | Lys | Pro | Gly | Gln | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | aag | ctc | ctg | atc | tac | aaa | gtt | tcc | aac | cga | ttt | tct | ggg | gtc | cca | 192 |
| Pro | Lys | Leu | Leu | Ile | Tyr | Lys | Val | Ser | Asn | Arg | Phe | Ser | Gly | Val | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| gac | agg | ttc | agt | ggc | agt | gga | tca | ggg | aca | gat | ttc | aca | ctc | aag | atc | 240 |
| Asp | Arg | Phe | Ser | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | ctg | gag | gct | gag | gat | ctg | gga | gtt | tat | tac | tgc | ttt | caa | ggt | 288 |
| Ser | Arg | Leu | Glu | Ala | Glu | Asp | Leu | Gly | Val | Tyr | Tyr | Cys | Phe | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| tca | cat | gtt | ccg | ttc | acg | ttc | gga | ggg | ggg | acc | aag | ctg | gaa | ata | aaa | 336 |
| Ser | His | Val | Pro | Phe | Thr | Phe | Gly | Gly | Gly | Thr | Lys | Leu | Glu | Ile | Lys | |
| | | | 100 | | | | | 105 | | | | | 110 | | | |

FIG. 14C mV$_H$ MAb4

```
cag gtt cag ttg cag cag tct gga gct gag ctg atg aag cca ggg gcc   48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc   96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
                35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
            50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
                100                 105                 110 ctg gtc act gtc tct gca                                           354
Leu Val Thr Val Ser Ala
            115
```

FIG. 14D mV$_L$ MAb4

```
gat ctt gtg atg acc caa act cca ctc tcc ctg cct gtc agt ctt gga   48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt   96
Asp Gln Ala Ser Ile Ser Cys Arg Ser Ser Gln Ser Leu Val His Ser
                20                  25                  30 agt gga gtc acc tat tta cat tgg tac ctg cag aag cca ggc cag tct  144
Ser Gly Val Thr Tyr Leu His Trp Tyr Leu Gln Lys Pro Gly Gln Ser
                35                  40                  45 cca aag ctc ctg atc tac aaa gtt tcc aac cga ttt tct ggg gtc cca  192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc  240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt  288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa  336
Thr His Val Pro Pro Thr Phe Gly Ser Gly Thr Lys Leu Glu Ile Lys
                100                 105                 110
```

FIG. 14E mV$_H$ MAb8

```
gaa gtg cag ctg gtg gag tct ggg gga ggc tta gtg aag cct gga ggg    48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat    96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc   144
Ala Met Ser Trp Val Arg Gln Thr Pro Glu Lys Arg Leu Glu Trp Val
        35                  40                  45 gca acc att agt agt ggt ggt act tac acc tac tat cca gac agt gtg   192
Ala Thr Ile Ser Ser Gly Gly Thr Tyr Thr Tyr Tyr Pro Asp Ser Val
        50                  55                  60 aag ggt cga ttc acc atc tcc aga gac aat gcc aag aac gcc cta tac   240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt   288
Leu Gln Met Ser Ser Leu Arg Ser Glu Asp Thr Ala Met Tyr Tyr Cys
                85                  90                  95 gca aca cag ggg aat tac tct ttg gac ttc tgg ggc caa ggc acc tct   336
Ala Thr Gln Gly Asn Tyr Ser Leu Asp Phe Trp Gly Gln Gly Thr Ser
                100                 105                 110 ctc aca gtc tcc tca                                                351
Leu Thr Val Ser Ser
        115
```

FIG. 14F mV$_L$ MAb8

| | | | | | | | | | | | | | | | |
|---|---|---|---|---|---|---|---|---|---|---|---|---|---|---|---|
| gac | att | gtg | atg | acg | cag | gct | gca | tcc | tct | aat | cca | gtc | act | ctt | gga | 48 |
| Asp | Ile | Val | Met | Thr | Gln | Ala | Ala | Ser | Ser | Asn | Pro | Val | Thr | Leu | Gly |
| 1 | | | | 5 | | | | | 10 | | | | | 15 | |

| aca | tcc | gct | tcc | atc | tcc | tgc | agg | tct | agt | aag | agt | ctc | cga | cat | act | 96 |
|---|---|---|---|---|---|---|---|---|---|---|---|---|---|---|---|---|
| Thr | Ser | Ala | Ser | Ile | Ser | Cys | Arg | Ser | Ser | Lys | Ser | Leu | Arg | His | Thr |
| | | | | 20 | | | | | 25 | | | | | 30 | |

| aaa | ggc | atc | act | ttt | ttg | tat | tgg | tat | ctg | cag | aag | cca | ggc | cag | tct | 144 |
|---|---|---|---|---|---|---|---|---|---|---|---|---|---|---|---|---|
| Lys | Gly | Ile | Thr | Phe | Leu | Tyr | Trp | Tyr | Leu | Gln | Lys | Pro | Gly | Gln | Ser |
| | | | 35 | | | | | 40 | | | | | 45 | | |

| cct | cag | ctc | ctg | att | tat | cag | atg | tcc | aac | ctt | gcc | tca | gga | gtc | cca | 192 |
|---|---|---|---|---|---|---|---|---|---|---|---|---|---|---|---|---|
| Pro | Gln | Leu | Leu | Ile | Tyr | Gln | Met | Ser | Asn | Leu | Ala | Ser | Gly | Val | Pro |
| | 50 | | | | | | 55 | | | | | 60 | | | |

| gac | agg | ttc | agt | agc | agt | ggg | tca | gga | act | gat | ttc | aca | ctg | aga | atc | 240 |
|---|---|---|---|---|---|---|---|---|---|---|---|---|---|---|---|---|
| Asp | Arg | Phe | Ser | Ser | Ser | Gly | Ser | Gly | Thr | Asp | Phe | Thr | Leu | Arg | Ile |
| 65 | | | | | 70 | | | | | 75 | | | | | 80 |

| agc | aga | gtg | gag | gct | gag | gat | ttg | ggt | gtt | tat | tac | tgt | gct | caa | aat | 288 |
|---|---|---|---|---|---|---|---|---|---|---|---|---|---|---|---|---|
| Ser | Arg | Val | Glu | Ala | Glu | Asp | Leu | Gly | Val | Tyr | Tyr | Cys | Ala | Gln | Asn |
| | | | | 85 | | | | | 90 | | | | | 95 | |

| cta | gaa | ctt | ccg | ctc | acg | ttc | ggt | gct | ggg | acc | aag | ctg | gag | ctg | aaa | 336 |
|---|---|---|---|---|---|---|---|---|---|---|---|---|---|---|---|---|
| Leu | Glu | Leu | Pro | Leu | Thr | Phe | Gly | Ala | Gly | Thr | Lys | Leu | Glu | Leu | Lys |
| | | | 100 | | | | | 105 | | | | | 110 | | |

FIG. 14G mV$_H$ MAb13

| | | | | | | | | | | | | | | | | |
|---|---|---|---|---|---|---|---|---|---|---|---|---|---|---|---|---|
| gag | gtg | cag | ctg | gtg | gag | tct | ggg | gga | ggc | ttg | gtg | cag | cct | gga | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | att | ttc | agt | agc | tat | 96 |
| Ser | Leu | Lys | Leu | Ser | Cys | Ala | Ala | Ser | Gly | Phe | Ile | Phe | Ser | Ser | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| ggc | atg | tct | tgg | gtt | cgc | cag | tct | cca | gac | agg | agg | ctg | gag | ttg | gtc | 144 |
| Gly | Met | Ser | Trp | Val | Arg | Gln | Ser | Pro | Asp | Arg | Arg | Leu | Glu | Leu | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | agt | att | aat | act | ttt | ggt | gat | aga | acc | tat | tat | cca | gac | agt | gtg | 192 |
| Ala | Ser | Ile | Asn | Thr | Phe | Gly | Asp | Arg | Thr | Tyr | Tyr | Pro | Asp | Ser | Val | |
| | | 50 | | | | | 55 | | | | | 60 | | | | |

| | | | | | | | | | | | | | | | | |
|---|---|---|---|---|---|---|---|---|---|---|---|---|---|---|---|---|
| aag | ggc | cga | ttc | acc | atc | tcc | aga | gac | aat | gcc | aag | aac | acc | ctg | tac | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | acc | agt | ctg | aag | tct | gag | gac | aca | gcc | att | tat | tac | tgt | 288 |
| Leu | Gln | Met | Thr | Ser | Leu | Lys | Ser | Glu | Asp | Thr | Ala | Ile | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aga | ggg | acc | gga | acc | tac | tgg | ggc | caa | ggc | acc | act | ctc | aca | gtc | 336 |
| Ala | Arg | Gly | Thr | Gly | Thr | Tyr | Trp | Gly | Gln | Gly | Thr | Thr | Leu | Thr | Val | |
| | | | 100 | | | | | 105 | | | | | 110 | | | |

| | | |
|---|---|---|
| tcc | tca | 342 |
| Ser | Ser | |

FIG. 14H mV$_L$ MAb13

```
gat gtt gtg ctg acc cag act cca ctc act ttg tcg gtt acc att gga    48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt    96
Gln Pro Ala Ser Ile Ser Cys Lys Ser Ser Gln Ser Leu Leu Asp Ser
                20                  25                  30 gat gga aag aca tat ttg aat tgg ttg tta cag agg cca ggc cag tct   144
Asp Gly Lys Thr Tyr Leu Asn Trp Leu Leu Gln Arg Pro Gly Gln Ser
            35                  40                  45 cca aag cgc cta atc tat ctg gtg tct aaa ctg gac tct gga gtc cct   192
Pro Lys Arg Leu Ile Tyr Leu Val Ser Lys Leu Asp Ser Gly Val Pro
        50                  55                  60 gac agg ttc act ggc agt gga tca ggg aca gat ttc aca ctg aaa atc   240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt   288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa   336
Thr His Phe Pro Gln Thr Phe Gly Gly Gly Thr Lys Leu Glu Ile Lys
            100                 105                 110
```

FIG. 14I mV$_H$ MAb16

```
cag gtc caa ctg cag cag tct ggg gct gaa ctg gtg aag cct ggg gct    48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac    96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att   144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc   192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac   240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt   288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act   336
Thr Arg Gly Gly Tyr Tyr Pro Phe Asp Tyr Trp Gly Gln Gly Thr Thr
            100                 105                 110 ctc aca gtc tcc tca                                                351
Leu Thr Val Ser Ser
            115
```

FIG. 14J mV$_L$ MAb16

| | | | | | | | | | | | | | | | | |
|---|---|---|---|---|---|---|---|---|---|---|---|---|---|---|---|---|
| gat | gtt | gtg | atg | acc | cag | act | cca | ctc | act | ttg | tcg | gtt | acc | att | ggg | 48 |
| Asp | Val | Val | Met | Thr | Gln | Thr | Pro | Leu | Thr | Leu | Ser | Val | Thr | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgc | cca | gcc | tcc | atc | tct | tgc | aag | tca | agt | cag | agc | ctc | tta | gac | agt | 96 |
| Arg | Pro | Ala | Ser | Ile | Ser | Cys | Lys | Ser | Ser | Gln | Ser | Leu | Leu | Asp | Ser | |
| | | | | 20 | | | | | 25 | | | | | 30 | | |

| | | | | | | | | | | | | | | | | |
|---|---|---|---|---|---|---|---|---|---|---|---|---|---|---|---|---|
| gat | gga | aag | aca | tat | ttg | tat | tgg | ttg | tta | cag | agg | cca | ggc | cag | tct | 144 |
| Asp | Gly | Lys | Thr | Tyr | Leu | Tyr | Trp | Leu | Leu | Gln | Arg | Pro | Gly | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | aag | cgc | cta | atc | tat | ctg | gtg | tct | gag | ctg | gac | tct | gga | gtc | cct | 192 |
| Pro | Lys | Arg | Leu | Ile | Tyr | Leu | Val | Ser | Glu | Leu | Asp | Ser | Gly | Val | Pro | |
| | 50 | | | | | | 55 | | | | | 60 | | | | |

| | | | | | | | | | | | | | | | | |
|---|---|---|---|---|---|---|---|---|---|---|---|---|---|---|---|---|
| gac | agg | atc | act | ggc | agt | ggg | tcg | ggg | aca | gat | ttc | aca | ctg | aag | atc | 240 |
| Asp | Arg | Ile | Thr | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | ttg | gga | gtt | tat | tat | tgc | tgg | caa | gga | 288 |
| Ser | Arg | Val | Glu | Ala | Glu | Asp | Leu | Gly | Val | Tyr | Tyr | Cys | Trp | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | cat | tct | ccg | tac | acg | ttc | gga | ggg | ggg | acc | aag | ctg | gaa | ata | aaa | 336 |
| Thr | His | Ser | Pro | Tyr | Thr | Phe | Gly | Gly | Gly | Thr | Lys | Leu | Glu | Ile | Lys | |
| | | | 100 | | | | | 105 | | | | | 110 | | | |

FIG. 14K mV$_H$ MAb19

```
gat gtg cag ctt cag gag tcg gga cct ggc ctg gtg aaa cct tct cag    48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat    96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg   144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc   192
Met Gly Tyr Ile Ser Phe Ser Gly Tyr Thr Ser Tyr Asn Pro Ser Leu
        50              55                  60 aaa agt cga atc tct gtc act cgg gac aca tcc agg aac caa ttc ttc   240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt   288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc   336
Ala Arg Glu Val Asn Tyr Gly Asp Ser Tyr His Phe Asp Tyr Trp Gly
                100                 105                 110 caa ggc acc att gtc aca gtc tcc tca                               363
Gln Gly Thr Ile Val Thr Val Ser Ser
        115                 120
```

FIG. 14L mV$_L$ MAb19

```
caa ctt gcg ctc act cag tca tct tca gcc tct ttc tcc ctg gga gcc     48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc     96
Ser Ala Lys Leu Thr Cys Thr Leu Ser Ser Gln His Arg Thr Tyr Thr
                20                  25                  30 att gaa tgg tat cag caa cag tca ctc aag cct cct aag tat gtg atg    144
Ile Glu Trp Tyr Gln Gln Gln Ser Leu Lys Pro Pro Lys Tyr Val Met
            35                  40                  45 gag gtt aag aaa gat gga agc cac agc aca ggt cat ggg att cct gat    192
Glu Val Lys Lys Asp Gly Ser His Ser Thr Gly His Gly Ile Pro Asp
        50                  55                  60 cgc ttc tct gga tcc agt tct ggt gct gat cgc tac ctc agc att tcc    240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat    288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc    336
Ala Ile Lys Gly Gln Ser Val Phe Val Phe Gly Gly Gly Thr Lys Val
                100                 105                 110 act gtc cta                                                         345
Thr Val Leu
        115
```

FIG. 15A hV$_H$ MAb3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
    115

FIG. 15B hV$_L$ MAb3

```
Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Ile Val His Ser
            20                  25              30

Asn Gly Asn Thr Tyr Leu Glu Trp Phe Gln Gln Arg Pro Gly Gln Ser
            35                  40              45

Pro Arg Arg Leu Ile Tyr Lys Val Ser Asn Arg Phe Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110
```

FIG. 15C hV$_H$ MAb4

Gln Val Gln Leu Val Gln Ser Gly Ala Glu Val Lys Lys Pro Gly Ala
1           5                   10                  15

Ser Val Lys Val Ser Cys Lys Ala Ser Gly Tyr Thr Phe Ser Ser Ser
              20                  25                  30

Trp Met His Trp Val Arg Gln Ala Pro Gly Gln Gly Leu Glu Trp Met
              35                  40                  45

Gly Ile Phe Leu Pro Gly Ser Gly Ser Thr Asp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
              85                  90                  95

Ala Thr Asp Gly Asn Tyr Asp Trp Phe Ala Tyr Trp Gly Gln Gly Thr
              100                 105                 110

Leu Val Thr Val Ser Ser
        115

FIG. 15D hV<sub>L</sub> MAb4

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

FIG. 15E hV$_H$ MAb8(a)

Glu Val Gln Leu Val Glu Ser Gly Gly Gly Leu Val Lys Pro Gly Gly
1           5              10                 15

Ser Leu Arg Leu Ser Cys Ala Ala Ser Gly Phe Thr Phe Thr Thr Tyr
         20              25              30

Ala Met Ser Trp Val Arg Gln Ala Pro Gly Lys Gly Leu Glu Trp Val
         35              40              45

Ser Ser Ile Ser Ser Gly Gly Thr Tyr Thr Tyr Tyr Ala Asp Ser Val
       50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
              85              90              95

Ala Thr Gln Gly Asn Tyr Ser Leu Asp Phe Trp Gly Gln Gly Thr Thr
              100             105             110

Val Thr Val Ser Ser
         115

FIG. 15F hV$_L$ MAb8(a)

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
            50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Leu Thr Phe Gly Gly Gly Thr Lys Val Glu Ile Lys
            100                 105                 110

FIG. 15G hV$_H$ MAb8(b)

Glu Val Gln Leu Val Glu Ser Gly Gly Leu Val Lys Pro Gly Gly
1           5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

Ala Thr Gln Gly Asn Tyr Ser Leu Asp Phe Trp Gly Gln Gly Thr Thr
                100                 105                 110

Val Thr Val Ser Ser
        115

FIG. 15H hV$_L$ MAb8(b)

Asp Ile Val Met Thr Gln Ser Pro Leu Ser Leu Pro Val Thr Pro Gly
1            5                    10                  15

Glu Pro Ala Ser Ile Ser Cys Arg Ser Ser Lys Ser Leu Arg His Thr
             20                  25                  30

Lys Gly Ile Thr Phe Leu Asp Trp Tyr Leu Gln Lys Pro Gly Gln Ser
             35                  40                  45

Pro Gln Leu Leu Ile Tyr Gln Met Ser Asn Arg Ala Ser Gly Val Pro
             50              55                  60

Asp Arg Phe Ser Gly Ser Gly Ser Gly Thr Asp Phe Thr Leu Lys Ile
65                   70                  75                  80

Ser Arg Val Glu Ala Glu Asp Val Gly Val Tyr Tyr Cys Ala Gln Asn
                 85                  90                  95

Leu Glu Leu Pro Leu Thr Phe Gly Gly Gly Thr Lys Val Glu Ile Lys
             100                 105                 110

FIG. 15I hV_H MAb8(c)

Glu Val Gln Leu Val Glu Ser Gly Gly Leu Val Lys Pro Gly Gly
1             5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
            35                  40                  45

Ser Thr Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

FIG. 15J hV$_L$ MAb8(c)

Asp Ile Val Met Thr Gln Ser Pro Leu Ser Leu Pro Val Thr Pro Gly
1             5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
            85                  90                  95

Leu Glu Leu Pro Leu Thr Phe Gly Gly Gly Thr Lys Val Glu Ile Lys
            100                 105                 110

FIG. 15K hV_H MAb13(a)

Glu Val Gln Leu Val Glu Ser Gly Gly Gly Leu Val Gln Pro Gly Gly
1              5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
            35                  40                  45

Ala Asn Ile Asn Thr Phe Gly Asp Arg Thr Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Thr Gly Thr Tyr Trp Gly Gln Gly Thr Leu Val Thr Val
            100                 105                 110

Ser Ser

FIG. 15L hV$_L$ MAb13(a)

Asp Val Val Met Thr Gln Ser Pro Leu Ser Leu Pro Val Thr Leu Gly
1              5                   10                  15

Gln Pro Ala Ser Ile Ser Cys Arg Ser Ser Gln Ser Leu Leu Asp Ser
             20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Phe Pro Gln Thr Phe Gly Gly Gly Thr Lys Val Glu Ile Lys
            100                 105                 110

FIG. 15M hV$_H$ MAb13(b)

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
                100                 105                 110

Ser Ser

FIG. 15N hV$_L$ MAb13(b)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

FIG. 15O hV_H MAb16(a)

Gln Val Gln Leu Val Gln Ser Gly Ala Glu Val Lys Lys Pro Gly Ala
1               5                   10                  15

Ser Val Lys Val Ser Cys Lys Ala Ser <u>Gly Tyr Thr Phe Thr Ser Tyr</u>
                20                  25                  30

<u>Tyr</u> Met Tyr Trp Val Arg Gln Ala Pro Gly Gln Gly Leu Glu Trp Met
            35                  40                  45

Gly Ile <u>Ile Asn Pro Ser Asn Gly Gly Thr</u> Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<u>Thr Arg Gly Gly Tyr Tyr Pro Phe Asp Tyr</u> Trp Gly Gln Gly Thr Thr
            100                 105                 110

Val Thr Val Ser Ser
        115

FIG. 15P hV_L MAb16(a)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

FIG. 15Q hV$_H$ MAb16(b)

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
        50                  55                  60

Gln Gly Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

FIG. 15R hV$_L$ MAb16(b)

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 15S hV$_H$ MAb16(c)

Gln Val Gln Leu Val Gln Ser Gly Ala Glu Val Lys Lys Pro Gly Ala
1              5                   10                  15

Ser Val Lys Val Ser Cys Lys Ala Ser Gly Tyr Thr Phe Thr Ser Tyr
              20                  25                  30

Tyr Met Tyr Trp Val Arg Gln Ala Pro Gly Gln Gly Leu Glu Trp Met
          35                  40                  45

Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
              85                  90                  95

Thr Arg Gly Gly Tyr Tyr Pro Phe Asp Tyr Trp Gly Gln Gly Thr Thr
              100                 105                 110

Val Thr Val Ser Ser
              115

FIG. 15T hV$_L$ MAb16(c)

Asp Val Val Met Thr Gln Ser Pro Leu Ser Leu Pro Val Thr Leu Gly
1             5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Glu Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 15U hV$_H$ MAb19(a)

Gln Val Gln Leu Gln Glu Ser Gly Pro Gly Leu Val Lys Pro Ser Gln
1               5               10                  15

Thr Leu Ser Leu Thr Cys Thr Val Ser Gly Tyr Ser Ile Thr Ser Asp
            20              25                  30

Tyr Ala Trp Asn Trp Ile Arg Gln His Pro Gly Lys Gly Leu Glu Trp
        35              40              45

Ile Gly Tyr Ile Ser Phe Ser Gly Tyr Thr Tyr Tyr Asn Pro Ser Leu
        50              55              60

Lys Ser Arg Val Thr Ile Ser Val Asp Thr Ser Lys Asn Gln Phe Ser
65              70              75              80

Leu Lys Leu Ser Ser Val Thr Ala Ala Asp Thr Ala Val Tyr Tyr Cys
            85              90              95

Ala Arg Glu Val Asn Tyr Gly Asp Ser Tyr His Phe Asp Tyr Trp Gly
            100             105             110

Gln Gly Thr Leu Val Thr Val Ser Ser
        115             120

FIG. 15V hV_L MAb19(a)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
                35                  40                  45

Lys Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65              70                  75                          80

Ser Leu Gln Ser Glu Asp Glu Ala Asp Tyr Tyr Cys Gly Val Gly Asp
                    85                  90                  95

Ala Ile Lys Gly Gln Ser Val Phe Val Phe Gly Gly Gly Thr Lys Val
                100                 105                 110

Glu Ile Lys
        115
```

FIG. 15W hV$_H$ MAb19(b)

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
            35                  40                  45

Ile Gly Tyr Ile Ser Phe Ser Gly Tyr Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

FIG. 15X hV$_L$ MAb19(b)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65              70                  75                      80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

FIG. 15Y hV$_H$ MAb19(c)

Gln Val Gln Leu Gln Glu Ser Gly Pro Gly Leu Val Lys Pro Ser Gln
1             5                     10                    15

Thr Leu Ser Leu Thr Cys Thr Val Ser Gly Tyr Ser Ile Thr Ser Asp
            20                  25                    30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

FIG. 15Z hV$_L$ MAb19(c)

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65              70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
    115

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
50                  55                  60

Lys Gly Lys Ala Thr Phe Thr Ala Asp Thr Ser Ser Asp Thr Ala Tyr
65                  70                  75                  80

Met Leu Leu Ser Ser Leu Thr Ser Glu Asp Ser Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

```
Ser Gly Val Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Ser Gly Thr Lys Leu Glu Ile Lys
            100                 105                 110
```

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 16

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
 1               5                  10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
             20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
         35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
     50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
 65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                 85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
            100                 105                 110 gtc tcc tca                                                         345
Val Ser Ser
        115
```

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
 1               5                  10                  15
```

```
gat caa gcc tcc atc tct tgc aga tct agt cag agc att gta cat agt         96
Asp Gln Ala Ser Ile Ser Cys Arg Ser Ser Gln Ser Ile Val His Ser
             20                  25                  30 aat gga aac acc tat tta gaa tgg tac ctg cag aaa cca ggc cag tct        144
Asn Gly Asn Thr Tyr Leu Glu Trp Tyr Leu Gln Lys Pro Gly Gln Ser
         35                  40                  45 cca aag ctc ctg atc tac aaa gtt tcc aac cga ttt tct ggg gtc cca        192
Pro Lys Leu Leu Ile Tyr Lys Val Ser Asn Arg Phe Ser Gly Val Pro
     50                  55                  60 gac agg ttc agt ggc agt gga tca ggg aca gat ttc aca ctc aag atc        240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt        288
Ser Arg Leu Glu Ala Glu Asp Leu Gly Val Tyr Tyr Cys Phe Gln Gly
                 85                  90                  95 tca cat gtt ccg ttc acg ttc gga ggg ggg acc aag ctg gaa ata aaa        336
Ser His Val Pro Phe Thr Phe Gly Gly Gly Thr Lys Leu Glu Ile Lys
            100                 105                 110

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 18 cag gtt cag ttg cag cag tct gga gct gag ctg atg aag cca ggg gcc         48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc         96
Ser Val Lys Ile Ser Cys Lys Ala Thr Gly Tyr Thr Phe Ser Ser Ser
             20                  25                  30 tgg ata gag tgg tta aaa cag agg cct gga cat ggc ctt gag tgg att        144
Trp Ile Glu Trp Leu Lys Gln Arg Pro Gly His Gly Leu Glu Trp Ile
         35                  40                  45 gga gag ttt tta cct gga agt ggt agt aca gac tac aat gag aag ttc        192
Gly Glu Phe Leu Pro Gly Ser Gly Ser Thr Asp Tyr Asn Glu Lys Phe
     50                  55                  60 aag ggc aag gcc aca ttc act gca gac aca tcc tcc gac aca gcc tac        240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt        288
Met Leu Leu Ser Ser Leu Thr Ser Glu Asp Ser Ala Val Tyr Tyr Cys
                 85                  90                  95 gca act gat ggt aat tat gac tgg ttt gct tac tgg ggc caa ggg act        336
Ala Thr Asp Gly Asn Tyr Asp Trp Phe Ala Tyr Trp Gly Gln Gly Thr
            100                 105                 110 ctg gtc act gtc tct gca                                                354
Leu Val Thr Val Ser Ala
            115

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: CDS
<222> LOCATION: (1)..(336)

<400> SEQUENCE: 19 gat ctt gtg atg acc caa act cca ctc tcc ctg cct gtc agt ctt gga      48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt      96
Asp Gln Ala Ser Ile Ser Cys Arg Ser Ser Gln Ser Leu Val His Ser
            20                  25                  30 agt gga gtc acc tat tta cat tgg tac ctg cag aag cca ggc cag tct     144
Ser Gly Val Thr Tyr Leu His Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt     288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa     336
Thr His Val Pro Pro Thr Phe Gly Ser Gly Thr Lys Leu Glu Ile Lys
            100                 105                 110

<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60
```

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15

<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 28
<211> LENGTH: 5
<212> TYPE: PRT

<213> ORGANISM: Homo sapiens

<400> SEQUENCE: 28

Asp Ala Pro Leu Gly
1               5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
1

<210> SEQ ID NO 34
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens

```
<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Gln Gly Asn Tyr Ser Leu Asp Phe
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5

<210> SEQ ID NO 47

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Gly Gly Tyr Tyr Pro Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Glu Val Asn Tyr Gly Asp Ser Tyr His Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Arg His Thr Lys Gly Ile Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Leu Leu Asp Ser Asp Gly Lys Thr Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

```
Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gly Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Ser Glu Asp Thr Ala Ile Tyr Tyr Cys
                85                  90                  95

Ala Arg Gly Thr Gly Thr Tyr Trp Gly Gln Gly Thr Thr Leu Thr Val
            100                 105                 110

Ser Ser

<210> SEQ ID NO 61
```

<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Tyr Tyr Pro Phe Asp Tyr Trp Gly Gln Gly Thr Thr
            100                 105                 110

Leu Thr Val Ser Ser
        115
```

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120
```

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
Asp Ile Val Met Thr Gln Ala Ala Ser Ser Asn Pro Val Thr Leu Gly
1               5                   10                  15

Thr Ser Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
65                  70                  75                  80

Ser Arg Val Glu Ala Glu Asp Leu Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
            35                  40                  45

Pro Lys Arg Leu Ile Tyr Leu Val Ser Glu Leu Asp Ser Gly Val Pro
        50                  55                  60

Asp Arg Ile Thr Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Trp Gln Gly
            85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Ser Leu Lys Pro Pro Lys Tyr Val Met
        35                  40                  45

Glu Val Lys Lys Asp Gly Ser His Ser Thr Gly His Gly Ile Pro Asp
50                  55                  60

Arg Phe Ser Gly Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
            85                  90                  95

Ala Ile Lys Gly Gln Ser Val Phe Val Phe Gly Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg   48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat   96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc  144
Ala Met Ser Trp Val Arg Gln Thr Pro Glu Lys Arg Leu Glu Trp Val
        35                  40                  45 gca acc att agt agt ggt ggt act tac acc tac tat cca gac agt gtg  192
Ala Thr Ile Ser Ser Gly Gly Thr Tyr Thr Tyr Tyr Pro Asp Ser Val
    50                  55                  60 aag ggt cga ttc acc atc tcc aga gac aat gcc aag aac gcc tta tac  240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt  288
Leu Gln Met Ser Ser Leu Arg Ser Glu Asp Thr Ala Met Tyr Tyr Cys
            85                  90                  95
```

| gca aca cag ggg aat tac tct ttg gac ttc tgg ggc caa ggc acc tct | 336 |
|---|---|
| Ala Thr Gln Gly Asn Tyr Ser Leu Asp Phe Trp Gly Gln Gly Thr Ser | |
| 100 105 110 | |

| ctc aca gtc tcc tca | 351 |
|---|---|
| Leu Thr Val Ser Ser | |
| 115 | |

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68

| gag gtg cag ctg gtg gag tct ggg gga ggc ttg gtg cag cct gga ggg | 48 |
|---|---|
| Glu Val Gln Leu Val Glu Ser Gly Gly Gly Leu Val Gln Pro Gly Gly | |
| 1               5                   10                  15 | |

| tcc ctg aaa ctc tcc tgt gca gcc tct gga ttc att ttc agt agc tat | 96 |
|---|---|
| Ser Leu Lys Leu Ser Cys Ala Ala Ser Gly Phe Ile Phe Ser Ser Tyr | |
|         20                  25                  30 | |

| ggc atg tct tgg gtt cgc cag tct cca gac agg agg ctg gag ttg gtc | 144 |
|---|---|
| Gly Met Ser Trp Val Arg Gln Ser Pro Asp Arg Arg Leu Glu Leu Val | |
|     35                  40                  45 | |

| gca agt att aat act ttt ggt gat aga acc tat tat cca gac agt gtg | 192 |
|---|---|
| Ala Ser Ile Asn Thr Phe Gly Asp Arg Thr Tyr Tyr Pro Asp Ser Val | |
| 50                  55                  60 | |

| aag ggc cga ttc acc atc tcc aga gac aat gcc aag aac acc ctg tac | 240 |
|---|---|
| Lys Gly Arg Phe Thr Ile Ser Arg Asp Asn Ala Lys Asn Thr Leu Tyr | |
| 65                  70                  75                  80 | |

| ctg caa atg acc agt ctg aag tct gag gac aca gcc att tat tac tgt | 288 |
|---|---|
| Leu Gln Met Thr Ser Leu Lys Ser Glu Asp Thr Ala Ile Tyr Tyr Cys | |
|                 85                  90                  95 | |

| gca aga ggg acc gga acc tac tgg ggc caa ggc acc act ctc aca gtc | 336 |
|---|---|
| Ala Arg Gly Thr Gly Thr Tyr Trp Gly Gln Gly Thr Thr Leu Thr Val | |
|             100                 105                 110 | |

| tcc tca | 342 |
|---|---|
| Ser Ser | |

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 69

| cag gtc caa ctg cag cag tct ggg gct gaa ctg gtg aag cct ggg gct | 48 |
|---|---|
| Gln Val Gln Leu Gln Gln Ser Gly Ala Glu Leu Val Lys Pro Gly Ala | |
| 1               5                   10                  15 | |

| tca gtg aag ttg tcc tgc aag gct tct ggc tac acc ttc acc agc tac | 96 |
|---|---|
| Ser Val Lys Leu Ser Cys Lys Ala Ser Gly Tyr Thr Phe Thr Ser Tyr | |
|         20                  25                  30 | |

| tat atg tac tgg gtg aag cag agg cct gga caa ggc ctt gag tgg att | 144 |
|---|---|
| Tyr Met Tyr Trp Val Lys Gln Arg Pro Gly Gln Gly Leu Glu Trp Ile | |
|     35                  40                  45 | |

```
gga gag att aat cct agc aat ggt ggt act aac ttc aat gag aag ttc      192
Gly Glu Ile Asn Pro Ser Asn Gly Gly Thr Asn Phe Asn Glu Lys Phe
        50                  55                  60 aag agc aag gcc aca ctg act gta gac aaa tcc tcc agc aca gca tac      240
Lys Ser Lys Ala Thr Leu Thr Val Asp Lys Ser Ser Ser Thr Ala Tyr
 65                  70                  75                  80 atg caa ctc agc agc ctg aca tct gag gac tct gcg gtc tat tac tgt      288
Met Gln Leu Ser Ser Leu Thr Ser Glu Asp Ser Ala Val Tyr Tyr Cys
                     85                  90                  95 aca aga ggc ggt tac tac ccc ttt gac tac tgg ggc caa ggc acc act      336
Thr Arg Gly Gly Tyr Tyr Pro Phe Asp Tyr Trp Gly Gln Gly Thr Thr
            100                 105                 110 ctc aca gtc tcc tca                                                  351
Leu Thr Val Ser Ser
       115
```

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70

```
gat gtg cag ctt cag gag tcg gga cct ggc ctg gtg aaa cct tct cag       48
Asp Val Gln Leu Gln Glu Ser Gly Pro Gly Leu Val Lys Pro Ser Gln
  1               5                  10                  15 tct ctg tcc ctc aca tgc act gtc act ggc tac tca atc acc agt gat       96
Ser Leu Ser Leu Thr Cys Thr Val Thr Gly Tyr Ser Ile Thr Ser Asp
                 20                  25                  30 tat gcc tgg aat tgg atc cgg cag ttt cca gga aac aaa ctg gag tgg      144
Tyr Ala Trp Asn Trp Ile Arg Gln Phe Pro Gly Asn Lys Leu Glu Trp
             35                  40                  45 atg ggc tac ata agc ttc agt ggt tac act agt tac aac cca tct ctc      192
Met Gly Tyr Ile Ser Phe Ser Gly Tyr Thr Ser Tyr Asn Pro Ser Leu
         50                  55                  60 aaa agt cga atc tct gtc act cgg gac aca tcc agg aac caa ttc ttc      240
Lys Ser Arg Ile Ser Val Thr Arg Asp Thr Ser Arg Asn Gln Phe Phe
 65                  70                  75                  80 ctc cag ttg act tct gtg act act gag gac aca gcc aca tat tac tgt      288
Leu Gln Leu Thr Ser Val Thr Thr Glu Asp Thr Ala Thr Tyr Tyr Cys
                 85                  90                  95 gca aga gag gtc aac tat ggg gac tcc tac cac ttt gac tac tgg ggc      336
Ala Arg Glu Val Asn Tyr Gly Asp Ser Tyr His Phe Asp Tyr Trp Gly
            100                 105                 110 caa ggc acc att gtc aca gtc tcc tca                                  363
Gln Gly Thr Ile Val Thr Val Ser Ser
        115                 120
```

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 71

```
gac att gtg atg acg cag gct gca tcc tct aat cca gtc act ctt gga    48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act    96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct   144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca   192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc   240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat   288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa   336
Leu Glu Leu Pro Leu Thr Phe Gly Ala Gly Thr Lys Leu Glu Leu Lys
            100                 105                 110

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 72 gat gtt gtg ctg acc cag act cca ctc act ttg tcg gtt acc att gga    48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt    96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct   144
Asp Gly Lys Thr Tyr Leu Asn Trp Leu Leu Gln Arg Pro Gly Gln Ser
        35                  40                  45 cca aag cgc cta atc tat ctg gtg tct aaa ctg gac tct gga gtc cct   192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aaa atc   240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt   288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa   336
Thr His Phe Pro Gln Thr Phe Gly Gly Gly Thr Lys Leu Glu Ile Lys
            100                 105                 110

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: CDS
<222> LOCATION: (1)..(336)

<400> SEQUENCE: 73 gat gtt gtg atg acc cag act cca ctc act ttg tcg gtt acc att ggg      48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt      96
Arg Pro Ala Ser Ile Ser Cys Lys Ser Ser Gln Ser Leu Leu Asp Ser
            20                  25                  30 gat gga aag aca tat ttg tat tgg ttg tta cag agg cca ggc cag tct     144
Asp Gly Lys Thr Tyr Leu Tyr Trp Leu Leu Gln Arg Pro Gly Gln Ser
        35                  40                  45 cca aag cgc cta atc tat ctg gtg tct gag ctg gac tct gga gtc cct     192
Pro Lys Arg Leu Ile Tyr Leu Val Ser Glu Leu Asp Ser Gly Val Pro
    50                  55                  60 gac agg atc act ggc agt ggg tcg ggg aca gat ttc aca ctg aag atc     240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga     288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa     336
Thr His Ser Pro Tyr Thr Phe Gly Gly Gly Thr Lys Leu Glu Ile Lys
            100                 105                 110

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74 caa ctt gcg ctc act cag tca tct tca gcc tct ttc tcc ctg gga gcc      48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc      96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg     144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat     192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc     240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat     288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc     336
Ala Ile Lys Gly Gln Ser Val Phe Val Phe Gly Gly Gly Thr Lys Val
            100                 105                 110 act gtc cta                                                          345
Thr Val Leu
115
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
            115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
            115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

```
<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82
```

Glu Val Gln Leu Val Glu Ser Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

```
<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

```
<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84
```

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
            115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
                100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80
```

-continued

```
Met Glu Leu Ser Ser Leu Arg Ser Glu Asp Thr Ala Val Tyr Tyr Cys
             85                  90                  95

Thr Arg Gly Gly Tyr Tyr Pro Phe Asp Tyr Trp Gly Gln Gly Thr Thr
            100                 105                 110

Val Thr Val Ser Ser
        115
```

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110
```

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115
```

<210> SEQ ID NO 89
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
```

```
                 20                  25                  30

Ile Glu Trp His Gln Gln Pro Glu Lys Gly Pro Arg Tyr Leu Met
            35                  40                  45

Lys Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
```

```
                65                  70                  75                  80
Ser Leu Gln Ser Glu Asp Glu Ala Asp Tyr Tyr Cys Gly Val Gly Asp
                    85                  90                  95

Ala Ile Lys Gly Gln Ser Val Phe Val Phe Gly Gly Gly Thr Lys Val
            100                 105                 110

Glu Ile Lys
        115
```

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
                20                  25                  30

Tyr Ala Trp Asn Trp Ile Arg Gln His Pro Gly Lys Gly Leu Glu Trp
            35                  40                  45

Ile Gly Tyr Ile Ser Phe Ser Gly Tyr Thr Ser Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120
```

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
            35                  40                  45

Glu Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
```

```
<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

Cys Xaa Xaa Gln Gly Pro Trp Leu Glu Glu Glu Glu Glu Ala Tyr Gly
1               5                   10                  15

Trp Met Asp Phe Gly Arg Arg Ser Ala Glu Asp Glu Asn
            20                  25

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                   10                  15

<210> SEQ ID NO 100
<211> LENGTH: 101
<212> TYPE: PRT
<213> ORGANISM: Homo sapiens
```

<400> SEQUENCE: 100

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30

Asp Phe

<210> SEQ ID NO 103
<211> LENGTH: 35
<212> TYPE: PRT
<213> ORGANISM: Homo Sapiens

<400> SEQUENCE: 103

Gln Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30

Asp Phe Gly
        35

```
<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Ala Tyr Gly Trp Met Asp
1               5                   10                  15
Phe

<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15
Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```

METHODS FOR TREATING BREAST CANCER

1. CROSS REFERENCE TO RELATED APPLICATIONS

This application claims the benefit under 35 U.S.C. §119(e) of provisional application No. 61/293,612, filed 8 Jan. 2010, the contents of which are incorporated herein by reference in their entirety.

2. REFERENCE TO SEQUENCE LISTING, TABLE OR COMPUTER PROGRAM

The Sequence Listing concurrently submitted herewith under 37 CFR §1.821 in a computer readable form (CRF) via EFS-Web as file name BR006SEQLIST.txt is incorporated herein by reference. The electronic copy of the Sequence Listing was created on 30 Dec. 2010, with a file size of 79 KBytes.

3. FIELD OF INVENTION

The present disclosure is directed to, among other things, methods of treating and preventing breast cancer and its recurrence by administering a composition comprising an antibody specific for progastrin.

4. BACKGROUND

Despite decades of basic and clinical research, breast cancer remains one of the most deadly non-communicable diseases affecting principally women, although men are also diagnosed with this disease. According to the GLOBOCAN Project of the World Health Organization's International Agency for Research on Cancer, it was estimated that in 2008 the incidence of breast cancer nearly 1.4 million and that in the same year more than 450 thousand women were killed by the disease. While much has been learned recently regarding how breast cancer works at the molecular level, clinicians still rely on therapeutic modalities such as surgery, radiation, hormone therapy and chemotherapy that would have been familiar to oncologists of a generation ago. Early diagnosis, made possible by advances in imaging technology and molecular diagnostics, factors greatly in the success of any treatment. Although the efficacy of all these treatments has improved over the years, the improvement in cure rates and the increase in longevity have been incremental. Even the new targeted therapies resulting from the revolution in molecular oncology have, for the most part, improved outcomes only modestly. For example, Herceptin®, which targets the HER2 receptor, is effective only for the 20-25% of women having breast cancer whose tumors are HER2 positive.

Two of the most challenging aspects of managing breast cancer patients are metastasis and recurrence.

Metastasis occurs when the breast cancer spreads to distant organs from the primary tumor. While it is often possible to resect the primary tumor, it is the metastases that frequently end up killing the patient because they become too numerous or entwined with healthy host tissue to treat surgically. According to the American Cancer Society, the five year survival rate in the United States for patients first diagnosed with Stage IIIB breast cancer in 2001 and 2002 was 41%, which dropped to only 15% at Stage IV (i.e., metastatic breast cancer).

Recurrence is the phenomenon by which breast cancer returns after initially responding to treatment and apparently disappearing. Apart from the emotional toll inflicted on patients and their families, recurrence is problematic because the returning cancer may be less responsive to the therapy or therapies that were effective to fight the first cancer. For other patients, prior treatments for the first cancer may have caused irreversible side effects, such as cardiac or neurological damage. In such patients, the risks of using the same therapy to fight the recurrent cancer may be too great. Under these circumstances, a patient may have fewer treatment options with a concomitantly greater risk of mortality.

While improvements in surgery, radiation treatment, hormonal therapy, chemotherapy and the advent of targeted therapies have increased the longevity of patients stricken by breast cancer, many such patients continue to die within months to a few years after their diagnosis. An urgent need therefore exists for new treatments effective against breast cancer and its recurrence.

5. SUMMARY

Methods are provided for treating patients in need of treatment for progastrin sensitive breast cancer by administering a therapeutically effective amount of a composition comprising antibodies that specifically bind progastrin. In some embodiments, the breast cancer is metastatic and has spread to the bones, lungs, liver or brain. In others, the breast cancer is primary breast cancer. In a number of embodiments, the antibodies of the composition are effective to reduce the proliferation or increase the rate of cell death of progastrin sensitive breast cancer cells, reduce the average number or size of breast cancer metastases, or reduce the blood concentration of progastrin in treated patients.

In some embodiments, the composition can be administered before or after surgery or radiation therapy, or before, concurrently with or after administration of a chemotherapeutic agent or hormone therapy agent effective to treat breast cancer. The composition can also be administered before, concurrently with or after a second therapeutic antibody effective against breast cancer having specificity other than for progastrin. In certain of these embodiments, the second antibody has specificity for VEGF or HER2 and can be bevacizumab, trastuzumab and pertuzumab.

Methods are also provided for preventing progastrin sensitive breast cancer by administering to a patient in need of prevention of progastrin sensitive breast cancer a composition comprising an antibody that specifically binds to progastrin in an amount effective to prevent progastrin sensitive breast cancer. The breast cancer can be primary or metastatic. In other embodiments, the breast cancer cells contain a mutation in the BRCA1 or BRCA2 genes.

In a number of embodiments, the antibodies of the composition are effective to reduce the proliferation or increase the rate of cell death of progastrin sensitive breast cancer cells, or reduce the blood concentration of progastrin in treated patients.

In some embodiments, the composition can be administered concurrently with or after administration of a chemotherapeutic agent or hormone therapy agent effective to prevent progastrin sensitive breast cancer. The composition can also be administered concurrently with or after a second therapeutic antibody effective to prevent progastrin sensitive breast cancer having specificity other than for progastrin, such as for HER2.

Methods are also provided for preventing recurrence of progastrin sensitive breast cancer by administering to a patient in need of prevention of recurrence of progastrin sensitive breast cancer a composition comprising an antibody that specifically binds to progastrin in an amount effective to prevent recurrence of progastrin sensitive breast cancer. In certain of these methods, the patient previously underwent treatment for breast cancer, such as surgery, radiation therapy, biological therapy, immunotherapy, hormonal therapy and chemotherapy, after which the breast cancer apparently disappeared.

In a number of embodiments, the antibodies of the composition are effective to reduce the proliferation or increase the rate of cell death of progastrin sensitive breast cancer cells, or reduce the blood concentration of progastrin in treated patients. In other embodiments, the composition can be administered concurrently with or after a second therapeutic agent effective to prevent progastrin sensitive breast cancer including, for example, an antibody having specificity other than for progastrin.

Methods are also provided for inhibiting the growth of progastrin sensitive breast cancer stem cells in a patient by administering to a patient in need of inhibition of growth of a progastrin sensitive breast cancer stem cells a composition comprising an antibody that specifically binds to progastrin in an amount effective to inhibit said progastrin sensitive breast cancer stem cells.

In a number of embodiments, the antibodies of the composition are effective to reduce the proliferation or increase the rate of cell death of progastrin sensitive breast cancer stem cells, or reduce the blood concentration of progastrin in treated patients. In other embodiments, the composition can be administered concurrently with or after a second therapeutic agent effective to inhibit the growth of progastrin sensitive breast cancer stem cells, for example, an antibody having specificity other than for progastrin.

Methods are also provided for monitoring the efficacy of a treatment for progastrin sensitive breast cancer in a patient, such as chemotherapy, biological therapy, immunotherapy or antibody therapy, by determining the concentration of progastrin in a first sample, such as a bodily fluid or biopsy of breast cancer, obtained from a patient after treatment for breast cancer, and then comparing the concentration of progastrin in the first sample to that in a second sample obtained from the same patient, where a reduction in the concentration of progastrin in said second sample compared to said first sample indicates that the treatment was effective.

In some embodiments of the method, the second sample is obtained before the patient is treated for breast cancer, or after treatment, but before the first sample is obtained. In other embodiments, an assay, such as an RIA or ELISA, employing an antibody specific for progastrin is used to determine the concentration of progastrin in the first sample.

Methods are also provided for diagnosing the presence of breast cancer in a patient by determining the concentration of progastrin in a sample, such as a bodily fluid, obtained from a patient suspected of having breast cancer and then comparing the concentration of progastrin in the sample to a predetermined value where an elevated level of progastrin in the sample compared to the predetermined value indicates the presence of breast cancer in the patient. In some embodiments, the predetermined value is based on an average of sample values obtained when the patient was known to be free of breast cancer and in others the predetermined value is based on a population average.

In some embodiments of the method, the patient was formerly treated for breast cancer and is in remission at the time the sample is obtained. In other embodiments, the method includes the additional step of performing a second diagnostic test on the patient to confirm the presence of breast cancer including, for example, a blood test, a medical imaging test or a genetic test. In some embodiments the medical imaging test is a mammogram and in other embodiments the genetic test is to detect mutations in the BRCA1 or BRCA2 genes. In yet other embodiments, an assay such as an RIA or ELISA employing an antibody specific for progastrin is used to determine the concentration of progastrin in the sample.

The antibody compositions for use in the methods above can be administered by a number of different routes, such as intravenously, and different methods, such as by infusion or by bolus. The antibody dose can vary over a wide range, depending on the nature and need of the subject to be treated. The dose can be administered in one sitting over multiple spaced sittings.

Different types of anti-hPG antibodies may be used in the methods including, for example, polyclonal antibodies, monoclonal antibodies (which may be humanized), as well as chimeric antibodies, antibodies having the isotypes of IgA1, IgA2, IgD, IgE, IgG1, IgG2, IgG3, IgG4, and IgM, and single chain antibodies. In some other embodiments, the antibodies are conjugated to moieties that usefully alter their function or characteristics, for example, to increase serum half life. In yet other embodiments, amino acid changes can be effected for a similar purpose, or other purposes. Antibody affinity for progastrin can range widely as long as therapeutic efficacy is maintained. In some embodiments, the antibodies recognize just one epitope of progastrin. In other embodiments, mixtures of antibodies specific for different epitopes of progastrin can be used.

Also provided are kits to facilitate administration of anti-progastrin antibody compositions to patients. In some embodiments, kits include an anti-progastrin antibody in either lyophilized form or as an aqueous solution, a diluent, such as pharmaceutical grade water or buffer, and a device for administering the anti-progastrin antibody, such as a syringe and needle. In other embodiments, kits may additionally include a second therapeutic agent, such as, but not limited to, a chemotherapeutic agents of the disclosure, or others.

Antibodies for use in the methods of treating metastatic colorectal cancer can have a range of binding affinities for progastrin, for example, about 5000 nM, or even higher, for example, at least about 4000 nM, 3000 nM, 2000 nM, 1000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM or 0.001 nM.

In certain embodiments of the disclosed methods, monoclonal antibodies as disclosed herein may be used including, for example, MAb1, MAb2, MAb3, MAb4, MAb5, MAb6, MAb7, MAb8, MAb9, MAb10, MAb11, MAb12, MAb13, MAb14, MAb15, MAb16, MAb17, MAb18, MAb19, MAb20, MAb21, MAb22, MAb23, or others.

In other embodiments of the disclosed methods, monoclonal antibodies as disclosed herein may be used including, for example, monoclonal antibodies having a heavy chain variable region ($V_H$) in which the first CDR is selected from $V_H$ CDR 1.3, $V_H$ CDR 1.4, $V_H$ CDR 1.8, $V_H$ CDR 1.13, $V_H$ CDR 1.16, $V_H$ CDR 1.19, the second CDR is selected from $V_H$ CDR 2.3, $V_H$ CDR 2.4, $V_H$ CDR 2.8, $V_H$ CDR 2.13, $V_H$ CDR 2.16, $V_H$ CDR 2.19, and the third CDR is selected from $V_H$ CDR 3.3, $V_H$ CDR 3.4, $V_H$ CDR 3.8, $V_H$ CDR 3.13, $V_H$ CDR 3.16, $V_H$ CDR 3.19. The particular sequences of these CDRs are described below. Other useful antibodies have a light chain region ($V_L$) in which the first CDR is selected from $V_L$ CDR 1.3, $V_L$ CDR 1.4, $V_L$ CDR 1.8, $V_L$ CDR 1.13, $V_L$ CDR 1.16, $V_L$ CDR 1.19, the second CDR is selected from $V_L$ CDR 2.3, $V_L$ CDR 2.4, $V_L$ CDR 2.8, $V_L$ CDR 2.13, $V_L$ CDR 2.16, $V_L$ CDR 2.19, and the third CDR is selected from $V_L$ CDR 3.3, V$_L$ CDR 3.4, V$_L$ CDR 3.8, V$_L$ CDR 3.13, V$_L$ CDR 3.16, V$_L$ CDR 3.19. The particular sequences of these CDRs are also described below.

6. BRIEF DESCRIPTION OF THE FIGURES

FIG. 1 provides a graph comparing gastrin gene expression levels among three human metastatic breast cancer cell lines relative to SW480 cells.

Figure 2:
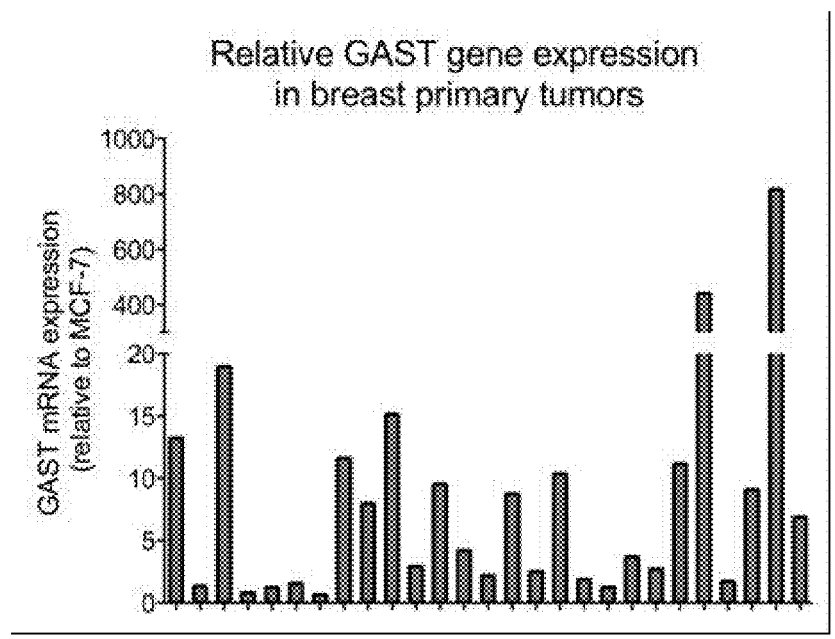

FIG. 2 provides a graph comparing the relative gastrin gene expression levels in primary breast tumors from different patients.

Figure 3:
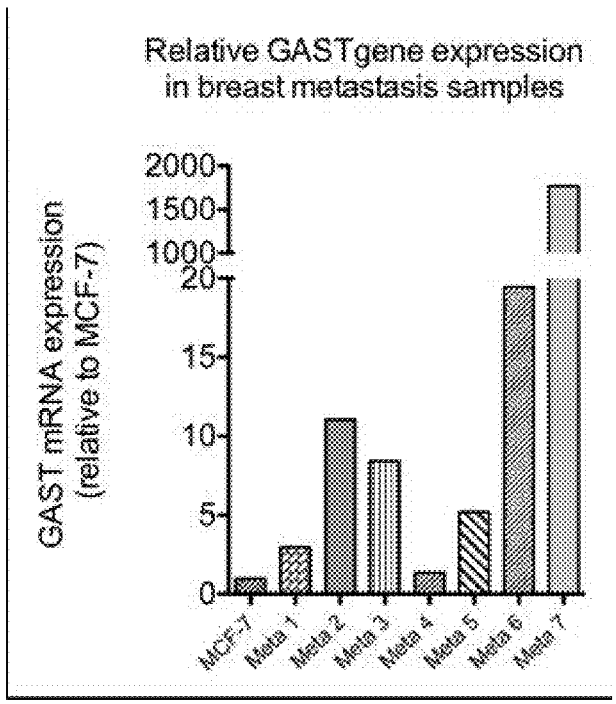

FIG. 3 provides a graph comparing the relative gastrin gene expression levels in metastatic breast tumors from different patients.

Figure 4:
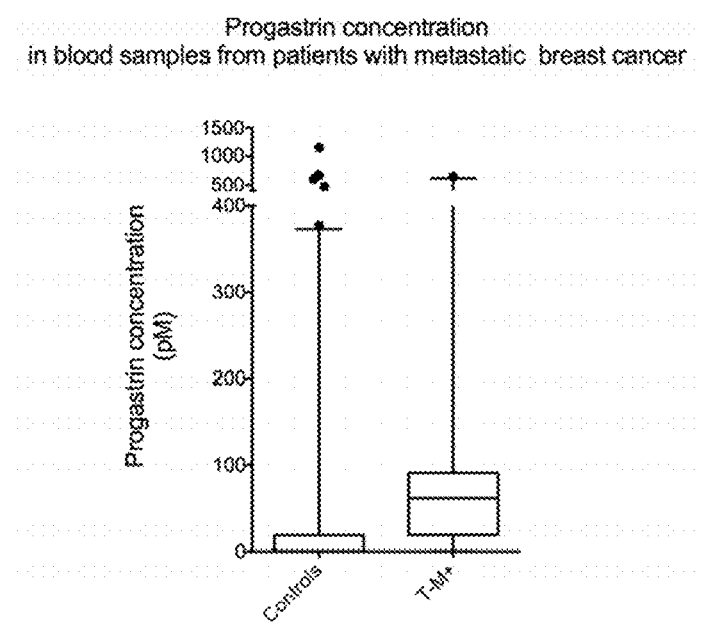

FIG. 4 provides a graph showing blood progastrin concentrations in patients with metastatic breast cancer from whom the primary tumor was resected compared to healthy controls.

Figure 5:
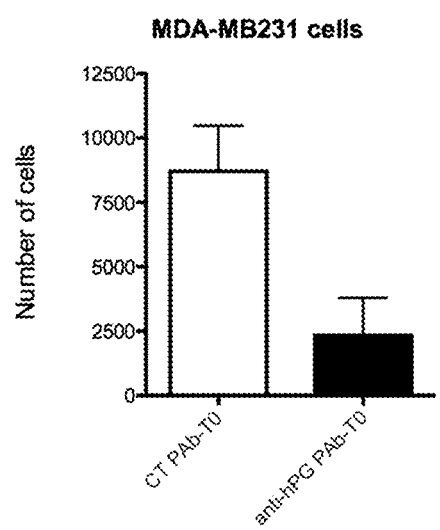

FIG. 5 provides a graph comparing the effect of control and anti-hPG polyclonal antibodies on the growth of MDA-MB-231 metastatic breast cancer cells in culture.

Figure 6:
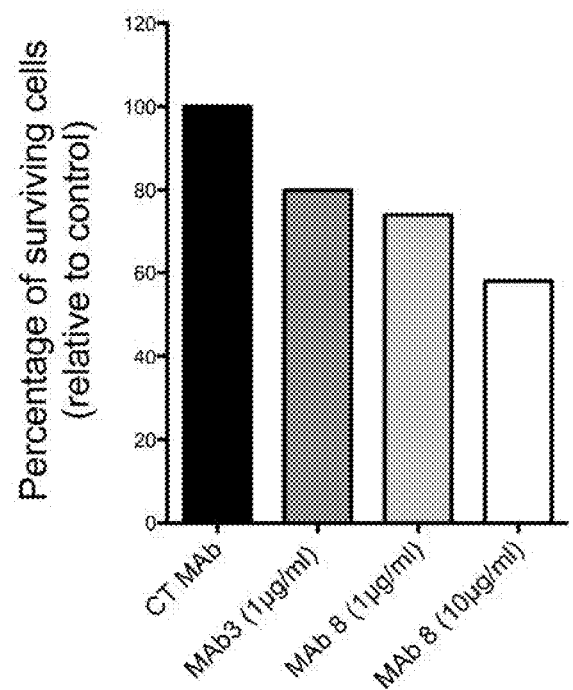

FIG. 6 provides a graph comparing the effect of control and an anti-hPG monoclonal antibodies MAb3 and MAb8 on the growth of MDA-MB-231 metastatic breast cancer cells in culture.

Figure 7:
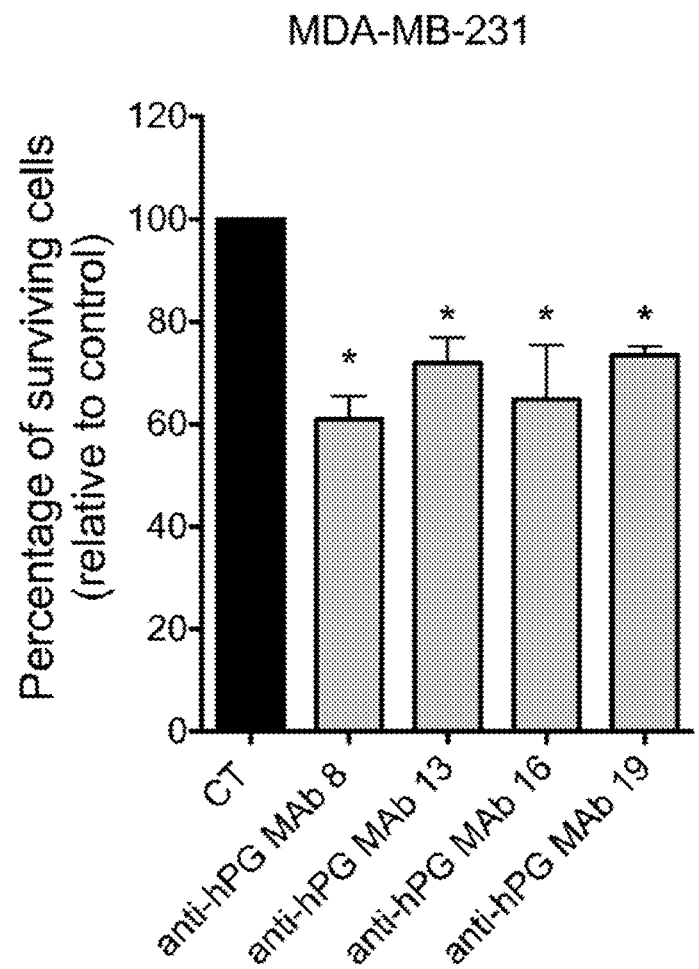

FIG. 7 provides a graph comparing the effect of control and an anti-hPG monoclonal antibodies MAb8, MAb13, MAb16 and MAb19 on the growth of MDA-MB-231 metastatic breast cancer cells in culture.

Figure 8:
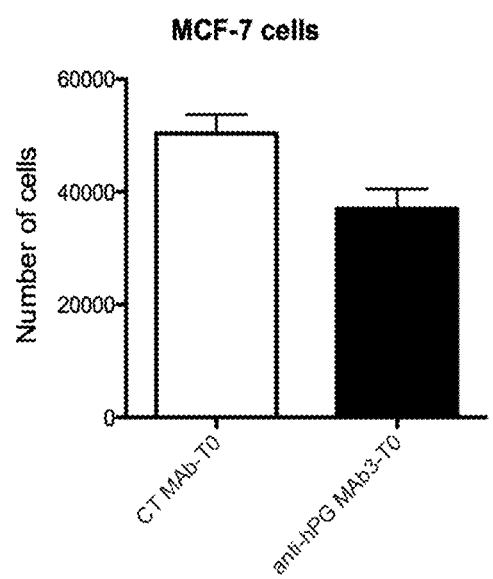

FIG. 8 provides a graph comparing the effect of control and an anti-hPG monoclonal antibody on the growth of MCF-7 metastatic breast cancer cells in culture.

Figure 9:
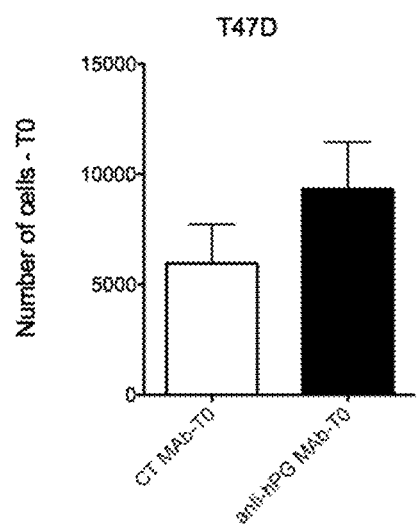

FIG. 9 provides a graph comparing the effect of control and an anti-hPG monoclonal antibody on the growth of T47D metastatic breast cancer cells in culture.

Figure 10:
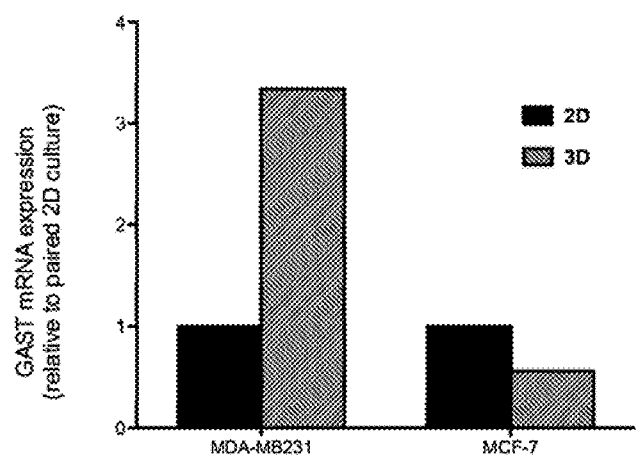

FIG. 10 provides a graph comparing the relative amount of gastrin gene expression associated with growth of two different metastatic breast cancer cell lines under normal tissue culture conditions and low adherence culture conditions.

Figure 11:
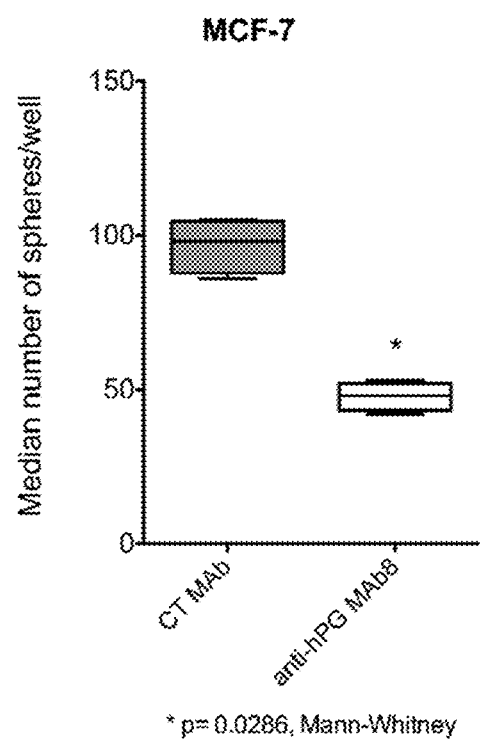

FIG. 11 provides a graph comparing the effect of control and anti-hPG monoclonal antibody MAb8 on the growth as spheroids of MCF-7 metastatic breast cancer cells under low adherence culture conditions.

Figure 12:
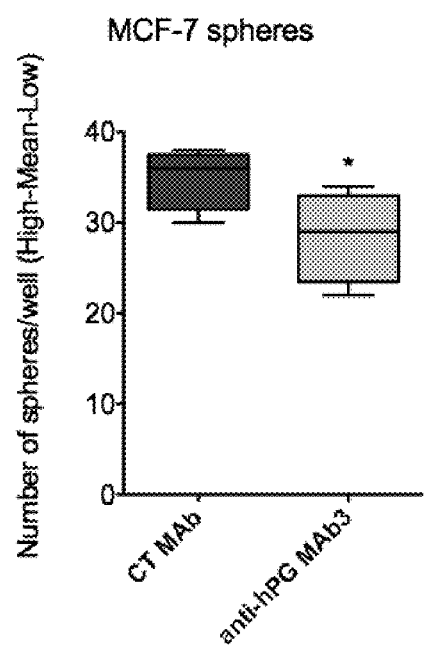

FIG. 12 provides a graph comparing the effect of control and anti-hPG monoclonal antibody MAb3 on the growth as spheroids of MCF-7 metastatic breast cancer cells under low adherence culture conditions.

FIG. 13 provides amino acid sequences of human preprogastrin (SEQ ID NO:100), where the signal peptide sequence is underlined, mature human progastrin (SEQ ID NO:101) and certain products of progastrin processing, including G34 (SEQ ID NO:102), G34-Gly (SEQ ID NO:103), G17 (SEQ ID NO:104), G17-Gly (SEQ ID NO:105) and CTFP (SEQ ID NO:106).

FIG. 14. provides polynucleotide and amino acid sequences of variable light and variable heavy chains of certain exemplary murine anti-hPG monoclonal antibodies. In each case, the three CDRs are shown in bolded-underlined text. Specifically:

FIG. 14A provides the polypeptide sequence of the V$_H$ chain of murine anti-hPG MAb3 (SEQ ID NO:12) and a polynucleotide sequence encoding it (SEQ ID NO:16);

FIG. 14B provides the polypeptide sequence of the V$_L$ chain of murine anti-hPG MAb3 (SEQ ID NO:13) and a polynucleotide sequence encoding it (SEQ ID NO:17);

FIG. 14C provides the polypeptide sequence of the V$_H$ chain of murine anti-hPG MAb4 (SEQ ID NO:14) and a polynucleotide sequence encoding it (SEQ ID NO:18);

FIG. 14D provides the polypeptide sequence of the V$_L$ chain of murine anti-hPG MAb4 (SEQ ID NO:15) and a polynucleotide sequence encoding it (SEQ ID NO:19);

FIG. 14E provides the polypeptide sequence of the V$_H$ chain of murine anti-hPG MAb8 (SEQ ID NO:59) and a polynucleotide sequence encoding it (SEQ ID NO:67);

FIG. 14F provides the polypeptide sequence of the V$_L$ chain of murine anti-hPG MAb8 (SEQ ID NO:63) and a polynucleotide sequence encoding it (SEQ ID NO:71);

FIG. 14G provides the polypeptide sequence of the V$_H$ chain of murine anti-hPG MAb13 (SEQ ID NO:60) and a polynucleotide sequence encoding it (SEQ ID NO:68);

FIG. 14H provides the polypeptide sequence of the V$_L$ chain of murine anti-hPG MAb13 (SEQ ID NO:64) and a polynucleotide sequence encoding it (SEQ ID NO:72);

FIG. 14I provides the polypeptide sequence of the V$_H$ chain of murine anti-hPG MAb16 (SEQ ID NO:61) and a polynucleotide sequence encoding it (SEQ ID NO:69);

FIG. 14J provides the polypeptide sequence of the V$_L$ chain of murine anti-hPG MAb16 (SEQ ID NO:65) and a polynucleotide sequence encoding it (SEQ ID NO:73);

FIG. 14K provides the polypeptide sequence of the V$_H$ chain of murine anti-hPG MAb19 (SEQ ID NO:62) and a polynucleotide sequence encoding it (SEQ ID NO:70); and FIG. 14L provides the polypeptide sequence of the V$_L$ chain of murine anti-hPG MAb19 (SEQ ID NO:66) and a polynucleotide sequence encoding it (SEQ ID NO:74).

FIG. 15 provides projected polypeptide sequences for humanized variable heavy and light chains of selected anti-hPG monoclonal antibodies described herein. In each case, the three CDRs are shown in bolded-underlined text. Specifically:

FIG. 15A provides the projected amino acid sequence of the V$_H$ chain of humanized MAb3 (SEQ ID NO:21);

FIG. 15B provides the projected amino acid sequence of the V$_L$ chain of humanized MAb3 (SEQ ID NO:22);

FIG. 15C provides the projected amino acid sequence of the V$_H$ chain of humanized MAb4 (SEQ ID NO:23);

FIG. 15D provides the projected amino acid sequence of the V$_L$ chain of humanized MAb4 (SEQ ID NO:24);

FIG. 15E provides the projected amino acid sequence of the V$_H$ chain of humanized MAb8(a) (SEQ ID NO:75);

FIG. 15F provides the projected amino acid sequence of the V$_L$ chain of humanized MAb8(a) (SEQ ID NO:76);

FIG. 15G provides the projected amino acid sequence of the V$_H$ chain of humanized MAb8(b) (SEQ ID NO:77);

FIG. 15H provides the projected amino acid sequence of the V$_L$ chain of humanized MAb8(b) (SEQ ID NO:78);

FIG. 15I provides the projected amino acid sequence of the V$_H$ chain of humanized MAb8(c) (SEQ ID NO:79);

FIG. 15J provides the projected amino acid sequence of the V$_L$ chain of humanized MAb8(c) (SEQ ID NO:76);

FIG. 15K provides the projected amino acid sequence of the V$_H$ chain of humanized MAb13(a) (SEQ ID NO:80);

FIG. 15L provides the projected amino acid sequence of the V$_L$ chain of humanized MAb13(a) (SEQ ID NO:81);

FIG. 15M provides the projected amino acid sequence of the V$_H$ chain of humanized MAb13(b) (SEQ ID NO:82);

FIG. 15N provides the projected amino acid sequence of the V$_L$ chain of humanized MAb13(b) (SEQ ID NO:83);

FIG. 15O provides the projected amino acid sequence of the V$_H$ chain of humanized MAb16(a) (SEQ ID NO:84);

FIG. 15P provides the projected amino acid sequence of the V$_L$ chain of humanized MAb16(a) (SEQ ID NO:85);

FIG. 15Q provides the projected amino acid sequence of the $V_H$ chain of humanized MAb16(b) (SEQ ID NO:86);

FIG. 15R provides the projected amino acid sequence of the $V_L$ chain of humanized MAb16(b) (SEQ ID NO:87);

FIG. 15S provides the projected amino acid sequence of the $V_H$ chain of humanized MAb16(c) (SEQ ID NO:88);

FIG. 15T provides the projected amino acid sequence of the $V_L$ chain of humanized MAb16(c) (SEQ ID NO:89);

FIG. 15U provides the projected amino acid sequence of the $V_H$ chain of humanized MAb19(a) (SEQ ID NO:90);

FIG. 15V provides the projected amino acid sequence of the $V_L$ chain of humanized MAb19(a) (SEQ ID NO:91);

FIG. 15W provides the projected amino acid sequence of the $V_H$ chain of humanized MAb19(b) (SEQ ID NO:92);

FIG. 15X provides the projected amino acid sequence of the $V_L$ chain of humanized MAb19(b) (SEQ ID NO:93);

FIG. 15Y provides the projected amino acid sequence of the $V_H$ chain of humanized MAb19(c) (SEQ ID NO:94); and FIG. 15Z provides the projected amino acid sequence of the $V_L$ chain of humanized MAb19(c) (SEQ ID NO:95).

7. DETAILED DESCRIPTION

7.1. Breast Cancer

Most cancers of the female breast begin in the cells that line the ducts that serve to carry milk from the milk producing glands or lobules. Such breast cancers are referred to as ductal cancers. Other breast cancers begin in the cells lining the lobules, called lobular cancers. A minority of breast cancers begin in other tissues comprising the breast, including the stroma, which is the fatty and connective tissue surrounding the ducts and lobules, lymphatic vessels and blood vessels.

Nearly all breast cancers are carcinomas which begin in epithelial cells lining the ducts or lobules. Such cancers are known as ductal carcinoma and lobular carcinoma, respectively. Breast cancer can also start as a sarcoma, which forms in connective tissue of the breast, including muscle, fat or blood vessels.

Particular types of breast cancer include, but are not necessarily limited to ductal carcinoma in situ, lobular carcinoma in situ, invasive (or infiltrating) ductal carcinoma, invasive (or infiltrating) lobular carcinoma. Less common types of breast cancer include inflammatory breast cancer, triple-negative breast cancer, mixed tumors, medullary carcinoma, metaplastic carcinoma, mucinous carcinoma, Paget disease of the nipple, tubular carcinoma, papillary carcinoma, adenoid cystic carcinoma (adenocystic carcinoma), phyllodes tumor and angiosarcoma.

7.2. Breast Cancer Metastasis

Metastasis refers to a process by which cancer spreads. Briefly, tumor cells leave a primary tumor, travel via the blood circulation or lymphatic system to a new tissue site, and form a secondary tumor. The tumors at the new tissue site are referred to as metastatic tumors, and typically identify the source of the primary tumor. For example, breast cancer that has spread to other tissues is referred to as "metastatic breast cancer," despite the tissue location of the secondary, metastatic tumor. The most common organs to which breast cancer metastasizes are the bones, lungs, liver, or brain, but breast cancer may spread to other organs as well.

Cancer cells frequently spread to lymph nodes near the primary tumor, which is called lymph node involvement or regional disease.

Without wishing to be limited by any particular theory of operation, metastasis is thought to consist of a number of distinct steps: invasion and migration, intravasation, circulation, extravasation and colonization, proliferation and angiogenesis. During invasion and migration, individual cells detach themselves from the primary tumor and invade adjacent, healthy tissue. To accomplish this, the cancer cells must become motile, and are hypothesized to undergo a phenotypic transformation, called an epithelial to mesenchymal transition, which facilitates this. Kalluri, R., et al., J. Clin. Invest., 119(6) (2009), 1420-28. Such cells may produce enzymes which degrade the extracellular matrix, thereby facilitating migration out of the primary tumor and the surrounding healthy tissue. When a cancer cell encounters a blood or lymphatic vessel, it inserts itself between the endothelial cells lining the vessels and penetrates into the blood stream or lymphatic system. The aberrant cell then travels via the circulatory system or lymphatic system to a new organ or to a lymph node. The cancer cell may then lodge in the capillaries or lymphatics of an organ, such as liver, lung, or other tissue or organ, and then extravasate by penetrating the endothelium into the tissue space. Finally, during colonization, proliferation and angiogenesis, the neoplastic cells take up residence in their new host tissue and begin to grow. When the new metastatic tumor reaches sufficient size, it may secrete growth factors, such as VEGF, to stimulate the growth of new blood vessels into the tumor so as to supply oxygen and nutrition to the fast growing tumor.

7.3. Breast Cancer Recurrence

Breast cancer recurrence is defined as a return of breast cancer after treatment which apparently caused the breast cancer to disappear. If the returning breast cancer is in the same place as the original cancer or is very close to it (e.g., in the same breast or near the mastectomy scar), it is known as local recurrence. Cancer found in the opposite breast is not a recurrence and is considered to be a new cancer. Where the returning breast cancer grows in lymph nodes or tissues near the place of the original cancer, it is known as a regional recurrence, and where the returning breast cancer metastasized to organs or tissues far from the place of the original cancer, it is known as a distant recurrence.

7.4. Cancer Stem Cells and Breast Cancer

Solid tumors are not necessarily homogenous tissues. Rather, some tumors comprise a plurality of aberrant cell types having distinct phenotypic and functional properties. In this respect, such tumors are analogous to abnormal organs. One important difference among the cells comprising solid tumors is the extent to which they are capable of initiating formation of a new tumor when transplanted to a new site in the same host, or to a new host of the same or different species. Cells having this property are known as tumor or cancer initiating cells, or alternatively, tumor or cancer stem cells. In contrast, other cells comprising the tumor have much reduced potential to initiate new tumors after transplantation, even when many more cells are used. In one non-limiting example, 100-fold fewer cells derived from a breast cancer cell line having a cancer stem cell phenotype were able to form new tumors in mice compared to cells from the same cell line that lacked the stem cell phenotype. Gupta, P. B., et al., "Identification of selective inhibitors of cancer stem cells by high-throughput screening," Cell, 13864-659 (2009). See also, Filmore, C. M. and C. Kuperwasser, "Human breast cancer cell lines contain stem-like cells that self-renew, give rise to phenotypically diverse progeny and survive chemotherapy," Br. Cancer Res., 10:R25 (2008).

In many tumors, cancer stem cells comprise a relatively small proportion of all viable cells existing within a tumor. By contrast, the majority of tumor cells comprising the bulk of the tumor are unable to initiate a new tumor when transplanted. In some tumors, however, cancer stem cells may constitute the majority, or even all the cells comprising the tumor. As used herein, bulk tumor cells refer to tumor cells unable to initiate new tumors upon transplantation, unless large numbers of such cells are used. Cancer stem cells also have different phenotypic characteristics than bulk tumor cells including the ability to self-renew and form a new tumor upon transplantation of a relatively small number of cancer stem cells, and expression of different markers detectable by fluorescence activated cell sorting (FACS) or other assays. Other distinctions between cancer stem cells and bulk tumor cells are also possible.

Without wishing to be bound by any particular theory of operation, cancer stem cells are believed to share certain properties with normal stem cells which in the context of cancer stem cells contributes to their ability to give rise to tumors. In particular, cancer stem cells undergo asymmetric cell division to produce two types of daughter cells. The first remains undifferentiated and retains the stem cell characteristic of its parent of being able to renew itself indefinitely. The other daughter, called a progenitor cell, is capable of dividing and differentiating, albeit aberrantly, to give rise to the spectrum of more differentiated cells found in many solid tumors. Progenitor cells proliferate at a higher rate than stem cells and thus contribute to the physical growth of the tumor, whereas the stem cells are responsible for the ability of the tumor to grow indefinitely by generating new progenitors.

These properties allow cancer stem cells to give rise ultimately to the great number of cells comprising the growing tumor. Thus, when transplanted into a new animal, cancer stem cells can reconstitute the type of tumor from which they originated, even after multiple serial transplantations. Cancer stem cells however, unlike normal stem cells, harbor genetic mutations and/or epigenetic changes that can result in altered proliferation patterns and/or low rates of apoptosis, as well as result in aberrant differentiation causing the accumulation of the abnormal cells that may constitute the bulk of the tumor.

Cancer stem cells can be identified according to a number of phenotypic characteristics that distinguish them from bulk tumor cells. First, as noted above, cancer stem cells have the ability to initiate a new tumor when transplanted into a new host. By contrast, bulk tumor cells are either unable to initiate new tumors or require many more cells than cancer stem cells to achieve new tumor initiation. Cancer stem cells are also identifiable by their expression or non-expression of certain markers, whereas bulk tumor cells from the same tumor have different patterns of marker expression. Cancer stem cells also have a preferential ability, compared to bulk tumor cells, to grow under serum-free low-adherence culture conditions and form so-called spheroids. Other phenotypic differences capable of distinguishing cancer stem cells from bulk tumor cells are possible.

As noted above, cancer stem cells may also be identified according to patterns of expression of certain markers, either alone or in combination with others. Cancer stem cells from different tumors, however, may exhibit different marker phenotypes. Such markers include proteins expressed within the cell, or on the cell surface, and can be detected using a variety of techniques including, but not limited to, immunohistochemistry, immunofluorescence and FACS analysis. Other techniques for detecting marker are also possible according to the knowledge of those ordinarily skilled in the art. Markers also include proteins the activity of which can be assayed functionally in cancer stem cells. Non-limiting examples of types of markers include transporter proteins, such as those that export substances from cells or uptake substances into cells, enzymes, such as detoxifying enzymes.

Exemplary markers that may be used to identify breast cancer stem cells include, but are not limited to: CD44, CD24 and ESA. Other markers useful for identifying cancer stem cells are also possible. In some embodiments, the absence of expression of a marker is indicative of the cancer stem cell phenotype. In some embodiments of the present disclosure, breast cancer stem cells may be identified by the following marker phenotype, using FACS, or other techniques familiar to those of ordinary skill in the art: CD44(+)/CD24(−), CD44(+)/CD24(low) and CD44(+)/CD24(−)/ESA(+). Expression of other markers, and combinations and patterns thereof, may also be used to identify cancer stem cells in these cancers, as well as other types of cancers. In other embodiments of the present disclosure, breast cancer stem cells may be identified using FACS analysis as those cells sorted into the so-called side population according to their preferential ability to exclude certain dyes. One non-limiting example of such a dye is Hoechst dye 33342.

As noted above, cancer stem cells can also be distinguished from bulk tumor cells by their increased capacity to initiate new tumor growth after transplantation into a new host. Thus, one way to confirm the identity of a population of cells suspected of being cancer stem cells is to test their ability to initiate tumor growth after transplantation into a non-human recipient animal.

Methods of transplantation useful for assessing whether a tumor or cell line contains cancer stem cells are familiar to those of ordinary skill in the art. As a non-limiting example, a tumor, or portion thereof, suspected of containing cancer stem cells is isolated, such as by surgical resection. Thereafter the tumor tissue is minced and treated with enzymes, or some other treatment, effective to disaggregate the tumor and release its constituent cells. Alternatively, where a cell line is under analysis, it may only be necessary to disassociate the cells with enzymatic or chemical treatment.

After a cell suspension is prepared, the cells are collected by centrifugation and subpopulations known to correspond to cancer stem cells are isolated according to methods known in the art. As discussed above, in one non-limiting example, such cells express certain patterns of markers indicative of cancer stem cells, which are detectable using specific antibodies and fluorescence activated cell sorting (FACS). In other embodiments, subpopulations suspected of containing cancer stem cells can be isolated according to other phenotypic characteristics, such as their ability to exclude certain dyes.

After isolating the relevant cellular subpopulations, predetermined numbers of such cells are then implanted into one or more target tissues or organs in a recipient animal. In some embodiments, the recipient animal is an immunodeficient mouse, including but not limited to nude mice, mice with severe combined immunodeficiency (SCID), and nonobese-diabetic SCID (NOD-SCID) mice. Other species can also be used, according to the knowledge of the ordinarily skilled artisan.

Cells can be implanted subcutaneously, into fat pads (such as the mammary fat pad of mice), into the brain, pancreas or liver, or into the kidney (such as into the renal capsule). Cells can be implanted into other tissues and organs, as well. In some embodiments, the target tissue or organ is chosen to replicate the tissue or organ of origin of the tumor under analysis. However, in other embodiments, distinct tissues or organs are chosen in which to host the implanted cells. As a non-limiting example, colon cancer stem cells can be transplanted into the renal capsule of a NOD-SCID mouse to assess their ability to initiate a new tumor.

After implantation, which is effected using techniques familiar to those of ordinary skill, the cells are left undisturbed to determine whether a new tumor grows at the site of implantation. For cells implanted subcutaneously, tumor growth can be assessed by visual examination and palpation of the site of implantation. If a tumor does grow, its size can be measured through time using calipers. For cells implanted into an internal organ, the animal may be sacrificed at a predetermined time post-implantation to determine if a tumor is present, and if so, its size. Alternatively, according to the knowledge of the ordinary skilled artisan, non-invasive techniques can be used to assess tumor growth.

The cancer stem cell phenotype is also characterized by the preferential ability of cancer stem cells to grow as spheroids under serum-free, low adherence culture conditions, whereas bulk tumor cells are less likely to be able to grow as spheroids under the same conditions. Spheroids are compacted balls of cells that form as certain cells grow in culture after being seeded as disaggregated suspensions. The formation of such spheroids is promoted when the cells are grown in serum-free medium (e.g., MammoCult®, available from StemCell Technologies, Inc., Vancouver, Canada), generally in the presence of specific growth factors (including, but not limited to, Epidermal Growth Factor (EGF) and basic Fibroblast Growth Factor (bFGF)), and in tissue culture dishes having surfaces to which mammalian cells poorly adhere. Similar to stem cells from normal tissues, it has been discovered that cancer stem cells preferentially grow as spheroids under the appropriate culture conditions. See, e.g., Rappa, G., et al., *Exp. Cell Res.*, 314:2110 (2008); Singh, S. K., et al., *Cancer Res.*, 63:5821 (2003); Fang, D., et al., *Cancer Res.*, 65:9328 (2005). By contrast, bulk tumor cells, which tend to more highly differentiated, are less likely to form spheroids under the same culture conditions. Where bulk tumor cells are able to form spheroids, they tend to be smaller and/or fewer in number compared to those formed by a similar number of cancer stem cells.

7.5. Cancer Stem Cells and Breast Cancer Recurrence

Tumor cells with properties of cancer stem cells have been identified that exhibit enhanced resistance to radiation and/or chemotherapeutic agents. Different molecular mechanisms have been proposed to explain resistance of cancer stem cells to radiation or chemotherapeutic agents. For example, it has been reported that certain cancer stem cells may be able to more readily repair their DNA after genotoxic insults, whereas other cancer stem cells express high levels of anti-apoptotic proteins or of molecular pumps effective to eliminate chemotherapeutic agents entering such cells. Eyler, C. E., and J. N. Rich, *J. Clin. Oncol.*, 26:2839-2845 (2008). That cancer stem cells also proliferate more slowly than progenitor cells may also explain the comparative ability of stem cells to survive exposure to radiation and toxic chemotherapeutic agents that would kill bulk tumor cells.

Without wishing to be bound by any particular theory of operation, the observation that cancer stem cells are resistant to radiation and chemotherapy may explain the phenomenon of recurrence in cancer patients treated with such therapies. Eyler, supra. In such patients, treatment is initially effective, causing the tumors to shrink or disappear in diagnostic scans, but the tumors reappear some time after treatment ceases.

With respect to the role of cancer stem cells in the mechanism of recurrence, it is hypothesized that while most or even all the bulk tumor cells are killed by the therapy, there remain a number of viable cancer stem cells that survive due to their enhanced ability to resist the effects of radiation or chemotherapy. After therapy is concluded, these surviving cells continue to grow, permitting reformation of the original tumor or formation of new tumors.

Consistent with this theory, it was reported that treatment of mice transplanted with a human breast cancer cell line with a chemotherapeutic agent was effective to select for and enrich the proportion of cells from the tumors having characteristics of cancer stem cells. Yu, F., et al., 2007, "let-7 Regulates self renewal and tumorigenicity of breast cancer cells," *Cell* 131:1109-23.

The observation that breast cancer stem cells are resistant to both radiation and to chemotherapeutic agents suggests that such cells are responsible for breast cancer recurrence. Phillips, T. M., et al., "The response of $CD24^{-/low}/CD44^+$ breast cancer-initiating cells to radiation," J. Natl. Canc. Inst., 98(24):1777-1785 (2006), Gupta, P. B., et al., and Filmore, C. M. and C. Kuperwasser, supra.

7.6. Advances in Understanding the Role of Progastrin in Breast Cancer

As described in further detail in the examples, applicants have surprisingly discovered that the gastrin gene (GAST) is expressed in three different human metastatic breast cancer cell lines, MCF-7 cells, MDA-MB231 cells and T47D cells at varying levels compared to control cell lines. Related to the data from the in vitro experiments, applicants have also surprisingly discovered that the gastrin gene was expressed at varying levels among 27 out of 105 primary breast cancers and among 7 out of 25 metastatic breast cancers obtained from human breast cancer patients.

Because progastrin is a product of the gastrin gene (along with other peptides processed post-translationally from the same gene product), the data from the in vitro and in vivo gastrin gene expression studies suggests that some, but not all primary and metastatic breast cancers secrete prograstin protein. Confirmation with respect to metastatic breast cancer comes from the observation by applicants that the median blood level of PG among patients diagnosed with metastatic breast cancer from whom the primary tumors were removed was higher compared to that in the blood of healthy controls. Thus, metastatic breast cancer secretes PG which can be detected in the blood. Higher than normal levels of PG were also detected in the blood of certain patients diagnosed with primary breast cancer. Diagnostic tests are therefore possible to detect the presence of breast cancer in patients by comparing the blood PG level in a patient suspected of having breast cancer to the blood PG level in healthy patients without cancer. Levels of PG in blood plasma and/or serum can be detected using neutralizing or non-neutralizing antibodies of the present disclosure using techniques such as, but not limited to, RIA or ELISA. A tentative diagnosis of breast cancer based on higher than normal levels of blood PG can then be confirmed using other tests, such as a medical imaging test, for example, CT or MRI.

Applicants have also surprisingly discovered that the growth in culture of certain human metastatic breast cancer cell lines, e.g., MCF-7 cells and MDA-MB-231 cells, is inhibited by treatment with polyclonal and/or monoclonal antibodies that specifically recognize hPG. Experiments using MDA-MB-231 cells demonstrated that the inhibitory effect using an anti-hPG monoclonal antibody was dose responsive and that the inhibitory effect could be mediated by antibodies recognizing both the N-terminus and C-terminus of progastrin. By contrast, treating the T47D human metastatic breast cancer cell line with a monoclonal antibody against hPG did not significantly affect the growth of such cells. These surprising discoveries are interpreted to mean that some but not all human metastatic breast cancer cells are sensitive to PG and that the growth of such cells can be inhibited by treatment with neutralizing anti-hPG antibodies.

A PG-sensitive breast cancer cell is one that at least partly depends on progastrin for its survival and/or growth, directly or indirectly. Without wishing to be bound by any particular theory of operation, it is hypothesized that neutralizing anti-hPG antibodies are effective to inhibit the survival and/or growth of such cells by binding to PG and blocking PG-dependent signaling. Progastrin is therefore prevented from mediating its survival and/or growth-promoting effects. Other mechanisms by which anti-PG antibodies inhibit the survival and/or growth of breast cancer cells may exist, however, and the particular mechanism of action is not intended to limit the scope of the present disclosure.

Based on the observation that neutralizing antibodies against hPG can inhibit the growth of certain human metastatic breast cancer cells, methods of treating PG-sensitive metastatic breast cancer are possible by administering therapeutically effective amounts of neutralizing anti-hPG antibodies to patients in need of treatment for metastatic breast cancer.

Other experiments carried out by applicants surprisingly demonstrated that metastatic breast cancer contains PG-sensitive breast cancer stem cells the growth of which can be inhibited by treatment with neutralizing anti-hPG antibodies. In particular, applicants found that about 95% of MDA-MB-231 cells expressed a phenotypic marker, CD44+/CD24−, which identified them as breast cancer stem cells (experiment not shown). Because MDA-MB-231 cells are PG-sensitive and nearly all these cells express the breast cancer stem cell marker, it is likely that the stem cells are PG-sensitive. Consistent with this, T47D cells, which were found not to be PG-sensitive, contain no cells expressing CD44+/CD24− (experiment not shown), whereas MCF-7 cells, which were reported to contain about 1.6% CD44+/CD24− cells (Phillips, et al., supra) were also found to be sensitive to the growth inhibitory effect of an anti-hPG antibody.

Supporting the conclusion that certain breast cancer stem cells are PG-sensitive was the observation that gastrin gene expression in MDA-MB-231 cells increased when the cells were grown under low adherence culture conditions which favor the growth of cancer stem cells. Gastrin gene expression decreased in MCF-7 cells, however, when grown under low adherence conditions, although the impact on PG secretion from such cells is not yet known.

Even though a relatively low proportion of MCF-7 cells express CD44+/CD24−, applicants found further support for the idea that breast cancer stem cells are PG-sensitive by growing MCF-7 cells under low adherence culture conditions and determining the effect of specific antibody treatment on spheroid formation. As explained in the Examples, treatment with an anti-hPG monoclonal antibody reduced the number of spheroids compared to controls. Because spheroid formation under low adherence culture conditions is a property associated with cancer stem cells, these results indicate MCF-7 cells, like MDA-MB-231 cells, contain PG-sensitive breast cancer stem cells the growth of which are inhibited by neutralizing antibodies.

Building on this work, applicants also tested the effect of pretreating MCF-7 cells with a different anti-hPG monoclonal antibody while the cells were grown under conventional culture conditions after which the antibody was removed and the cells were allowed to continue to grow under low adherence conditions, which selects for the growth of cancer stem cells. Applicants surprisingly found that MCF-7 cells pretreated with an anti-hPG monoclonal antibody formed fewer spheroids compared to controls even though the antibodies were not present during the low adherence growth phase of the experiment. This result is interpreted to mean both that MCF-7 cells contain breast cancer stem cells that are inhibited by a neutralizing anti-hPG antibody and that the inhibitory effect on the growth of such stem cells does not require the continued presence of the antibodies.

Based on the observation that certain breast cancers contain PG-sensitive cancer stem cells and that cancer stem cells are believed to be responsible for the phenomenon of cancer recurrence, methods of preventing breast cancer recurrence are possible by treating patients in need of prevention of breast cancer recurrence with a neutralizing anti-hPG antibody in an amount effective to prevent the recurrence of breast cancer, wherein the breast cancer is PG-sensitive. Applicants' surprising findings are also the basis for methods of preventing the growth of PG-sensitive breast cancer stem cells by treating such cells with an amount of a neutralizing anti-hPG antibody effective to inhibit the growth of such cells.

7.7. Antibodies

Antibodies useful in the methods and kits disclosed herein are those that specifically bind human progastrin over other products of the gastrin gene. As illustrated in FIG. 13, the gastrin gene is translated into a 101-amino acid polypeptide, called pre-progastrin, which contains a signal sequence (underlined) that is cleaved, giving rise to progastrin, an 80-amino-acid polypeptide. Progastrin, in turn, is cleaved to generate a 34-amino-acid product, corresponding in sequence to residues 38-71 of progastrin, which is then extended at its carboxy terminus with a glycine residue, generating glycine-extended G34 ("G34-Gly"). A by-product of this cleavage is a 6-amino-acid peptide, called the C-terminal flanking peptide, or CTFP, which corresponds in sequence to residues 75-80 of progastrin. G34-Gly is then further cleaved to generate a 17-residue polypeptide corresponding in sequence to residues 55-71 of progastrin and referred to as G17-Gly. Removal of the C-terminal glycines of G34-Gly and G17-Gly, followed by C-terminal amidation, yields G34 and G17, respectively, both of which are C-terminal amidated.

As used herein, an antibody is "highly specific for" hPG or "highly specifically binds" hPG if it binds to full-length progastrin but does not bind at all to CTFP, to amidated gastrin, or to glycine-extended gastrin, and is "specific for" hPG or "specifically binds" hPG if it exhibits at least about 5-fold greater binding of hPG than CTFP and the other products of the gastrin gene, as measured in standard binding assays. A specific ELISA assay that can be used to assess the specificity of a particular anti-hPG antibody is provided in Example 12.

Such highly specific and/or specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The epitope bound by the anti-hPG antibodies is not critical. Useful anti-hPG antibodies may bind an N-terminal region of hPG, a C-terminal region of hPG, or a different region of hPG. Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076,454 to Singh) and a peptide corresponding to the last ten amino acids at the C-terminal end of hPG (see WO 07/135,542 to Hollande et al.) failed to generate monoclonal antibodies. As noted in the '329 and '041 applications, antigenic N-terminal and C-terminal sequences within the hPG sequence have been identified that can be used to generate nonoclonal antibodies that specifically bind hPG. Interestingly, the antigenic sequence need not be limited to regions of the hPG sequence that are unique to it. Peptide antigens having regions of sequence in common with other products of the gastrin gene, for example, G17, G34 and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDAPLG (SEQ ID NO:25). Exemplary immunogens useful for obtaining N-terminal anti-hPG antibodies, as well as CDR and $V_H$ and $V_L$ sequences of N-terminal anti-hPG monoclonal antibodies obtained with these exemplary immunogens, are provided in TABLE 1A, below, and the Example sections:

TABLE 1A

N-Terminal Anti-hPG Monoclonal Antibodies

| Immunogen | Hybridoma (Deposit #) | MAb | Murine CDR Sequences | | | Murine $V_H$ and $V_L$ Sequences | Humanized $V_H$ and $V_L$ Sequences (projected) |
|---|---|---|---|---|---|---|---|
| N1 | 43B9G11 | MAb1 | | | | | |
| N1 | WE5H2G7 | MAb2 | | | | | |
| N2 | 6B5B11C10 | MAb3 | $V_H$ CDR 1.3 | GYIFTSYW | (SEQ ID NO: 1) | $mV_H.3$ (SEQ ID NO: 12) | $hV_H.3$ (SEQ ID NO: 21) |
| | | | $V_H$ CDR 2.3 | FYPGNSDS | (SEQ ID NO: 2) | | |
| | | | $V_H$ CDR 3.3 | TRRDSPQY | (SEQ ID NO: 3) | | |
| | | | $V_L$ CDR 1.3 | QSIVHSNGNTY | (SEQ ID NO: 4) | | |
| | | | $V_L$ CDR 2.3 | KVS | (SEQ ID NO: 5) | | |
| | | | $V_L$ CDR 3.3 | FQGSHVPFT | (SEQ ID NO: 6) | | |
| N2 | 20D2C3G2 | MAb4 | VH CDR 1.4 | GYTFSSSW | (SEQ ID NO: 7) | $mV_H.4$ (SEQ ID NO: 14) | $hV_H.4$ (SEQ ID NO: 23) |
| | | | VH CDR 2.4 | FLPGSGST | (SEQ ID NO: 8) | | |
| | | | VH CDR 3.4 | ATDGNYDWFAY | (SEQ ID NO: 9) | | |
| | | | VL CDR 1.4 | ASLVHSSGVTY | (SEQ ID NO: 10) | $mV_L.4$ (SEQ ID NO: 15) | $hV_L.4$ (SEQ ID NO: 24) |
| | | | VL CDR 2.4 | KVS | (SEQ ID NO: 5) | | |
| | | | VL CDR 3.4 | SQSTHVPPT | (SEQ ID NO: 11) | | |
| N2 | 1E9A4A4 (I-4376) | MAb15 | | | | | |
| N2 | 1E9D9B6 | MAb16 | $V_H$ CDR 1.16 | GYTFTSYY | (SEQ ID NO: 39) | $mV_H.16$ (SEQ ID NO: 61) | $hV_H.16a$ (SEQ ID NO: 84) |
| | | | $V_H$ CDR 2.16 | INPSNGGT | (SEQ ID NO: 43) | | $hV_H.16b$ (SEQ ID NO: 86) |
| | | | $V_H$ CDR 3.16 | TRGGYYPFDY | (SEQ ID NO: 47) | | $hV_H.16c$ (SEQ ID NO: 88) |
| | | | $V_L$ CDR 1.16 | QSLLDSDGKTY | (SEQ ID NO: 50) | $mV_L.16$ (SEQ ID NO: 65) | $hV_L.16a$ (SEQ ID NO: 85) |
| | | | $V_L$ CDR 2.16 | LVS | (SEQ ID NO: 53) | | $hV_L.16b$ (SEQ ID NO: 87) |
| | | | $V_L$ CDR 3.16 | WQGTHSPYT | (SEQ ID NO: 57) | | $hV_L.16c$ (SEQ ID NO: 89) |
| N2 | 1C8D10F5 | MAb17 | | | | | |
| N2 | 1A7C3F11 | MAb18 | | | | | |
| N2 | 1B3B4F11 | MAb19 | $V_H$ CDR 1.19 | GYSITSDYA | (SEQ ID NO: 40) | $mV_H.19$ (SEQ ID NO: 62) | $hV_H.19a$ (SEQ ID NO: 90) |
| | | | $V_H$ CDR 2.19 | ISFSGYT | (SEQ ID NO: 44) | | $hV_H.19b$ (SEQ ID NO: 92) |
| | | | $V_H$ CDR 3.19 | AREVNYGDSYHFDY | (SEQ ID NO: 48) | | $hV_H.19c$ (SEQ ID NO: 94) |
| | | | $V_L$ CDR 1.19 | SQHRTYT | (SEQ ID NO: 51) | $mV_L.19$ (SEQ ID NO: 66) | $hV_L.19a$ (SEQ ID NO: 91) |
| | | | $V_L$ CDR 2.19 | VKKDGSH | (SEQ ID NO: 54) | | $hV_L.19b$ (SEQ ID NO: 93) |
| | | | $V_L$ CDR 3.19 | GVGDAIKGQSVFV | (SEQ ID NO: 58) | | $hV_L.19c$ (SEQ ID NO: 95) |
| N2 | 1C11F5E8 | MAb20 | | | | | |

Immunogen N1 = SWKPRSQQPDAPLG-Ahx-Cys-BSA, also represented as (SEQ ID NO: 25)-Ahx-Cys-BSA
Immunogen N2 = SWKPRSQQPDAPLG-Ahx-Cys-KLH, also represented as (SEQ ID NO: 25)-Ahx-Cys-KLH In TABLE 1A, all amino acid sequences are represented using conventional N→C orientation. For each immunogen, the progastrin peptide was synthesized with a C-terminal linker of one aminohexanoic acid (Ahx) residue followed by a cysteine (Cys) residue, which was then conjugated to a either a bovine serum albumin ("BSA") or keyhole limpet hemocyanin ("KLH") carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYGWMDFGRRSAEDEN (SEQ ID NO:27). Exemplary immunogens including this antigen useful for obtaining C-terminal anti-hPG antibodies, as well as CDR and $V_H$ and $V_L$ sequences of C-terminal anti-hPG monoclonal antibodies obtained with these exemplary immunogens, are provided in TABLE 1B, below, and the Examples section.

nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs1-4 and 15-20, epitopes comprise at least the following sequences: DAPLG (SEQ ID NO:28), PDAPLG (SEQ ID

TABLE 1B

C-Terminal Anti-hPG Monoclonal Antibodies

| Immunogen | Hybridoma (Deposit #) | MAb | Murine CDR Sequences | | Murine $V_H$ and $V_L$ Sequences | Humanized $V_H$ and $V_L$ Sequences (projected) |
|---|---|---|---|---|---|---|
| C1 | 1B4A11D11 (I-4371) | MAb5 | | | | |
| C1 | 1B6A11F2 (I-4372) | MAb6 | | | | |
| C1 | 1B11E4B11 (I-4373) | MAb7 | | | | |
| C1 | 1C10D3B9 | MAb8 | $V_H$ CDR 1.8 | GFTFTTYA (SEQ ID NO: 37) | m$V_H$.8 (SEQ ID NO: 59) | h$V_H$.8a (SEQ ID NO: 75) |
| | | | $V_H$ CDR 2.8 | ISSGGTYT (SEQ ID NO: 41) | | h$V_H$.8b (SEQ ID NO: 77) |
| | | | $V_H$ CDR 3.8 | ATQGNYSLDF (SEQ ID NO: 45) | | h$V_H$.8c (SEQ ID NO: 79) |
| | | | $V_L$ CDR 1.8 | KSLRHTKGITF (SEQ ID NO: 49) | m$V_L$.8 (SEQ ID NO: 63) | h$V_L$.8a (SEQ ID NO: 76) |
| | | | $V_L$ CDR 2.8 | QMS (SEQ ID NO: 52) | | h$V_L$.8b (SEQ ID NO: 78) |
| | | | $V_L$ CDR 3.8 | AQNLELPLT (SEQ ID NO: 55) | | h$V_L$.8c (SEQ ID NO: 76) |
| C1 | 1D8F5B3 | MAb9 | | | | |
| C1 | 1E1C7B4 | MAb10 | | | | |
| C1 | 2B4C8C8 (I-4374) | MAb11 | | | | |
| C1 | 2B11E6G4 (I-4375) | MAb12 | | | | |
| C1 | 2C6C3C7 | MAb13 | $V_H$ CDR 1.13 | GFIFSSYG (SEQ ID NO: 38) | m$V_H$.13 (SEQ ID NO: 60) | h$V_H$.13a (SEQ ID NO: 80) |
| | | | $V_H$ CDR 2.13 | INTFGDRT (SEQ ID NO: 42) | | h$V_H$.13b (SEQ ID NO: 82) |
| | | | $V_H$ CDR 3.13 | ARGTGTY (SEQ ID NO: 46) | | |
| | | | $V_L$ CDR 1.13 | QSLLDSDGKTY (SEQ ID NO: 50) | m$V_L$.13 (SEQ ID NO: 64) | h$V_L$.13a (SEQ ID NO: 81) |
| | | | $V_L$ CDR 2.13 | LVS (SEQ ID NO: 53) | | h$V_L$.13b (SEQ ID NO: 83) |
| | | | $V_L$ CDR 3.13 | WQGTHFPQT (SEQ ID NO: 56) | | |
| C1 | 2H9F4B7 | MAb14 | | | | |
| C2 | 1F11F4E10 | MAb21 | | | | |

Immunogen C1 = KLH-Cys-Ahx-Ahx-QGPWLEEEEEAYGWMDFGRRSAEDEN, also represented as KLH-Cys-Ahx-Ahx-(SEQ ID NO: 27)
Immunogen C2 = DT-Cys-Ahx-Ahx-QGPWLEEEEEAYGWMDFGRRSAEDEN, also represented as DT-Cys-Ahx-Ahx-(SEQ ID NO: 27)

In TABLE 1B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in TABLES 1A and 1B were mapped using the SPOT technique and alanine scanning, as described in Laune et al., 2002, J. Immunol. Methods 267:53-70 and Laune, 1997, J. Biol. Chem. 272:30937-30944, respectively (see also, Example 6 of the '329 application).

In the SPOT technique, 15 amino acid peptide sequences spanning a putative epitope are generated and spotted onto a NO:29), PRSQQPD (SEQ ID NO:30), WKPRSQQPD (SEQ ID NO:31), or WKPRSQQPDAPLG (SEQ ID NO:32), as shown in TABLE 2A below.

TABLE 2A

| MAb# | PG peptide antigen: SWKPRSQQPDAPLG | SEQ ID NO |
|---|---|---|
| MAb2 | WKPRSQQPDAPLG | 32 |
| MAb4 | WKPRSQQPDAPLG | 32 |
| MAb1 | PDAPLG | 29 |

TABLE 2A-continued

| MAb# | PG peptide antigen: SWKPRSQQPDAPLG | SEQ ID NO |
|---|---|---|
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbsS-7, 9-12, 14 and 21-23, epitopes comprise at least the following sequences: FGRR (SEQ ID NO:33), MDFGR (SEQ ID NO:34), AEDEN (SEQ ID NO:35), and GWMDFGRR (SEQ ID NO:36), as shown in TABLE 2B, below.

TABLE 2A

| MAb# | PG peptide antigen: QGPWLEEEEEAYGWMDFGRRSAEDEN | SEQ ID NO |
|---|---|---|
| MAb14 | GWMDFGRR | 36 |
| MAb11 | MDFGR | 34 |
| MAb5 | FGRR | 33 |
| MAb6 | FGRR | 33 |
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in TABLES 1A & 1B can be identified in competitive binding assays with exemplary MAbs 1-23, or with other reference antibodies that bind N- or C-terminal epitopes, as will be described in more detail in a later section.

As also reported in the '329 and '041 applications, not all anti-hPG antibodies, even those that exhibit a high degree of specificity and affinity for hPG, neutralize the biological activity of hPG. For example, although anti-hPG MAb14 binds hPG with a $K_D$ of about 6 pM, it did not, at least at the concentration tested, inhibit the growth of certain colorectal cancer cells in an in vitro assay, whereas other anti-hPG monoclonal antibodies, for example MAb1-MAb13 and MAb15-MAb23, exhibited inhibitory activity to varying degrees. While both non-neutralizing and neutralizing antibodies that specifically bind hPG are useful for the diagnostic methods of the present disclosure, anti-hPG antibodies useful for therapeutic methods should exhibit neutralizing activity. As described in the Examples, MAb3 and MAb8 were demonstrated to have neutralizing activity when tested for their ability to inhibit the growth of MDA-MB-231 and MCF7 breast cancer cells in culture. Whether other antibodies of the present disclosure are neutralizing may be determined empirically.

As used herein, a "neutralizing anti-hPG antibody" is an anti-hPG antibody that yields a statistically significant reduction in the number of live breast cancer cells in a test sample treated with the anti-hPG antibody as compared to a control sample treated with a non-specific antibody. A specific assay for assessing the capability of any particular anti-hPG antibody to be neutralizing is described in Example 13. Those anti-hPG antibodies that exhibit at least about a 50% reduction in the number of live breast cancer cells in this assay are believed to be especially useful in treating breast cancer, although anti-hPG antibodies exhibiting lower levels of neutralizing activity, for example, a statistically significant reduction of 40%, 30%, 20%, 15%, or even 10%, in the number of live breast cancer cells in this assay are expected to provide therapeutic benefits. Exemplary cells for use in these assays include, but are not limited to, the PG-sensitive breast cancer cell lines described herein.

Accordingly, in some embodiments, for example therapeutic embodiments, useful anti-hPG antibodies are neutralizing. As disclosed herein and in the '329 and '041 applications, the ability of an anti-hPG monoclonal antibody to be neutralizing is not epitope-dependent, as both N-terminal (e.g., MAb3) and C-terminal (e.g., MAb8) anti-hPG monoclonal antibodies exhibited neutralizing activity in assays with breast cancer cells. Thus, in some specific embodiments, the neutralizing anti-hPG antibodies are N-terminal neutralizing anti-hPG antibodies. In other embodiments, the neutralizing anti-hPG antibodies are C-terminal neutralizing anti-hPG antibodies.

The affinity of any specific anti-hPG antibody is not critical. However, for some uses, antibodies exhibiting affinities of at least about 1 μM may be preferred. For therapeutic uses, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, 0.001 nM or even greater, may be desirable. The measured affinities of the anti-hPG monoclonal antibodies identified in TABLES 1A & 1B range from $10^{-6}$ to $10^{-12}$ M, as noted in TABLE 3, below:

TABLE 3

| Monoclonal Antibody | Affinity constant measured $K_D$ (M) |
|---|---|
| Anti-hPG MAb 1 | 2.5 μM ($2.5 \times 10^{-6}$M) |
| Anti-hPG MAb 2 | 185 nM ($1.85 \times 10^{-7}$M) |
| Anti-hPG MAb 3 | 6.4 nM ($6.4 \times 10^{-9}$M) |
| Anti-hPG MAb 4 | 3.5 nM ($3.5 \times 10^{-9}$M) |
| Anti-hPG MAb 5 | 13 pM ($1.30 \times 10^{-11}$M) |
| Anti-hPG MAb 6 | 0.6 nM ($6.38 \times 10^{-10}$M) |

TABLE 3-continued

| Monoclonal Antibody | Affinity constant measured KD (M) |
|---|---|
| Anti-hPG MAb 7 | 58 pM (5.84 × 10$^{-11}$M) |
| Anti-hPG MAb 8 | 0.1 nM (1.08 × 10$^{-10}$M) |
| Anti-hPG MAb 10 | 3.6 nM (3.62 × 10$^{-9}$M) |
| Anti-hPG MAb 11 | 0.3 nM (3.12 × 10$^{-10}$M) |
| Anti-hPG MAb 12 | 0.4 nM (4.43 × 10$^{-10}$M) |
| Anti-hPG MAb 13 | 0.6 nM (6.12 × 10$^{-10}$M) |
| Anti-hPG MAb 14 | 6.8 pM (6.86 × 10$^{-12}$M) |
| Anti-hPG MAb 15 | 0.2 nM (2.11 × 10$^{-10}$M) |
| Anti-hPG MAb 16 | 0.2 nM (2.78 × 10$^{-10}$M) |
| Anti-hPG MAb 17 | 8.3 nM (8.29 × 10$^{-9}$M) |
| Anti-hPG MAb 18 | 1.2 nM (1.24 × 10$^{-9}$M) |
| Anti-hPG MAb 19 | 0.7 nM (7.79 × 10$^{-10}$M) |
| Anti-hPG MAb 20 | 0.2 nM (2.47 × 10$^{-10}$M) |
| Anti-hPG MAb 21 | 3.9 nM (3.90 × 10$^{-9}$M) |
| Anti-hPG MAb 22 | 5 nM (4.94 × 10$^{-9}$M) |
| Anti-hPG MAb 23 | 0.4 μM (3.99 × 10$^{-7}$M) |

An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 14.

As noted in TABLES 1A & 1B, a number of N-terminal and C-terminal monoclonal antibodies specific for hPG have been identified and, as disclosed in the '329 and '041 applications, all except MAb14 exhibited neutralizing activity against certain colorectal cancer cells. Additionally, as described in the Examples, MAb3, MAb8, MAb13, MAb16 and MAb19 exhibited neutralizing activity against MDA-MB-231 breast cancer cells and MAb 3 exhibited neutralizing activity against MCF7 breast cancer cells.

Several of the hybridomas useful for obtaining the antibodies were deposited on Oct. 6, 2010 with the Collection Nationale de Cultures de Microorganismes (CNCM) in accordance with the Treaty of Budapest. The designated names of the hybridomas producing anti-hPG MAbs1-23 and the depository registration numbers of those hybridomas deposited are provided in TABLES 1A & 1B. In addition, for several of the antibodies, the amino acid sequences of their variable heavy chains ($V_H$), variable light chains ($V_L$), $V_L$ complementarity determining regions (CDRs) and $V_H$ CDRs have been determined. These amino acid sequences, and the shorthand nomenclature used to reference them throughout the disclosure, are also provided in TABLES 1A & 1B. Briefly, murine heavy and light chain variable domains are referred to herein as m$V_H$ and m$V_L$ followed by the number of the corresponding monoclonal antibody, for example m$V_H$.3 and m$V_L$.3 for the variable light and variable heavy chains of anti-hPG MAb3, respectively. Similarly, human heavy and light chain variable domains are referred to herein as h$V_H$ and h$V_L$ followed by the number of the corresponding monoclonal antibody. The three variable heavy chain CDRs and three variable light chain CDRs are referred to as $V_H$ CDR 1, 2, or 3, and $V_L$ CDR 1, 2, or 3, respectively, followed by the number of the specific anti-hPG monoclonal antibody. For example, $V_H$ CDR 1 of MAb3 is denoted $V_H$ CDR 1.3 and $V_L$ CDR 1 of MAb3 is denoted $V_L$ CDR 1.3. $V_H$ CDR 2 of MAb3 is denoted $V_H$ CDR 2.3, and $V_L$ CDR 2 of MAb3 is denoted $V_L$ CDR 2.3.

It is expected that corresponding CDRs and/or $V_H$ and $V_L$ chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific non-limiting example to illustrate the various combinations possible, such an antibody could include in its $V_L$ chain, CDRs 1 and 2 of MAb5 ($V_L$ CDR 1.5 and $V_L$ CDR 2.5, respectively) and CDR 3 of MAb6 ($V_L$ CDR 3.6), and in its $V_H$ chain, CDR 1 of MAb6 ($V_H$ CDR 1.6) and CDRs 2 and 3 of MAb5 ($V_H$ CDR 2.5 and $V_H$ CDR 3.5, respectively). Amino acid sequences of CDRs of antibodies produced by hybridomas that have been deposited can be obtained using conventional means.

Amino acid sequences of CDRs of antibodies produced by hybridomas that have been deposited can be obtained using conventional means. For example, relevant sequences of the antibodies produced by hybridomas 6B5B11C10 and 20D2C3G2 were determined as follows. Briefly, total RNA was isolated from frozen cell pellets using RNABee reagent, AMSBio catalogue no. CS-104B, used according to manufacturer's instructions. cDNA for V-regions was prepared from mRNA using reverse-transcriptase polymerase chain reaction (RT-PCR), followed by 5' rapid amplification of cDNA ends (RACE). cDNA synthesis was carried out using constant-region-specific primers, after which the first strand product was purified and terminal deoxynucleotide transferase was used to add homopolymeric tails to the 3' ends of the cDNA. The "tailed" cDNA sequences were then amplified by PCR using primer pairs, one primer each for the homopolymeric tail and either the $V_H$ or $V_L$ region, respectively. Heavy and light chain variable region PCR products were then cloned into a "TA" cloning vector (p-GEM-T easy, Promega cat. no A 1360) and sequenced using standard procedures. See FIG. 14A-B (MAb 3), FIG. 14C-D (MAb 4).

Similarly, relevant sequences of antibodies produced by hybridomas 1C10D3B9, 2C6C3C7, 1B3B4F1, and 1E9D9B61 were determined as follows. Total RNA was isolated from frozen cell pellets using RNAqueous®-4PCR kit (Ambion cat. No. AM1914) used according to manufacturer's instructions. Heavy chain V-region mRNA was amplified using a set of six degenerate primer pools (HA to HF) and light chain V-region mRNA was amplified using a set of eight degenerate primer pools, seven for the κ cluster (KA to KG) and one for the λ cluster (LA). cDNA for variable regions was prepared from mRNA using RT-PCR. cDNA synthesis was carried out using constant-region-specific primers, followed by PCR using pools of degenerate primers for 5' murine signal sequences and primers to 3' constant regions for each of IgGVH, IgκVL and IgλVL. (Jones et al., 1991, *Rapid PCR cloning of full-length mouse immunoglobulin variable regions*, Bio/Technology 9:88-89). Heavy and light chain variable region PCR products were then cloned into a "TA" cloning vector (p-GEM-T easy, Promega cat. no A 1360) and sequenced using standard procedures. See FIGS. 14E-F (MAb 8), 14G-H (MAb 13), 14I-J (Mab 16), and 14K-L (Mab 19).

With reference to TABLE 1A, specific embodiments of N-terminal anti-hPG antibodies useful in the methods and kits described herein include, but are not limited to, the following:

(a) antibodies having $V_L$ CDRs that correspond in sequence to the $V_L$ CDRs of MAb1, MAb2, MAb3, MAb4, MAb15, MAb16, MAb17, MAb18, MAb19 or MAb20, and $V_H$ CDRs that correspond in sequence to the $V_H$ CDRs of MAb1, MAb2, MAb3, MAb4, MAb15, MAb16, MAb17, MAb18, MAb19 or MAb20;

(b) antibodies having $V_L$ CDRs and $V_H$ CDRs that correspond in sequence to the $V_L$ and $V_H$ CDRs of MAb1, MAb2, MAb3, MAb4, MAb15, MAb16, MAb17, MAb18, MAb19 or MAb20;

(c) antibodies in which:
(i) $V_L$ CDR 1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("$V_L$ CDR 1.19"; SEQ ID NO:51);
(ii) $V_L$ CDR2 is selected from KVS ("$V_L$ CDR 2.3" and ("$V_L$ CDR 2.4"; SEQ ID NO:5), LVS ("$V_L$ CDR 2.16"; SEQ ID NO:53), and VKKDGSH ("$V_L$ CDR 2.19"; SEQ ID NO:54);
(iii) $V_L$ CDR3 is selected from FQGSHVPFT ("$V_L$ CDR\ 3.3"; SEQ ID NO:6), SQSTHVPPT ("$V_L$ CDR 3.4"; SEQ ID NO:11), WQGTHSPYT ("$V_L$ CDR 3.16"; SEQ ID NO:57), and GVGDAIKGQSVFV ("$V_L$ CDR 3.19"; SEQ ID NO:58);
(iv) $V_H$ CDR1 is selected from GYIFTSYW ("$V_H$ CDR 1.3"; SEQ ID NO:1), GYTFSSSW ("$V_H$ CDR 1.4"; SEQ ID NO:7), GYTFTSYY ("$V_H$ CDR 1.16"; SEQ ID NO:39), and GYSITSDYA ("$V_H$ CDR 1.19"; SEQ ID NO:40);
(v) $V_H$ CDR2 is selected from FYPGNSDS ("$V_H$ CDR 2.3"; SEQ ID NO:2), FLPGSGST ("$V_H$ CDR 2.4"; SEQ ID NO:8), INPSNGGT ("$V_H$ CDR 2.16"; SEQ ID NO:43), and ISFSGYT ("$V_H$ CDR 2.19"; SEQ ID NO:44); and
(vi) $V_H$ CDR3 is selected from TRRDSPQY ("$V_H$ CDR 3.3"; SEQ ID NO:3), ATDGNYDWFAY ("$V_H$ CDR 3.4" SEQ ID NO:9), TRGGYYPFDY ("$V_H$ CDR 3.16"; SEQ ID NO:47), and AREVNYGDSYHFDY ("$V_H$ CDR 3.19"; SEQ ID NO:48);

(d) antibodies having a $V_L$ that corresponds in sequence to the $V_L$ of MAb1, MAb2, MAb3, MAb4, MAb15, MAb16, MAb17, MAb18, MAb19 or MAb20 and a $V_H$ that corresponds in sequence to the $V_H$ of MAb1, MAb2, MAb3, MAb4, MAb15, MAb16, MAb17, MAb18, MAb19 or MAb20; and (e) antibodies having a $V_L$ and a $V_H$ that corresponds in sequence to the $V_L$ and $V_H$ of MAb1, MAb2, MAb3, MAb4, MAb15, MAb16, MAb17, MAb18, MAb19 or MAb20.

With reference to TABLE 1B, specific embodiments of C-terminal anti-hPG antibodies useful in the methods and kits described herein include, but are not limited to, the following:

(a) antibodies having $V_L$ CDRs that correspond in sequence to the $V_L$ CDRs of MAb5, MAb6, MAb7, MAb8, MAb9, MAb10, MAb11, MAb12, MAb13, MAb14, MAb21, MAb22 or MAb23 and $V_H$ CDRs that correspond in sequence to the $V_H$ CDRs of MBb5, MAb6, MAb7, MAB8, MAB9, MAb10, MAb11, MAb12, MAb13, MAb14, MAb21, MAb22 or MAb23;

(b) antibodies having $V_L$ CDRs and $V_H$ CDRs that correspond in sequence to the $V_L$ and $V_H$ CDRs of MAb5, MAb6, MAb7, MAb8, MAb9, MAb10, MAb11, MAb12, MAb13, MAb14, MAb21, MAb22 or MAb23;

(c) antibodies in which:
(i) $V_L$ CDR1 is selected from KSLRHTKGITF ("$V_L$ CDR 1.8"; SEQ ID NO:49) and QSLLDSDGKTY ("$V_L$ CDR 1.13"; SEQ ID NO:50);
(ii) $V_L$ CDR2 is selected from QMS ("$V_L$ CDR 2.8"; SEQ ID NO:52) and LVS ("$V_L$ CDR 2.13"; SEQ ID NO:53);
(iii) $V_L$ CDR3 is selected from AQNLELPLT ("$V_L$ CDR 3.8"; SEQ ID NO:55) and WQGTHFPQT ("$V_L$ CDR 3.13"; SEQ ID NO:56);
(iv) $V_H$ CDR1 is selected from GFTFTTYA ("$V_H$ CDR 1.8"; SEQ ID NO:37) and GFIFSSYG ("$V_H$ CDR 1.13"; SEQ ID NO:38);
(v) $V_H$ CDR2 is selected from ISSGGTYT ("$V_H$ CDR 2.8"; SEQ ID NO:41) and INTFGDRT ("$V_H$ CDR 2.13"; SEQ ID NO:42); and
(vi) $V_H$ CDR3 is selected from ATQGNYSLDF ("$V_H$ CDR 3.8"; SEQ ID NO:45) and ARGTGTY ("$V_H$ CDR 3.13"; SEQ ID NO:46);

(d) antibodies having a $V_L$ that corresponds in sequence to the $V_L$ of MAb5, MAb6, MAb7, MAb8, MAb9, MAb10, MAb11, MAb12, MAb13, MAb14, MAb21, MAb22 or MAb23 and a $V_H$ that corresponds in sequence to the $V_H$ of MAb5, MAb6, MAb7, MAb8, MAb9, MAb10, MAb11, MAb12, MAb13, MAb14, MAb21, MAb22 or MAb23; and (e) antibodies having a $V_L$ and a $V_H$ that correspond in sequence to the $V_L$ and $V_H$ that correspond in sequence to the $V_L$ and $V_H$ of MAb5, MAb6, MAb7, MAb8, MAb9, MAb10, MAb11, MAb12, MAb13, MAb14, MAb21, MAb22 or MAb23.

As will be appreciated by skilled artisans, anti-hPG antibodies useful in the diagnostic methods can be of any origin, including, for example, mammalian (e.g., human, primate, rodent, goat or rabbit), non-mammalian, or chimeric in nature (derived from more than one species of origin). Antibodies suitable for therapeutic uses in animals, including humans, are preferably derived from the same species intended to be treated, or have been modified or designed to be non-immunogenic or have reduced immunogenicity in the animal being treated. A specific class of anti-hPG antibodies useful for therapeutic uses in humans is the class of humanized antibodies, discussed in more detail, below. Anti-hPG antibodies useful in the methods and kits described herein can also be of, or derived from, any isotype, including, for example, IgA (e.g., IgA1 or IgA2), IgD, IgE, IgG (e.g., IgG1, IgG2, IgG3 or IgG4) or IgM. Anti-hPG antibodies designed for therapeutic uses are preferably of the IgG isotype.

In some embodiments, anti-hPG antibodies useful for therapeutic methods described herein are humanized. In general, humanized antibodies comprise substantially all of at least one, and typically two, variable domains, in which all or substantially all of the CDR regions correspond to those of a non-human immunoglobulin and all or substantially all of the framework regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods for humanizing antibodies, including methods for designing humanized antibodies, are well-known in the art. See, e.g., Lefranc et al., 2003, Dev. Comp. Immunol. 27:55-77; Lefranc et al., 2009, Nucl. Acids Res. 37:D1006-1012; Lefranc, 2008, Mol. Biotechnol. 40: 101-111; Riechmann et al., 1988, Nature 332:323-7; U.S. Pat. Nos. 5,530,101, 5,585,089, 5,693,761, 5,693,762 and 6,180,370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814;

Roguska et al., 1994, Proc. Natl. Acad. Sci. 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in TABLE 1A and the various C-terminal anti-hPG monoclonal antibodies provided in TABLE 1B, can be obtained using these well-known methods. Projected sequences for humanized $V_L$ and $V_H$ chains of selected anti-hPG antibodies are provided in TABLES 1A and 1B. Specific examples of humanized antibodies include antibodies comprising:

(a) any three $V_L$ CDRs and any three $V_H$ CDRs disclosed herein;

(b) a heavy chain variable region comprising an amino acid sequence corresponding to SEQ ID NO:21 and a light chain variable region comprising an amino acid sequence corresponding to SEQ ID NO:22;

(c) a heavy chain variable region comprising an amino acid sequence corresponding to SEQ ID NO:23 and a light chain variable region comprising an amino acid sequence corresponding to SEQ ID NO:24;

(d) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(e) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(f) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (g) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 15.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming a hPG:labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 15.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 15, by at least 50%, at a test antibody concentration in the range of 0.01-100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable.

Antibodies of the present disclosure can also be derivatized, covalently modified, or conjugated to other molecules to alter their properties or improve their function. For example, but not by way of limitation, derivatized antibodies include antibodies that have been modified, e.g., by glycosylation, fucosylation, acetylation, pegylation, phosphorylation, amidation, formylation, derivatization by known protecting/blocking groups, linkage to a cellular ligand or other protein, etc. Alternatively, specific amino acids in the variable or constant regions can be altered to change or improve function. In one non-limiting example, amino acid residues in the Fc region of an antibody may be altered to increase the serum half-life of the antibody by increasing its binding to FcRn.

Anti-hPG monoclonal antibodies include antibodies labeled with a detectable moiety. Such a label can be conjugated directly or indirectly to an anti-hPG monoclonal antibody of the disclosure. The label can itself be detectable (e.g., radioisotope labels, isotopic labels, or fluorescent labels) or, in the case of an enzymatic label, can catalyze chemical alteration of a substrate compound or composition which is detectable. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions.

Although the various anti-hPG antibodies useful in the methods and kits described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')$_2$, Fab, Fv, vIgG, scFv fragments and surrobodies, rIgG, disulfide-stabilized Fv antibodies (dsFv), diabodies, triabodies, and single domain antibodies, such as a camelized antibody or nanobody.

Antibodies of the present disclosure can be produced according to any way known to those of ordinarily skill in the art. In one non-limiting example, antibodies may be obtained from natural sources, including from any species capable of producing antibodies, such as antibodies derived from humans, simians, chicken, goats, rabbits, and rodents (e.g., rats, mice, and hamsters). Other species are also possible. Antibodies may also be generated and isolated from systems that utilize genetic engineering or recombinant DNA technology, such as, but not limited to, expression of recombinant antibodies in yeast cells, bacterial cells, and mammalian cells in culture, such as CHO cells. Antibodies may also be fully or partially synthetic.

Monoclonal antibodies (MAb) of the present disclosure are not limited to antibodies produced through hybridoma technology. A monoclonal antibody is derived from a single clone, including any eukaryotic, prokaryotic, or phage clone, by any means available or known in the art. Monoclonal antibodies can be prepared using a wide variety of techniques known in the art including the use of hybridoma, recombinant, and phage display technologies, or a combination thereof.

7.8. Treatments for Breast Cancer

Treatments for breast cancer fall into several categories.

Surgery is considered when the breast cancer is limited to the breast, or breast and axillary lymph nodes. Surgical techniques effective to treat breast cancer include, but are not necessarily limited to lumpectomy, quadrantectomy, simple mastectomy, radical mastectomy, and modified radical mastectomy.

Radiation therapy may be used to kill breast cancer cells remaining after surgery. Radiation may be produced by a machine outside the body (external-beam radiation therapy), or it may be produced by a radioactive material placed in the body near cancer cells (internal radiation therapy, or brachytherapy).

Chemotherapy, hormone therapy and targeted therapy are non-limiting examples of systemic therapies that may be used as adjuvant therapies after surgery, or surgery and radiation, or as principal therapies against metastatic breast cancer which has spread beyond the breast into distant organs. Such therapies can be used alone or in combination with each other. An adjuvant therapy is one administered in order to kill cancer cells that may have survived surgery or radiation therapy.

Radiation therapy and/or surgery may also be used to treat metastatic breast cancer, such as to treat a small number of metastases in a certain area, to prevent bone fractures or blockage in the liver, or to provide relief of pain or other symptoms. Breast cancer mestastases that have spread to bone may be treated with external beam radiation therapy and/or bisphosphonates such as pamidronate (Aredia) or zoledronic acid (Zometa), along with calcium and vitamin D, to strengthen the bones.

Chemotherapy relies on drugs to kill or slow or stop the growth of breast cancer cells. A variety of chemotherapeutic agents that work through different mechanisms are available to treat breast cancer. Chemotherapy may be effective against metastatic breast cancer when administered systemically, but may also be administered in a more localized fashion, such as into the fluid surrounding the brain.

Exemplary chemotherapeutic agents that may be effective against breast cancer include folate antagonists, including methotrexate and pemetrexed; purine antagonists, including cladribine, clofarabine, fludarabine, 6-mercaptopurine, nelarabine, pentostatin; pyrimidine antagonists, including capecitabine, cytarabine, 5-fluorouracil, gemcitabine, hydroxyurea; biologic response modifiers, including interferon-alfa; bleomycin; DNA alkylating agents, including nitrosureas, carmustine, lomustine; DNA cross-linking drugs and alkylating agents, including bendamustine, chlorambucil, cyclophosphamide, ifosfamide, mechlorethamine (nitrogen mustard), melphalan, dacarbazine, temozolomide, procarbazine; asparaginase; antibiotics, including mitomycin; platinum complexes, including carboplatin, cisplatin, oxaliplatin; proteosome inhibitors, including bortezomib; spindle poisons, such as the taxanes (including docetaxel, paclitaxel) and the vincas (including vinblastine, vincristine, vinorelbine); topoisomerase inhibitors, such as the anthracyclines (including daunorubicin, daunomycin, doxorubicin, epirubicin), the camptothecines, (including irinotecan, topotecan), the podophyllotoxins (including etoposide, teniposide and mitoxantrone); tyrosine kinase inhibitors, (including erlotinib (Tarceva), gefitinib, imatinib, lapatinib, sorafenib, sunitinib). Other chemotherapeutic agents are also known.

Particular chemotherapeutic agents, and combinations thereof, known to be effective against breast cancer include but are not limited to CMF, which is a combination of cyclophosphamide, methotrexate and 5-fluorouracil; CAF (FAC), which is a combination of cyclophosphamide, doxorubicin and 5-fluorouracil; AC, which is a combination of doxorubicin and cyclophosphamide; EC, which is a combination of epirubicin and cyclophosphamide; TAC, which is a combination of docetaxe, doxorubicin and cyclophosphamide; AC→T, which is a combination of doxorubicin and cyclophosphamide followed by paclitaxel or docetaxel (Herceptin may be given with the paclitaxel or docetaxel for HER2/neu positive tumors); A→CMF, which is a combination of doxorubicin, followed by CMF; CEF (FEC), which is a combination of cyclophosphamide, epirubicin and 5-fluorouracil (this may be followed by docetaxel); TC, which is a combination of docetaxel and cyclophosphamide; TCH, which is a combination of docetaxel, carboplatin, and Herceptin for HER2/neu positive tumors.

Other chemotherapeutic agents that may be effective against breast cancer include cisplatin, vinorelbine, capecitabine, pegylated liposomal doxorubicin, gemcitibine, mitoxantrone, ixabepilone, and albumin-bound paclitaxel, and others.

Estrogen promotes the growth of about two-thirds of breast cancers, i.e., those containing estrogen receptors (ER-positive cancers) and/or progesterone receptors (PR-positive cancers). Thus, in patients with ER-positive and PR-positive breast cancers, hormone therapy seeks to block the effect of estrogen or to lower estrogen levels. Thus, hormone therapy entails administration of synthetic hormones or other drugs effective to block the production and/or activity of the body's natural hormones which could otherwise support or promote the growth of hormone-sensitive breast cancer cells.

Tamoxifen, toremifene and raloxifene are examples of selective estrogen receptor modulators (SERMs) and anti-estrogens that antagonize estrogen receptors in breast cancer cells. Fulvestrant, which acts to eliminate estrogen receptors, may be effective even if the breast cancer is no longer responsive to tamoxifen. Aromatase inhibitors work by stopping estrogen production, and include the drugs letrozole, anastrozole, and exemestane. Ovarian ablation may also be used to eliminate the main source of estrogens in pre-menopausal women. Permanent ovarian ablation can be done by surgically removing the ovaries. Ovarian ablation may also be effected with drugs known as luteinizing hormone-releasing hormone (LHRH) analogs, such as goserelin or leuprolide, which may be used alone or with tamoxifen as hormone therapy in pre-menopausal women. Megestrol acetate may be used in women whose cancers do not respond to the other hormone treatments. Use of androgens may also be considered. Other hormonal therapy agents are also possible, such as bicalutamide and flutamide.

Targeted therapy is directed to particular genes or gene products known to be involved in breast cancer. A specific type of targeted therapy is antibody therapy which involves administering an antibody, such as a monoclonal antibody, that directly or indirectly kills, slows or stops the growth of breast cancer cells. Such antibodies can function through a variety of distinct mechanisms. For example, certain antibodies can mark cancer cells for attack by the patient's immune system via antibody-dependent cell-mediated cytotoxicity (ADCC) or other mechanisms. Other antibodies bind to and alter or inhibit the function of antigens that cancer cells require for survival or growth. Other mechanisms are also possible. Antibodies can also be conjugated to radioactive or chemotoxic moieties capable of killing cancer cells after binding to the corresponding antigen expressed on the cancer cells.

Examples of targeted antibody therapy for breast cancer are the monoclonal antibodies trastuzumab and bevacizumab. Trastuzumab and similar antibodies target the HER2 gene product, whereas bevacizumab and similar antibodies target VEGF. Trastuzumab may be administered to women with HER2-positive cancers alone or in combination with chemotherapy, as well as with other treatments. Bevacizumab may be combined with the chemotherapy drug paclitaxel, as well as others.

Other types of targeted therapies include small molecule drugs, such as lapatinib. HER2-positive cancers that no longer respond to trastuzumab may respond to lapatinib, which may be given with the chemotherapy drug capecitabine, as well as others.

7.9. Therapeutic Methods Using Anti-PG Antibodies

The present disclosure provides for therapeutic methods comprising administering an anti-PG antibody in a composition to a subject for purposes of treating and preventing metastatic breast cancer, preventing recurrence of breast cancer and preventing growth of breast cancer stem cells. In certain embodiments the antibodies are specific for human progastrin ("hPG") and in other embodiments such antibodies are monoclonal antibodies.

According to certain of these embodiments, anti-PG antibodies as disclosed herein are administered in a composition to a subject in need of treatment for metastatic breast cancer in a therapeutically effective amount as a monotherapy or as a combination therapy. Such subjects include, but are not limited to those diagnosed with metastatic breast cancer. In certain embodiments of these methods, the antibodies are anti-hPG monoclonal antibodies.

According to other embodiments, anti-PG antibodies as disclosed herein are administered in a composition to a subject in need of prevention of metastatic breast cancer in a therapeutically effective amount as a monotherapy or as a combination therapy. Such subjects include, but are not limited to those determined to have primary breast cancer but in whom the cancer is not known to have spread to distant tissues or organs. In certain embodiments of these methods, the antibodies are anti-hPG monoclonal antibodies.

According to yet other embodiments, anti-PG antibodies as disclosed herein are administered in a composition to a subject in need of prevention for recurrence of metastatic breast cancer in a therapeutically effective amount as a monotherapy or as a combination therapy. Such subjects include, but are not limited to those who were previously treated for primary or metastatic breast cancer, after which treatment such cancer apparently disappeared. In certain embodiments of these methods, the antibodies are anti-hPG monoclonal antibodies.

According to other embodiments, anti-PG antibodies as disclosed herein are administered in a composition to a subject in need of inhibition of the growth of breast cancer stem cells in a therapeutically effective amount as a monotherapy or as a combination therapy. Such subjects include, but are not limited to those having a breast cancer the growth or metastasis of which is at least partly attributable to the presence within it of cancer stem cells. Other embodiments provide for methods of preventing or inhibiting the growth of breast cancer stem cells by contacting such stem cells with an amount of an anti-PG antibody composition effective to prevent or inhibit the growth of such cells. Such methods can be carried out in vitro or in vivo. In certain embodiments of these methods, the antibodies are anti-hPG monoclonal antibodies.

Neutralizing anti-PG antibodies will be the primary active agents in therapeutic antibody compositions, although non-neutralizing anti-PG antibodies may be present if their presence does not substantially inhibit the therapeutic efficacy of the neutralizing antibodies.

The subject to whom anti-PG antibody compositions can be administered may be a mammal such as a non-primate (e.g., cow, pig, horse, cat, dog, rat, etc.) or a primate (e.g., monkey, chimpanzee, ape or human). The subject can be a human, such as an adult patient or a pediatric patient.

For purposes of treating or preventing metastatic breast cancer or preventing breast cancer recurrence, anti-PG antibody compositions can be administered alone to subjects as a monotherapy, or as an adjunct to one or more primary therapies effective to treat or prevent metastatic breast cancer or to prevent breast cancer recurrence.

Thus, in certain embodiments of the present disclosure, anti-hPG antibody compositions can be administered to a subject in need of treating or preventing metastatic breast cancer as an adjunct to chemotherapy, as an adjunct to radiation therapy, as an adjunct to biological therapy, as an adjunct to hormone therapy, as an adjunct to surgical therapy, or as an adjunct to other types of antibody therapy effective to treat or prevent metastatic breast cancer. In yet other embodiments, anti-hPG antibody compositions can be administered to a subject in need of preventing recurrence of breast cancer as an adjunct to other therapies effective for preventing such recurrence.

As an adjunctive therapy, anti-hPG antibody compositions can be administered concurrently, successively, or separately with the primary therapy.

Anti-hPG antibody compositions and the primary therapy are administered concurrently when administered at the same time, even where the respective administrations overlap, but begin or end at different times. Non-limiting examples of concurrent administration is administration of an anti-hPG antibody composition at the same time a subject is receiving chemotherapy for metastatic breast cancer or undergoing surgical resection of a primary breast tumor.

Anti-hPG antibody compositions and the primary therapy are administered successively when administered to a subject on the same day, for example during the same clinic visit, but not concurrently. Successive administration can occur 1, 2, 3, 4, 5, 6, 7, 8 or more hours apart. The primary therapy may be administered first, followed by administration of the anti-hPG antibody composition. In an alternative embodiment, the anti-hPG antibody composition may be administered first, followed by the primary therapy.

Anti-hPG antibody compositions and the primary therapy are administered separately when they are administered to a subject on different days. In certain embodiments, the anti-hPG antibody composition and primary therapy can be administered in an interval of 1-day, 2-days, 3-days, 4-days, 5-days, 6-days, one-week, 2-weeks, 3-weeks or a month or more. As with successive administration, administration of the anti-hPG antibody composition can precede or follow the separate administration of the primary therapy.

In certain other embodiments of the present disclosure, an anti-hPG antibody composition and the primary therapy can be administered repeatedly in an alternating pattern, whether administered successively or separately.

In certain embodiments, administering an anti-hPG antibody composition as an adjunct to a primary therapy may yield a greater than additive, or synergistic, effect providing therapeutic benefit where neither therapy could alone be administered in an amount that would be therapeutically effective without incurring unacceptable side effects. Under these circumstances, the anti-hPG antibody composition and/or primary therapy can be administered in lower amounts, thereby reducing the possibility or severity of adverse effects. However, a synergistic effect is not required for adjunctive therapy with an anti-hPG antibody composition to be therapeutically effective.

7.10. Methods of Monitoring the Efficacy of Metastatic Breast Cancer Treatment

As noted above, patients diagnosed with primary and/or metastatic breast cancer have elevated plasma and/or serum levels of PG whereas the baseline level of PG in healthy individuals is negligible. PG plasma and/or serum levels in subjects with primary and/or metastatic breast cancer are measurable, and for metastatic breast cancer are about 25 pM or greater. Based on this observation, plasma and/or serum levels of PG can be used to, among other things, monitor the effectiveness of treatments for primary or metastatic breast cancer, detect and diagnose the presence of primary or metastatic breast cancer, and select subjects that might benefit from treatment with anti-PG antibodies.

Thus, the present disclosure provides methods of monitoring a subject being treated for breast metastatic cancer to determine the effectiveness of a prior round of therapy for metastatic breast cancer. These methods can be used for any type of therapy against metastatic breast cancer, used alone, or in combination with others, including but not limited to administration of an anti-hPG antibody composition, therapy with other types of antibodies, chemotherapy, radiation therapy, hormonal therapy, biological therapy and others. After a round of therapy is complete, the treatment team responsible for a subject's care needs to ascertain if it was effective to determine whether or not to administer a new round of treatment and make other clinical decisions.

In some embodiments of the monitoring methods, the concentration of PG in one or more bodily fluids, such as blood, plasma, serum or others, can be measured before a treatment for metastatic breast cancer is started and then compared to the level of PG measured in the same type of bodily fluid some time after treatment is complete. In other embodiments, PG levels in a tissue of interest, such as biopsies of a breast cancer, are measured.

A reduction in PG concentration is indicative of efficacy. Typically, the greater the extent of reduction in PG treatment post-treatment, the more efficacious was the therapy. Without wishing to be bound by any particular theory of operation, it is believed that as the number and/or size of metastases in a patient is reduced as a result of an efficacious treatment, the total amount of PG produced by the metastases also declines. By contrast, a lack of reduction or a rise in PG levels after treatment is complete may indicate that the therapy was not effective. Based on this information, the treatment team can decide whether to initiate a new round of therapy.

Suitable intervals after a round of therapy is complete before which time samples are taken for monitoring are readily determined by those of ordinary skill in the art, and depend on such variables as the type of therapy under consideration, gender and age of the subject and others. Exemplary intervals include 1, 2, 3, 4, 5, 6, 7, 8, 9, 10 or 11 weeks and 3, 4, 5 or 6 months after a round of therapy is complete before samples are taken for use in the monitoring methods of the present disclosure. Other intervals are also possible. In other embodiments, multiple measurements at different intervals after completion of therapy may be taken, and then graphed to determine if a trend exists. In a non-limiting example, PG levels can be determined weekly or monthly for the first six months after a round of therapy is concluded. Other intervals are also possible.

PG concentration levels in bodily fluids can be measured using analytical techniques familiar to those of ordinary skill in the art, such as, but not limited to, RIA and ELISA. Assay methods, such as these, that rely on antibodies specific for hPG can be carried out using non-neutralizing or neutralizing antibodies, such as those disclosed herein, in accordance with the knowledge of those of ordinary skill in the art.

In a specific embodiment, PG levels may be measured using a sandwich ELISA with one anti-PG antibody targeting the N-terminus of progastrin and a second anti-PG antibody targeting the C-terminus of progastrin. Exemplary N- and C-terminal anti-PG antibodies useful for such a sandwich assay are described in a later section. In such an assay, surface, such as the wells in a 96-well plate, is prepared to which a known quantity of a first, "capture," N-terminal or C-terminal anti-PG antibody is bound. A test sample is then applied to the surface followed by an incubation period. The surface is then washed to remove unbound antigen and a solution containing a second, "detection," anti-PG antibody is applied, where the detection antibody binds a different epitope of PG (for example, if the capture antibody is a C-terminal anti-PG antibody, an N-terminal anti-PG antibody is used as the detection antibody, and vice versa). PG levels are then measured either directly (if, for example, the detection antibody is conjugated to a detectable label) or indirectly (through a labeled secondary antibody that binds the detection anti-PG antibody). A specific sandwich assay for measuring plasma and/or serum PG levels is provided in Example 11.

In an alternative embodiment of the methods of the present disclosure, the efficacy of administration of an anti-hPG antibody composition to a subject in reducing PG levels in a bodily fluid of interest may be monitored. In these methods, samples may be taken over time and PG concentrations graphed to assess trends. Where residual anti-hPG antibodies are present, the data may show a reduction in PG levels due to sequestration of PG by the antibodies, followed by a rise as this effect abates, followed by a subsequent decline if the treatment was effective to treat metastatic breast cancer.

According to other embodiments of the methods of the present disclosure, a blood, serum or plasma PG concentration below a predetermined threshold of less than about 50 pM, 40 pM, 30 pM, 20 pM, 10 pM, 5 pM, 2 pM, 1 pM or less is indicative of efficacy for treating metastatic breast cancer. Other PG concentration thresholds indicative of efficacy are also possible and are readily determined by those of ordinary skill in the art.

7.11. Methods of Determining the Presence of Breast Cancer

The present disclosure also provides certain embodiments according to which subjects may be tested to determine if they have elevated PG levels in a bodily fluid, such as blood, plasma, serum, or others, compared to an appropriate baseline, for purposes of detecting the presence of breast cancer or recurrence of breast cancer after treatment.

In certain embodiments of the methods of the present disclosure, the subject may be one for whom it is desired to be determined whether breast cancer, primary or metastatic, is present in the subject. In such subjects, elevated PG levels relative to baseline indicates that breast cancer is present. Without wishing to be bound by any particular theory of operation, it is believed that as the size and/or extent of breast cancer in a subject increases, systemic and/or localized PG levels also increase in the subject.

In other embodiments, the subject may be one previously treated for primary breast cancer for whom it is desired to be determined whether the breast cancer has metastasized to distant tissues or organs. In such subjects, elevated PG levels relative to baseline indicates that metastatic breast cancer is present. For such subjects as well, the methods of the present disclosure are useful, among other things, for determining whether or not a treatment intended to prevent metastatic breast cancer was effective. Without wishing to be bound by any particular theory of operation, it is believed that as the number and/or size of metastases in a subject increases, systemic and/or localized PG levels also increase in the subject.

According to yet other embodiments, the subject may be one previously treated for breast cancer, primary or metastatic, in whom the cancer apparently disappeared and in whom it is desired to be determined whether breast cancer has recurred or come back. In such subjects, elevated PG levels relative to baseline indicates that breast cancer has recurred. Without wishing to be bound by any particular theory of operation, it is believed that as the size and/or extent of recurrent breast cancer in a subject increases, systemic and/or localized PG levels also increase in the subject.

In view of the discoveries described herein that certain primary and metastatic breast cancers secrete PG and that certain breast cancer cells are PG-sensitive, the present disclosure also provides methods of selecting subjects that may benefit from therapy by administering anti-PG antibodies. Thus, subjects may be screened by care providers to detect if they have elevated blood PG levels relative to a baseline. Once such subjects are identified, care providers can order additional tests, such as mammography, to confirm the presence of breast cancer in the subject. If breast cancer is confirmed then treatment, including administration of anti-hPG antibodies, can be commenced.

In certain embodiments of the methods for selecting subjects, screening may be performed as part of a routine check up by the subject's primary care physician or as part of public health initiatives that target larger populations of subjects. In other embodiments, the subjects to be screened are members of particular subpopulations with higher then average risk of developing breast cancer. Such groups include, but are not limited to, subjects having mutations in the BRCA1 gene, the BRCA2 gene, or other genes associated with increased risk of breast cancer. Other groups include subjects with non-malignant breast abnormalities, such as ductal carcinoma in situ (DCIS) or lobular carcinoma in situ (LCIS), subjects having a first degree relative (sister, mother, daughter) diagnosed with breast cancer, subjects exposed to chest irradiation, subjects that experienced early menarche, late menopause, or late age for first birth, subjects that used birth control pills, subjects having high body mass index, or subjects having a high-fat diet or that consume alcohol. Yet other groups include subjects formerly diagnosed and successfully treated for breast cancer.

In yet other embodiments of the methods of selecting subjects, the subjects to be screened are those who received results of a diagnostic test for breast cancer that do not definitively rule in or rule out the presence of breast cancer. Screening for elevated PG levels can provide additional information to be used by care providers to improve the accuracy of a diagnosis. One non-limiting example of such subjects would be those receiving the result of an inconclusive, ambiguous or difficult to read mammogram.

PG concentrations can be measured using techniques familiar to those of ordinary skill, such as, but not limited to, RIA and ELISA. Assay methods, such as these, that rely on antibodies specific for hPG can be carried out using non-neutralizing or neutralizing antibodies, such as those disclosed herein, in accordance with the knowledge of those of ordinary skill in the art.

Based on the detection of elevated PG levels using the methods of the present disclosure, the treatment team can then decide whether to undertake additional tests to confirm the presence of breast cancer or recurrence of breast cancer after treatment, or proceed directly to treating the subject.

Different baselines may be used against which to compare PG levels measured in a subject. In some embodiments of the methods of the present disclosure, the baseline is established by measuring PG levels in a bodily fluid of interest sampled from the same subject at prior times. Such samples may be taken, and PG levels measured, at predetermined intervals. In a non-limiting example, PG levels are measured weekly or monthly for the first six months after the end of a treatment, then once every three months until the second anniversary of the end of the treatment, and then every six months or year thereafter. Other predetermined intervals are also possible.

In other embodiments of the methods of the present disclosure, the baseline can be established from average PG levels in a population of individuals with characteristics similar to those of the subject undergoing sampling for detection of breast cancer or breast cancer recurrence. Such characteristics may include but are not necessarily limited to sex, age, stage of the primary breast tumor, prior exposure to certain treatments, or combinations of these or other factors. In yet other embodiments, both a subject-specific baseline, as well as a population-derived baseline can be used in assessing the condition of a subject.

In accordance with the knowledge of those ordinarily skilled in the art, PG levels in samples from a subject that exceed a certain threshold relative to a baseline are concluded as having breast cancer, breast cancer that has recurred after treatment or a subject that might gain therapeutic benefit from treatment with anti-hPG antibodies. The treatment team may then undertake confirmatory tests to confirm presence of breast cancer or recurrent breast cancer. Non-limiting examples of such tests include exploratory surgery, imaging techniques such as mammography and tests for the presence in blood or other tissues of biological factors produced by breast cancers.

Because eating usually increases gastrin synthesis and secretion, eating may result in transient increases in blood PG levels which may interfere with the accurate measurement of PG produced by breast cancer metastases or recurrent breast cancer. To avoid this effect, particularly where PG levels in plasma and/or serum is to be determined, samples can be taken from subjects after fasting for sufficient time, as can readily be determined by those of ordinary skill in the art.

7.12. Pharmaceutical Compositions

Anti-hPG antibodies for use in the methods of the present disclosure can be formulated as compositions. Optionally, the compositions can comprise one or more additional therapeutic agents, such as chemotherapeutic agents or other antibodies with therapeutic efficacy against metastatic breast cancer or breast cancer recurrence. The compositions will usually be supplied as part of a sterile, pharmaceutical composition that will normally include a pharmaceutically acceptable carrier. This composition can be in any suitable form depending upon the desired method of administering it to a patient.

The anti-PG antibodies can be administered to a subject by a variety of routes, typically parenterally, for example, via subcutaneous, intravenous, intraperitoneal or intramuscular injection. Administration can be effected as one or more bolus injections, or as one or more infusions. Other routes of administration are also possible in accordance with the knowledge of those ordinarily skilled in the art. The most suitable route for administration in any given case may depend on the particular composition to be administered and characteristics of the subject, such as age or sex.

Pharmaceutical compositions can be conveniently presented in unit dose forms containing a predetermined amount of an anti-hPG antibody of the disclosure per dose. Such a unit can contain for example but without limitation 5 mg to 5 g, for example 10 mg to 1 g, or 20 to 50 mg. Pharmaceutically acceptable carriers for use in the disclosure can take a wide variety of forms depending, e.g., on the route of administration.

Pharmaceutical compositions of the disclosure can be prepared for storage as lyophilized formulations or aqueous solutions by mixing the antibody having the desired degree of purity with optional pharmaceutically acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, *Remington's Pharmaceutical Sciences,* 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml. Surfactants have a tendency, however, to bind to antibodies, and can compromise their conformations. Therefore, when used, stabilizing concentrations should be low and discerned experimentally.

Additional miscellaneous excipients can include chelating agents (e.g., EDTA), antioxidants (e.g., ascorbic acid, methionine, vitamin E), and cosolvents.

Anti-hPG antibodies can be administered singly or as mixtures of one or more anti-hPG antibodies alone, or in mixture or combination with other agents useful for preventing breast cancer metastasis or recurrence, including but not limited to chemotherapeutic agents, hormonal therapy agents, biological therapy agents, and antibody therapy agents (e.g., bevacizumab).

7.13. Pharmaceutical Kits

In certain embodiments, the invention provides for pharmaceutical kits for use by clinicians or others. The pharmaceutical kit is a package comprising an anti-hPG antibody of the disclosure (e.g., either in lyophilized form or as an aqueous solution) and one or more of the following: at least a second therapeutic agent as described elsewhere in this disclosure; a device for administering the anti-hPG antibody, e.g., a needle and/or syringe; and pharmaceutical grade water or buffer to resuspend or dilute the antibody if the antibody is in lyophilized or concentrated form. Kits may also include instructions for preparing the antibody composition and/or administering the composition to a patient.

Each unit dose of the anti-hPG antibody composition can be packaged separately, and a kit can contain one or more unit doses (e.g., two unit doses, three unit doses, four unit doses, five unit doses, seven unit doses, eight unit doses, ten unit doses, or more). In one embodiment, the one or more unit doses are each housed in a syringe, and in another embodiment, the one or more unit doses are each contained in a bag or similar receptacle suitable for connecting to an I.V. line.

7.14. Effective Dosages

Compositions comprising neutralizing anti-hPG antibodies of the present disclosure are generally to be administered to a subject in need of treating or preventing breast cancer metastasis or preventing recurrence of breast cancer in a dosage effective to achieve, at least partially, the desired outcome.

With respect to treating breast cancer metastasis, therapeutic benefit means, among other things, any amelioration of metastatic breast cancer, halting or slowing the growth of breast cancer metastases, reducing the number and/or size of such metastases within a subject, reducing blood flow to breast cancer metastases, reducing the metabolism of breast cancer metastases, reducing the severity of breast cancer metastatic cancer, inhibiting the proliferation of or increasing apoptosis of metastatic breast cancer cells, halting or delaying aggravation of the symptoms or signs associated with metastatic breast cancer in a subject, allowing surgical resection of breast cancer metastases where such resection would not have been possible before treatment, increasing the life expectancy, comfort or quality of life of a subject having metastatic breast cancer, or reducing pain in such a subject. A complete cure of metastatic breast cancer, while desirable, is not required for therapeutic benefit to exist.

Metastatic breast cancer tumor size, number and metabolism can be measured using various scanning techniques, including, but not limited to, CT, MRI, functional MRI, SPECT and PET, as well as other methods known to those of ordinary skill in the art.

Therapeutic benefit can also be correlated with one or more surrogate end points. By way of example, not limitation, production of certain proteins or other factors by metastatic breast cancers, such as progastrin or carcinoembryonic antigen (CEA), can be measured in a subject over time with a reduction in levels of the factor being indicative of therapeutic benefit.

With respect to preventing breast cancer metastasis, an effective dosage is one that is effective to at least partially prevent metastatic breast cancer, as evidenced by, among other things, absence of breast cancer metastases, delaying, halting or slowing the growth of breast cancer metastases, reducing the number and/or size of any breast metastases that ultimately might occur, and inhibition of or interference with any of the mechanistic steps by which metastatic breast cancer cells are able to spread from the primary tumor. Complete prevention of breast cancer metastasis, while desirable, is not required for efficacy to exist.

With respect to preventing breast cancer recurrence, an effective dosage is one that is effective to at least partially prevent recurrence of breast cancer, as evidenced by, among other things, absence of breast cancer recurrence, maintaining remission of breast cancer, or delaying, halting or slowing the reappearance or regrowth of breast cancer, or growth of a new breast tumor, in a subject after treatment where the initial breast cancer became undetectable or apparently disappeared. Efficacy for preventing recurrence of breast cancer is also evidenced by, among other things, the killing of breast cancer stem cells, delaying, halting, inhibiting or slowing the growth or proliferation of breast cancer stem cells, increasing breast cancer stem cell apoptosis, or causing the differentiation of breast cancer stem cells into cells not capable of contributing to the formation or growth of breast cancer. As described elsewhere herein, breast cancer stem cells are identifiable as having one or more phenotypic attributes characteristic of such cells including, but not limited to, expression of certain cell markers, ability to grow as spheroids under low adherence culture conditions and the ability to initiate new tumor growth after transplantation. Complete prevention of recurrence of breast cancer, while desirable, is not required for efficacy to exist.

Binding all progastrin is not necessarily required to achieve therapeutic efficacy. Rather, reducing the concentration of progastrin within a tumor, systemically, in particular body fluids, such as ascites fluid, fluid from pleural effusions, cerebrospinal fluid, lymph, blood, plasma, serum, or elsewhere, may also be effective.

In accordance with the knowledge of those ordinarily skilled in the art, the dose of an anti-hPG antibody composition can be titrated in a patient so as to reduce the free hPG concentration in a tissue or body fluid of interest at a predetermined time after administration at least about 10%, 20%, 30%, 40%, 50%, 60%, 70%, 80%, 90, or 100%, or about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-95%, or a percentage reduction in free hPG concentration ranging between any of the foregoing values.

The amount of anti-hPG antibody administered will depend on a variety of factors, including the size and weight of the subject to be treated, the form, route and site of administration, the therapeutic regimen (e.g., whether a second therapeutic agent is used), the age and condition of the particular subject being treated, the level of PG detected in the blood of said subject prior to treatment, the sensitivity of the subject being treated with anti-PG antibodies. The appropriate dosage can be readily determined by a person skilled in the art. Ultimately, a clinician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using the methods of the present disclosure or other methods known to those of ordinary skill in the art.

Effective dosages can be estimated initially from in vitro assays. For example, an initial dose for use in animals may be formulated to achieve a circulating blood or serum concentration of anti-hPG antibody that is at or above the binding affinity of the antibody for progastrin as measured in vitro. Calculating dosages to achieve such circulating blood or serum concentrations taking into account the bioavailability of the particular antibody is well within the capabilities of skilled artisans. For guidance, the reader is referred to Part 1: General Principles in "*Goodman and Gilman's The Pharmacological Basis of Therapeutics*," 11$^{th}$ Ed., Hardman, J. G., et al., Eds., McGraw-Hill Professional, and the references cited therein. Initial dosages can also be estimated from in vivo data, such as animal models. Ordinarily skilled artisans can routinely adapt such information to determine dosages suitable for human administration.

In specific embodiments, an i.v. dose may be determined for an individual subject by measuring the serum or plasma PG concentration of the individual a few times a few days to a few weeks prior to treatment and calculating an amount of anti-PG antibody that would be saturating, i.e., an amount that would be sufficient to bind all of the PG. As will be appreciated by skilled artisans, the amount of any specific antibody necessary to achieve saturation for a given serum or plasma concentration of PG will depend, in part, on the affinity constant of the particular antibody. Methods for calculating saturating quantities for specific anti-PG antibodies of interest are well-known.

To insure saturation, an amount that is greater than the calculated saturating amount may be administered, for example, at least 2-, 3-, 4-, 5-, 6-, 7-, 8-, 9- or even 10-fold greater than the calculated saturating amount may be administered. For modes of administration other than i.v., the amount can be adjusted based upon pharmacokinetic and bioavailability, as is well known in the art.

The effective dose of an anti-hPG antibody composition can range from about 0.001 mg/kg to about 250 mg/kg per single (e.g., bolus) administration, multiple administrations or continuous (e.g., infusion) administration, or any effective range or value therein depending on the type of cancer the recurrence of which is sought to be prevented, the route of administration and the age, weight and condition of the subject. In certain embodiments, each dose can range from about 0.1 mg/kg to about 0.5 mg/kg; about 0.25 mg/kg to about 0.75 mg/kg; about 0.5 mg/kg to about 1 mg/kg; about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg; about 70 mg/kg to about 80 mg/kg; about 75 mg/kg to about 85 mg/kg; about 80 mg/kg to about 90 mg/kg; about 85 mg/kg to about 95 mg/kg; about 90 mg/kg to about 100 mg/kg; about 95 mg/kg to about 105 mg/kg; about 100 mg/kg to about 150 mg/kg; about 125 mg/kg to about 175 mg/kg; about 150 mg/kg to about 200 mg/kg; about 175 mg/kg to about 225 mg/kg; about 200 mg/kg to about 250 mg/kg. Other dosage ranges are also possible.

Amount, frequency, and duration of administration will depend on a variety of factors, such as the patient's age, weight, and disease condition. Thus, in non-limiting examples, a therapeutic regimen for administration can continue for 1 day or more, 2 days or more, 3 days or more, 4 days or more, 5 days or more, 6 days or more, 1 week or more, 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of anti-hPG antibody can be administered as a single dose or over the course of a therapeutic regimen, e.g., over the course of a week, two weeks, three weeks, one month, three months, six months, one year, or longer.

8. EXAMPLES

Example 1

Expression of Gastrin Gene in Metastatic Breast Cancer Cell Lines

This example describes the expression of the gastrin (GAST) gene in metastatic breast cancer cell lines.

A. Methods

Expression of the GAST mRNA was quantified using quantitative RT-PCR from RNA preparations from MCF-7, MDA-MB-231 and T47D cell lines. Data is expressed in comparison with the mRNA expression level found in the SW480 cell line, a primary colorectal cancer cell line known to express high levels of gastrin mRNA.

MCF-7 cells are a human metastatic breast cancer cell line. They were originally derived from a pleural effusion of a patient diagnosed with adenocarcinoma of the breast. MDA-MB-231 cells are a human metastatic breast cancer cell line. They were originally derived from a pleural effusion of a patient diagnosed with adenocarcinoma of the breast. T47D cells are a human metastatic breast cancer cell line. They were originally derived from a pleural effusion of a patient diagnosed with an infiltrating ductal carcinoma of the breast.

B. Results

The gastrin gene expression levels measured by quantitative RT-PCR are shown in FIG. 1. All three metastatic cancer cell lines tested expressed the gastrin gene at levels about the same level or less compared to expression in SW480 cells. Through post-translational processing, the gastrin gene product may be converted into progastrin.

Example 2

Expression of Gastrin Gene in Primary and Metastatic Breast Tumors Surgically Removed from Patients This example describes the expression of the gastrin (GAST) gene in primary and metastatic breast cancers surgically removed from patients.

A. Methods

Primary and metastatic breast cancers were surgically resected from different patients in accordance with applicable ethical guidelines. RNA was prepared from the cancer samples and gastrin mRNA was measured by quantitative RT-PCR. Expression of gastrin mRNA in the clinical samples was normalized relative to the level of expression in MCF-7 cells.

B. Results

A total of 105 primary breast cancers and 25 metastatic breast cancers were tested for expression of the gastrin gene. Progastrin mRNA was detectable in 27 of the primary tumors tested (FIG. 2) and in 7 of the metastatic tumors tested (FIG. 3). Thus, the gastrin gene is expressed in an subset of both primary and metastatic breast cancers and the level of expression varies among the cancers in which expression of the gastrin gene is detectable.

Example 3

Blood Plasma Progastrin Concentrations in Breast Cancer Patients

This example describes quantification of blood plasma levels of progastrin in patients with primary and metastatic breast cancer.

A. Methods

Blood plasma progastrin concentrations were measured in healthy individuals, as a control, and in 42 patients with metastatic breast cancer from whom the primary tumors had been surgically removed and in 3 patients with primary breast cancer. A total of 104 healthy control samples were obtained from a blood bank.

Quantification of plasma or serum progastrin levels was performed using a progastrin-specific sandwich ELISA technique similar to the one described prophetically below.

The wells of Nunc MaxiSORP 96-well plates are coated with a first progastrin-specific antibody as follows. Anti-progastrin polyclonal antibodies specific for the carboxy-terminal region of progastrin are diluted to a concentration of 3 μg/ml in a solution of 50 mM, pH 9.6 sodium carbonate/bicarbonate buffer in MilliQ water. A total of 100 μl of the antibody solution is then added to each well of the 96-well plates, and incubated overnight at 4° C. After binding, the antibody solution is removed from the wells, which are then washed three times with 100 μl wash buffer (1×PBS/0.1% Tween-20). A total of 100 μl blocking buffer (1×PBS/0.1% Tween-20/0.1% BSA) is then added to each well and incubated for 2 hours at 22° C. Blocking buffer is then removed and the wells washed three times with wash buffer. Plasma or serum samples isolated from patients is then added to the wells in a volume of 100 μl in a dilution series, typically 1:1, 1:2, 1:5 and 1:10 dilutions, and is then incubated for 2 hours at 22° C. Plasma or serum samples are analyzed in duplicate.

Assays also include two standard curves. The first standard curve is prepared using dilutions of recombinant progastrin to a final amount of 1 ng, 0.5 ng, 0.25 ng, 0.1 ng, 0.05 ng, 0.01 ng, and 0 ng per well. The second standard curve, which serves as a negative control, is prepared from progastrin-negative human serum diluted in blocking buffer at the same dilutions as the test samples, i.e., 1:1, 1:2, 1:5 and 1:10. Alternatively, when plasma samples are being assayed, the second standard curve, which serves as a negative control, is prepared from progastrin-negative human plasma diluted in blocking buffer at the same dilutions as the test samples, i.e., 1:1, 1:2, 1:5 and 1:10.

After incubation with the plasma or serum samples is complete, the well contents are removed and the wells are washed three times with wash buffer, 100 μl/well, after which progastrin bound to the first antibody is detected using a second antibody specific for progastrin, as follows.

Biotin-coupled anti-progastrin polyclonal or monoclonal antibodies specific for the amino-terminal region of progastrin are diluted in blocking buffer to a concentration of 0.1 to 10 μg/ml, depending on the antibody. A total of 100 μl of the antibody solution is then added to each well, and incubated for 1 hour at 22° C.

After secondary antibody binding is complete, the plates are washed three times with wash buffer, 100 μl/well, after which 100 μl of a solution of streptavidin-HRP (25 ng/ml in blocking buffer) is added to each well and incubated for 1 hour at 22° C. After incubation with the streptavidin-HRP solution is complete, the plates are washed three times with wash buffer, 100 μl/well. Thereafter, 100 μl of chemiluminescent substrate prepared using a Pierce SuperSignal ELISA Femto Maximum Sensitivity Chemiluminescent Substrate kit, is added per well, incubated for 5 min at room temperature in the dark, and then read on a luminometer.

Based on the luminometer readings, linear regression analysis is used to derive the equation of the lines corresponding to the standard curve data. Using this equation, the concentration of progastrin in the various patient samples is then calculated.

B. Results

The box plots in FIG. 4 show the $25^{th}$ percentile, median, and $75^{th}$ percentile blood plasma progastrin concentrations in the breast cancer patients having metastatic breast cancer compared to healthy controls. The whiskers indicate the 5th and 95th percentiles of blood plasma progastrin concentrations. This data demonstrates that patients with metastatic breast cancer from whom primary breast cancer tumors were removed had higher median blood plasma progastrin concentrations than that of healthy individuals. Statistical analysis of the data is contained in Table 4.

In the three patients diagnosed with primary breast cancer without metastases the progastrin levels were determined to be 45.7 pM, 97.3 pM and 667.7 pM, demonstrating that progastrin levels are also elevated in certain patients with primary breast cancer.

TABLE 4

| Table Analyzed<br>Column A<br>vs<br>Column D<br>Mann Whitney test | Breast cancer<br>Controls<br>vs<br>T–M+ |
|---|---|
| P value | <0.0001 |
| Exact or approximate P value? | Gaussian Approximation |
| P value summary | *** |
| Are medians signif. different? (P < 0.05) | Yes |
| One-or two-tailed P value? | Two-tailed |
| Sum of ranks in column A, D | 5900, 1976 |
| Mann-Whitney U | 439.5 |

Example 4

Effect of Anti-Progastrin Polyclonal Antibodies on Growth of MDA-MB-231 Metastatic Breast Cancer Cells in Culture This example describes the effect of anti-progastrin polyclonal antibodies on the growth of MDA-MB-231 cells in culture.

A. Methods

MDA-MB-231 cells were seeded into 6-well plates (50,000 cells/well) in RPMI medium plus 10% FBS, incubated for one day, and then serum-starved overnight. The medium was then replaced twice daily for 48 hours with RPMI medium supplemented with 0.5% Pannexin H containing 2 μg/ml of a control antibody or an anti-progastrin polyclonal antibody in triplicate. The control antibody was polyclonal rabbit anti-human IgG, Affinity BioReagents Ref #SA1-600, 2 μg/ml. The experiment was carried out in duplicate and the technician was blinded as to the contents of the treatment solutions. At the end of the experiment, cells from each well were counted three times.

B. Results

The results, shown in FIG. 5, were calculated as the average number of cells per well at the end of the experiment minus the number of cells seeded at the beginning of the experiment. Statistical analysis of the data is contained in Table 5. The results of this experiment demonstrate that the anti-progastrin polyclonal antibodies are effective to reduce the growth of MDA-MB-231 metastatic breast cancer cells in vitro, compared to control polyclonal antibodies.

TABLE 5

| | |
|---|---|
| Table Analyzed | MDA-MB-231 |
| Column D | anti-PG PAb-T0 |
| vs | vs |
| Column E | CT PAb-T0 |
| Mann Whitney test | |
| | |
| P value | 0.0139 |
| Exact or approximate P value? | Gaussian Approximation |
| P value summary | * |
| Are medians signif. different? ($P < 0.05$) | Yes |
| One-or two-tailed P value? | One-tailed |
| Sum of ranks in column D, E | 481, 695 |
| Mann-Whitney U | 181.0 |

Example 5

Effect of Anti-Progastrin Monoclonal Antibodies on Growth of MDA-MB-231 Metastatic Breast Cancer Cells in Culture This example describes the effect of anti-progastrin monoclonal antibodies on the growth of MDA-MB-231 cells in culture.

A. Methods

In a first experiment employing MAb3 and MAb8, MDA-MB-231 cells were seeded into 6-well plates (50,000-150,000 cells/well) in RPMI medium plus 10% FBS, incubated for 8 hours, and then serum-starved overnight. Starting 24 hours after seeding (time "T0"), the medium was replaced twice daily for 48 hours with RPMI medium supplemented with 0.5% Pannexin H containing 1-10 µg/ml of anti-hPG monoclonal antibody or a control monoclonal antibody (mouse anti-human IgG1). At T0, the number of cells was counted in three wells for each experiment. Forty-eight hours later, the number of cells surviving in each well was counted four times in blinded fashion. Cell counts at T0 were subtracted from cell counts at 48 hours and data normalized as a percentage relative to the number of cells surviving treatment with control antibody.

In a second experiment, MDA-MB-231 cells were seeded into 6-well plates (100,000 cells/well) and treated with MAb8, MAb13, MAb16 and MAb19 (10 µg/ml) as above.

B. Results

The results of the experiments, shown in FIG. 6 and FIG. 7, demonstrate that five different anti-hPG antibodies, MAb3, MAb8, MAb13, MAb16 and MAb19 are effective to inhibit the growth of MDA-MB-231 metastatic breast cancer cells in vitro compared to control monoclonal antibodies. The inhibitory effect of MAb8 was dose responsive. MAb8 and MAb13 recognize C-terminal epitopes of hPG, whereas MAb3, MAb 16 and MAb19 each recognize N-terminal epitopes demonstrating that antibody neutralizing activity is not dependent on whether the target epitope is located at the N-terminus or C-terminus of the progastrin protein.

Example 6

Effect of Anti-Progastrin Monoclonal Antibodies on Growth of MCF-7 Metastatic Breast Cancer Cells in Culture This example describes the effect of anti-progastrin monoclonal antibodies on the growth of MCF-7 cells in culture.

A. Methods

MCF-7 cells were seeded into 6-well plates (100,000 cells/well) and grown in DMEM containing 10% fetal calf serum for 8 hours. Cells were serum-starved overnight, and starting at 24 hours after seeding (time T0), cells were treated every 12 hours for 48 hours, in the presence of 0.5% PanexinH, with 1 µg/ml of control monoclonal antibody (mouse anti-human IgG1, Calbiochem Ref #411451) or with 1 µg/ml anti-hPG MAb3 as indicated. The number of live cells in both control MAb and anti-hPG MAb treated cells was counted at 48 hours. Cell counts at the start of the treatment (T0) were subtracted from test and control cell counts measured at 48 hours. The technician was blinded as to the contents of the treatment solutions.

B. Results

The results, shown in FIG. 8, were calculated as the average number of cells per well at the end of the experiment minus the number of cells seeded at the beginning of the experiment. Statistical analysis of the data is contained in Table 6. The results of this experiment demonstrate that the anti-progastrin monoclonal antibodies are effective to reduce the growth of MCF-7 metastatic breast cancer cells in vitro, compared to control antibodies.

TABLE 6

| | |
|---|---|
| Table Analyzed | MCF-7 |
| Column D | anti-PG MAb3-T0 |
| vs | vs |
| Column E | CT MAb-T0 |
| Mann Whitney test | |
| | |
| P value | 0.0194 |
| Exact or approximate P value? | Gaussian Approximation |
| P value summary | * |
| Are medians signif. different? ($P < 0.05$) | Yes |
| One-or two-tailed P value? | Two-tailed |
| Sum of ranks in column D, E | 109, 191 |
| Mann-Whitney U | 31.00 |

Example 7

Effect of Anti-Progastrin Monoclonal Antibodies on Growth of T47D Metastatic Breast Cancer Cells in Culture This example describes the effect of anti-PG monoclonal antibodies on the growth of T47D cells in culture.

A. Methods

T47D cells were seeded into 6-well plates (50,000 cells/well) and grown in RPMI containing 10% fetal calf serum for 8 hours. Cells were serum-starved overnight, and starting at 24 hours after seeding (time T0), cells were treated every 12 hours for 48 hours, in the presence of 0.5% PanexinH, with 1 µg/ml of control monoclonal antibody (mouse anti-human IgG1, Calbiochem Ref #411451) or with 1 µg/ml anti-hPG MAb3 as indicated. The number of live cells in both control MAb and anti-hPG MAb treated cells was counted at 48 hours. Cell counts at the start of the treatment (T0) were subtracted from test and control cell counts measured at 48 hours. The technician was blinded as to the contents of the treatment solutions.

B. Results

The results, shown in FIG. 9, were calculated as the average number of cells per well at the end of the experiment minus the number of cells seeded at the beginning of the experiment. Statistical analysis of the data is contained in Table 7. In this experiment, no statistically significant difference was found in the effect on T47D cell growth in vitro by treatment with the anti-progastrin monoclonal antibody MAb3 compared to a control antibodies.

TABLE 7

| Table Analyzed | T47D |
| --- | --- |
| Column D | CT MAb-T0 |
| vs | vs |
| Column E | anti-PG MAb-T0 |
| Mann Whitney test | |
| P value | 0.1248 |
| Exact or approximate P value? | Gaussian Approximation |
| P value summary | ns |
| Are medians signif. different? (P < 0.05) | No |
| One-or two-tailed P value? | One-tailed |
| Sum of ranks in column D, E | 108.5, 144.5 |
| Mann-Whitney U | 42.50 |

Example 8

Effect of Low Adherence Culture Conditions on Expression of the Gastrin Gene in Metastatic Breast Cancer Cell Lines This example compares the effect on gastrin gene expression in MDA-MB-231 and MCF7 cell lines of growth under conventional tissue culture conditions and low adherence conditions.

A. Methods

MDA-MB-231 and MCF-7 cells were grown under conventional and low adherence culture conditions. At the beginning of the experiment, 30,000 cells were grown in conventional and ultra low adherent 75 cm² flasks (Corning) in MammoCult Medium (StemCell #05621) with MammoCult Proliferation supplement (StemCell #05622), 5 ng/ml insulin, 0.5 ng/ml hydrocortisone, 100 U/ml penicillin, and 100 U/ml streptomycin. After collection, cells were dissociated in Accumax (Sigma) for 45 minutes at 37° C. prior to RNA extraction, after which total RNA was extracted according to standard techniques. Gastrin mRNA was quantified using quantitative RT-PCR. Data is expressed in comparison with gastrin mRNA levels determined in MDA-MB-435 cells, which express the gastrin gene levels just above the detection threshold.

B. Results

The results are shown in FIG. 10. In MDA-MB-231 cells, growth under low adherence culture conditions increases the amount of gastrin mRNA in such cells compared to growth under conventional tissue culture conditions. In MCF7 cells, gastrin gene expression was reduced in cells grown under low adherence conditions compared to the same type of cells grown under conventional conditions.

Example 9

Effect of Anti-hPG Monoclonal Antibody on Growth of Metastatic Breast Cancer Cells as Spheroids Under Low Adherence Culture Conditions This example describes the effect of an anti-progastrin monoclonal antibody on the growth as spheroids of the MCF-7 metastatic breast cancer cell line when such cells were grown under low adherence culture conditions.

A. Methods

MCF-7 cells were seeded into low-adherence culture plates (500 cells/well) in 500 µl of serum-free Mammocult medium. Each day for 10 days after plating, anti-hPG monoclonal antibodies (MAb8) or control monoclonal antibodies were added to the culture medium twice daily (3 µg/ml). At the end of the experiment, the number of spheroids that formed in the presence of the anti-hPG antibodies and control antibodies was counted. The experiment was carried out in blinded fashion.

B. Results

The results are shown in FIG. 11, which demonstrates that growth of MCF-7 metastatic breast cancer cells as spheroids in low adherence culture was reduced by treatment with the anti-hPG monoclonal antibody MAb8 as compared to treatment with a non-specific control antibody.

Example 10

Effect of Pre-Treatment with an Anti-Progastrin Monoclonal Antibody on Growth of Metastatic Breast Cancer Cells as Spheroids Under Low Adherence Culture Conditions This example describes the effect of pretreatment using an anti-progastrin monoclonal antibody on the growth as spheroids of the MCF-7 metastatic breast cancer cell line when grown under low adherence culture conditions.

A. Methods

Cells were first grown in conventional adherent culture for 48 hours in the presence of an anti-hPG monoclonal antibody (MAb3) or control monoclonal antibody. At the end of treatment 500 cells/well were plated into low-adherence 24-well plates in 500 µl of serum-free Mammocult medium and grown for 11 days without further antibody treatment. At the end of the experiment, the number of spheres per well was counted.

B. Results

The results are shown in FIG. 12, which demonstrates that pretreatment of MCF-7 metastatic breast cancer cells with the anti-hPG monoclonal antibody MAb3 was effective to reduce the number of spheroids formed by such cells when later cultured under low adherence conditions without further antibody treatment. Because culturing under low adherence conditions selects for growth of breast cancer stem cells, these results indicate that neutralizing antibodies against PG are effective to reduce the number of such stem cells in a population of breast cancer cells. Furthermore, the observation that pretreatment with the specific antibodies effectively reduced the number of breast cancer stem cells suggests that exposing breast tumors to anti-hPG neutralizing antibodies may have lasting effects on reducing tumorigenicity of the stem cells even after the antibodies are no longer present.

Example 11

Quantification of Plasma or Serum PG Levels

Plasma and/or serum levels of PG can be conveniently determined using the following assay. 96-well microtiter plates are coated with between 0.5 and 10 µg/mL of a C-terminal anti-hPG antibody, for example, a rabbit C-terminal anti-hPG polyclonal antibody, or a C-terminal anti-hPG antibody described herein, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 µg/mL of an N-terminal anti-hPG antibody, for example, a polyclonal N-terminal anti-hPG antibody or an N-terminal monoclonal anti-hPG antibody as described herein, coupled to horseradish peroxidase (HRP) ((see, Nakane et al., 1974, J. Histochem. Cytochem. 22(12): 1084-1091)) for 30 minutes at 21° C. Plates are then washed three times in PBS-Tween (0.05%) and HRP substrate is added for 15 minutes at 21° C. The reaction is stopped by added 100 µL of 0.5M sulfuric acid and an optical density measurement is taken at 405 nm. Test sample hPG levels are determined by comparison to a standard curve constructed from the measurements derived from the hPG reference standard.

Example 12

ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 µL blocking solution (PBS, 0.1% Tween-20, 0.1% Bovine Serum Albumin or casein hydrolysate) per well. After blocking, the wells are washed three times and the antibody to be assayed (test antibody) is added. 100 µL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3×100 µL wash solution, as noted above), with blocking solution containing a secondary antibody, a goat anti-mouse IgG (Fc) antibody coupled to horseradish peroxidase. After a 1-hour incubation with secondary antibody, 100 µL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 µL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

Example 13

Assay for Assessing Neutralizing Activity of Anti-hPG Antibodies

A specific test for assessing whether a specific anti-hPG antibody is neutralizing can be performed as follows. Breast cancer cells are seeded in a 6-well plate, at approximately 50,000 to 100,000 cells per well. Cells are then treated at 12 hour intervals for 48 hours with the test anti-hPG antibody or a control antibody, at antibody concentrations of about 10 µg/mL. A test antibody is defined as neutralizing in the assay if the number of cells treated with the test antibody shows a statistically significant reduction of at least 10% in the number of surviving cells compared to the number of cells treated with a control, non-specific antibody, using a two-tailed Mann-Whitney test (with differences considered as significant when $p<0.05$). Total cell numbers are corrected for the number of cells at the start of the treatment period, referred to as $T_0$. Exemplary breast cancer cells for use in this assay include, but are not limited to, MDA-MB-231 cells and MCF7 cells.

Example 14

Assay for Assessing Affinity of an Anti-hPG Antibody

Affinity constants of anti-hPG antibodies can be measured using the Proteon Technique (BioRad), according to Nahshol et al., 2008, Analytical Biochemistry 383:52-60, hereby incorporated by reference in its entirety. Briefly, for murine anti-PG antibodies, an anti-mouse IgG antibody (50 µg/ml) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 µg/ml). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

Example 15

Assay for Assessing Competitive Binding with a Reference Anti-hPG Antibody

A specific assay for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N- or C-terminal region of hPG that differs from the epitope recognized by the biotinylated reference anti-hPG antibody), at a concentration to be chosen within the range of 1-10 µg/ml, overnight at 4° C. (0.1 to 1 µg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/ml steptavidin-HRP for 1 hr at 22° C., followed by incubation with a fluorogenic substrate for horseradish peroxidase and then quantifying the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody.

In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$, which is calculated according to the following formula:

$$K_i = IC_{50}/(1+([\text{reference anti-hPG Ab concentration}]/K_D^{\text{reference anti-hPG Ab}}))$$

where "$IC_{50}$" is the concentration of test antibody that yields a 50% reduction in binding of the reference antibody and $K_D^{\text{reference anti-hPG Ab}}$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for treating breast cancer, comprising the step of administering to a patient in need of treatment for breast cancer a therapeutically effective amount of a composition comprising a neutralizing anti-hPG monoclonal antibody that specifically binds to hPG and competes for binding to hPG with a reference antibody selected from:
   (a) a monoclonal antibody comprising a heavy variable domain sequence of SEQ ID NO:12 and a light chain variable domain sequence of SEQ ID NO:13;
   (b) a monoclonal antibody comprising a heavy variable domain sequence of SEQ ID NO:59 and a light chain variable domain sequence of SEQ ID NO:63;
   (c) a monoclonal antibody comprising a heavy variable domain sequence of SEQ ID NO:60 and a light chain variable domain sequence of SEQ ID NO:64;
   (d) a monoclonal antibody comprising a heavy variable domain sequence of SEQ ID NO:61 and a light chain variable domain sequence of SEQ ID NO:65; and
   (e) a monoclonal antibody comprising a heavy variable domain sequence of SEQ ID NO:62 and a light chain variable domain sequence of SEQ ID NO:66.

2. The method of claim 1, wherein said breast cancer is a primary breast cancer.

3. The method of claim 1, wherein said breast cancer is metastatic breast cancer.

4. The method of claim 1, wherein the step of administering said composition is effected before surgical resection of a breast tumor.

5. The method of claim 1, wherein the step of administering said composition is effected after surgical resection of a breast tumor.

6. The method of claim 1, wherein said composition is administered adjunctive to chemotherapy or radiation therapy.

7. The method of claim 6, wherein said chemotherapy includes treatment with a chemotherapeutic agent selected from the group consisting of folate antagonists, purine antagonists, pyrimidine antagonists, DNA alkylating agents, DNA cross-linking drugs, antibiotics, platinum complexes, proteosome inhibitors, mitotic spindle poisons, topoisomerase inhibitors, and tyrosine kinase inhibitors.

8. The method of claim 1, wherein the composition is administered adjunctive to a hormone therapy agent.

9. The method of claim 8, in which the hormone therapy agent is bicalutamide, flutamide, fulvestrant, leuprolide acetate, megestrol acetate, tamoxifen, raloxifene, anastrozole, exemestane or letrozole.

10. The method of claim 1, wherein the composition is administered adjunctive to a second therapeutic antibody that specifically binds EGFR, VEGF, or HER2.

11. The method of claim 10, in which the second therapeutic antibody is panitumumab, bevacizumab, cetuximab or trastuzumab.

12. The method of claim 1, wherein said composition is administered by a mode of administration selected from among the group consisting of: parenteral administration, intrathecal administration, intravenous administration, subcutaneous administration, intramuscular administration, intraperitoneal administration, infusion administration, and bolus administration.

13. The method of claim 1, wherein said composition is administered at a neutralizing anti-hPG monoclonal antibody dose ranging from about 0.001 mg/kg to about 250 mg/kg.

14. The method of claim 13, wherein said neutralizing anti-hPG monoclonal antibody dose is administered over a plurality of temporally spaced administrations.

15. The method of claim 1, wherein said reference antibody comprises a heavy variable domain sequence of SEQ ID NO:12 and a light chain variable domain sequence of SEQ ID NO:13.

16. The method of claim 15, wherein said neutralizing anti-hPG monoclonal antibody inhibits binding of the reference antibody to hPG with a $K_i$ ranging from 10 pM to 100 nM; wherein said $K_i$ is determined using an assay comprising the following steps:
   (a) coating the wells of a 96-well plate with a capture anti-hPG antibody using a concentration of capture anti-hPG antibody from 1 to 10 μg/mL overnight at 4° C., wherein said capture anti-hPG antibody binds an epitope different than the neutralizing anti-hPG antibody;
   (b) blocking the coated wells with a blocking buffer;
   (c) incubating the coated wells with hPG at a concentration between 10 pM and 1 nM for 2 hours at 22° C.;
   (d) incubating the coated wells with biotinylated reference antibody and increasing concentrations of unlabeled neutralizing anti-hPG antibodies for 1 hour at 22° C.;
   (e) removing unbound antibodies;
   (f) detecting bound labeled biotinylated reference antibody using streptavidin-HRP and a fluorogenic substrate.

17. The method of claim 1, wherein said reference antibody comprises a heavy variable domain sequence of SEQ ID NO:59 and a light chain variable domain sequence of SEQ ID NO:63.

18. The method of claim 17, wherein said neutralizing anti-hPG monoclonal antibody inhibits binding of the reference antibody to hPG with a $K_i$ ranging from 10 pM to 100 nM; wherein said $K_i$ is determined using an assay comprising the following steps:
   (a) coating the wells of a 96-well plate with a capture anti-hPG antibody using a concentration of capture anti-hPG antibody from 1 to 10 μg/mL overnight at 4° C., wherein said capture anti-hPG antibody binds an epitope different than the neutralizing anti-hPG antibody;
   (b) blocking the coated wells with a blocking buffer;
   (c) incubating the coated wells with hPG at a concentration between 10 pM and 1 nM for 2 hours at 22° C.;
   (d) incubating the coated wells with biotinylated reference antibody and increasing concentrations of unlabeled neutralizing anti-hPG antibodies for 1 hour at 22° C.;
   (e) removing unbound antibodies;
   (f) detecting bound labeled biotinylated reference antibody using streptavidin-HRP and a fluorogenic substrate.

19. The method of claim 1, wherein said reference antibody comprises a heavy variable domain sequence of SEQ ID NO:60 and a light chain variable domain sequence of SEQ ID NO:64.

20. The method of claim 19, wherein said neutralizing anti-hPG monoclonal antibody inhibits binding of the reference antibody to hPG with a $K_i$ ranging from 10 pM to 100 nM; wherein said $K_i$ is determined using an assay comprising the following steps:
   (a) coating the wells of a 96-well plate with a capture anti-hPG antibody using a concentration of capture anti-hPG antibody from 1 to 10 μg/mL overnight at 4° C., wherein said capture anti-hPG antibody binds an epitope different than the neutralizing anti-hPG antibody;
   (b) blocking the coated wells with a blocking buffer;
   (c) incubating the coated wells with hPG at a concentration between 10 pM and 1 nM for 2 hours at 22° C.;
   (d) incubating the coated wells with biotinylated reference antibody and increasing concentrations of unlabeled neutralizing anti-hPG antibodies for 1 hour at 22° C.;
   (e) removing unbound antibodies;
   (f) detecting bound labeled biotinylated reference antibody using streptavidin-HRP and a fluorogenic substrate.

21. The method of claim 1, wherein said reference antibody comprises a heavy variable domain sequence of SEQ ID NO:61 and a light chain variable domain sequence of SEQ ID NO:65.

22. The method of claim 21, wherein said neutralizing anti-hPG monoclonal antibody inhibits binding of the reference antibody to hPG with a $K_i$ ranging from 10 pM to 100 nM; wherein said $K_i$ is determined using an assay comprising the following steps:
   (a) coating the wells of a 96-well plate with a capture anti-hPG antibody using a concentration of capture anti-hPG antibody from 1 to 10 μg/mL overnight at 4° C., wherein said capture anti-hPG antibody binds an epitope different than the neutralizing anti-hPG antibody;
   (b) blocking the coated wells with a blocking buffer;
   (c) incubating the coated wells with hPG at a concentration between 10 pM and 1 nM for 2 hours at 22° C.;
   (d) incubating the coated wells with biotinylated reference antibody and increasing concentrations of unlabeled neutralizing anti-hPG antibodies for 1 hour at 22° C.;
   (e) removing unbound antibodies;
   (f) detecting bound labeled biotinylated reference antibody using streptavidin-HRP and a fluorogenic substrate.

23. The method of claim 1, wherein said reference antibody comprises a heavy variable domain sequence of SEQ ID NO:62 and a light chain variable domain sequence of SEQ ID NO:66.

24. The method of claim 23, wherein said neutralizing anti-hPG monoclonal antibody inhibits binding of the reference antibody to hPG with a $K_i$ ranging from 10 pM to 100 nM; wherein said $K_i$ is determined using an assay comprising the following steps:
   (a) coating the wells of a 96-well plate with a capture anti-hPG antibody using a concentration of capture anti-hPG antibody from 1 to 10 μg/mL overnight at 4° C., wherein said capture anti-hPG antibody binds an epitope different than the neutralizing anti-hPG antibody;
   (b) blocking the coated wells with a blocking buffer;
   (c) incubating the coated wells with hPG at a concentration between 10 pM and 1 nM for 2 hours at 22° C.;
   (d) incubating the coated wells with biotinylated reference antibody and increasing concentrations of unlabeled neutralizing anti-hPG antibodies for 1 hour at 22° C.;
   (e) removing unbound antibodies;
   (f) detecting bound labeled biotinylated reference antibody using streptavidin-HRP and a fluorogenic substrate.

25. The method of claim 1, wherein said neutralizing anti-hPG monoclonal antibody comprises a heavy chain variable region in which complementarity determining region (CDR) 1 comprises the amino acid sequence of $V_H$ CDR 1.3 (SEQ ID NO:1), CDR2 comprises the amino acid sequence of $V_H$ CDR 2.3 (SEQ ID NO:2), and CDR3 comprises the amino acid sequence of $V_H$ CDR 3.3 (SEQ ID NO:3), and a light chain variable region in which CDR1 comprises the amino acid sequence of $V_L$ CDR 1.3 (SEQ ID NO:4), CDR2 comprises the amino acid sequence of $V_L$ CDR 2.3 (SEQ ID NO:5), and CDR3 comprises the amino acid sequence of $V_L$ CDR 3.3 (SEQ ID NO:6).

26. The method of claim 1, wherein said neutralizing anti-hPG monoclonal antibody comprises a heavy chain variable region in which CDR1 comprises the amino acid sequence of $V_H$ CDR 1.8 (SEQ ID NO:37), CDR2 comprises the amino acid sequence of $V_H$ CDR 2.8 (SEQ ID NO:41), and CDR3 comprises the amino acid sequence of $V_H$ CDR 3.8 (SEQ ID NO:45), and a light chain variable region in which CDR1 comprises the amino acid sequence of $V_L$ CDR 1.8 (SEQ ID NO:49), CDR2 comprises the amino acid sequence of $V_L$ CDR 2.8 (SEQ ID NO:52), and CDR3 comprises the amino acid sequence of $V_L$ CDR 3.8 (SEQ ID NO:55).

27. The method of claim 1, wherein said neutralizing anti-hPG monoclonal antibody comprises a heavy chain variable region in which CDR1 comprises the amino acid sequence of $V_H$ CDR 1.13 (SEQ ID NO:38), CDR2 comprises the amino acid sequence of $V_H$ CDR 2.13 (SEQ ID NO:42), and CDR3 comprises the amino acid sequence of $V_H$ CDR 3.13 (SEQ ID NO:46), and a light chain variable region in which CDR1 comprises the amino acid sequence of $V_L$ CDR 1.13 (SEQ ID NO:50), CDR2 comprises the amino acid sequence of $V_L$ CDR 2.13 (SEQ ID NO:53), and CDR3 comprises the amino acid sequence of $V_L$ CDR 3.13 (SEQ ID NO:56).

28. The method of claim 1, wherein said neutralizing anti-hPG monoclonal antibody comprises a heavy chain variable region in which CDR1 comprises the amino acid sequence of $V_H$ CDR 1.16 (SEQ ID NO:39), CDR2 comprises the amino acid sequence of $V_H$ CDR 2.16 (SEQ ID NO:43), and CDR3 comprises the amino acid sequence of $V_H$ CDR 3.16 (SEQ ID NO:47), and a light chain variable region in which CDR1 comprises the amino acid sequence of $V_L$ CDR 1.16 (SEQ ID NO:50), CDR2 comprises the amino acid sequence of $V_L$ CDR 2.16 (SEQ ID NO:53), and CDR3 comprises the amino acid sequence of $V_L$ CDR 3.16 (SEQ ID NO:57).

29. The method of claim 1, wherein said neutralizing anti-hPG monoclonal antibody comprises a heavy chain variable region in which CDR1 comprises the amino acid sequence of $V_H$ CDR 1.19 (SEQ ID NO:40), CDR2 comprises the amino acid sequence of $V_H$ CDR 2.19 (SEQ ID NO:44), and CDR3 comprises the amino acid sequence of $V_H$ CDR 3.19 (SEQ ID NO:48), and a light chain variable region in which CDR1 comprises the amino acid sequence of $V_L$ CDR 1.19 (SEQ ID NO:51), CDR2 comprises the amino acid sequence of $V_L$ CDR 2.19 (SEQ ID NO:54), and CDR3 comprises the amino acid sequence of $V_L$ CDR 3.19 (SEQ ID NO:58).

30. The method of any one of claims 1 and 15-29, wherein said neutralizing anti-hPG monoclonal antibody is humanized.

31. The method of any one of claims 1 and 15-24, wherein said neutralizing anti-hPG monoclonal antibody has an hPG binding affinity in a range of about 0.001 nM to about 5000 nM.

32. A method for preventing recurrence of breast cancer, comprising the step of administering to a patient in need of prevention of recurrence of breast cancer a composition comprising a neutralizing anti-hPG monoclonal antibody that specifically binds to hPG in an amount effective to prevent recurrence of breast cancer, wherein said breast cancer is hPG sensitive, and wherein said neutralizing anti-hPG monoclonal antibody competes for binding to hPG with a reference antibody selected from:
(a) a monoclonal antibody comprising a heavy variable domain sequence of SEQ ID NO:12 and a light chain variable domain sequence of SEQ ID NO:13;
(b) a monoclonal antibody comprising a heavy variable domain sequence of SEQ ID NO:59 and a light chain variable domain sequence of SEQ ID NO:63;
(c) a monoclonal antibody comprising a heavy variable domain sequence of SEQ ID NO:60 and a light chain variable domain sequence of SEQ ID NO:64;
(d) a monoclonal antibody comprising a heavy variable domain sequence of SEQ ID NO:61 and a light chain variable domain sequence of SEQ ID NO:65; and
(e) a monoclonal antibody comprising a heavy variable domain sequence of SEQ ID NO:62 and a light chain variable domain sequence of SEQ ID NO:66.

33. A method of inhibiting proliferation of a breast cancer stem cell, comprising exposing a breast cancer stem cell with a CD44(+)/CD24(−), CD44(+)/CD24(low) or CD44(+)/CD24(−)/ESA(+) marker phenotype to an amount of a neutralizing anti-hPG monoclonal antibody effective to inhibit its proliferation, wherein said neutralizing anti-hPG monoclonal antibody specifically binds to hPG and competes for binding to hPG with a reference antibody selected from:
(a) a monoclonal antibody comprising a heavy variable domain sequence of SEQ ID NO:12 and a light chain variable domain sequence of SEQ ID NO:13;
(b) a monoclonal antibody comprising a heavy variable domain sequence of SEQ ID NO:59 and a light chain variable domain sequence of SEQ ID NO:63;
(c) a monoclonal antibody comprising a heavy variable domain sequence of SEQ ID NO:60 and a light chain variable domain sequence of SEQ ID NO:64;
(d) a monoclonal antibody comprising a heavy variable domain sequence of SEQ ID NO:61 and a light chain variable domain sequence of SEQ ID NO:65; and
(e) a monoclonal antibody comprising a heavy variable domain sequence of SEQ ID NO:62 and a light chain variable domain sequence of SEQ ID NO:66.

\* \* \* \* \*